(12) United States Patent
Chung et al.

(10) Patent No.: US 8,138,163 B2
(45) Date of Patent: Mar. 20, 2012

(54) ALDEHYDE CONJUGATED FLAVONOID PREPARATIONS

(75) Inventors: Joo Eun Chung, Singapore (SG); Motoichi Kurisawa, Singapore (SG); Yi Yan Yang, Singapore (SG); Lang Zhuo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 12/952,141

(22) Filed: Nov. 22, 2010

(65) Prior Publication Data

US 2011/0135733 A1 Jun. 9, 2011

Related U.S. Application Data

(60) Division of application No. 11/554,450, filed on Oct. 30, 2006, now Pat. No. 7,858,080, which is a continuation-in-part of application No. PCT/SG2006/000045, filed on Mar. 7, 2006.

(60) Provisional application No. 60/682,801, filed on May 20, 2005.

(51) Int. Cl.
*A61K 31/787* (2006.01)
*A61K 9/50* (2006.01)
(52) U.S. Cl. .......... 514/54; 514/449; 514/451; 514/453; 514/456
(58) Field of Classification Search .................. 424/85.1, 424/94.1; 514/8, 12, 27, 457
See application file for complete search history.

(56) References Cited

U.S. PATENT DOCUMENTS

| 6,864,350 | B2 | 3/2005 | Harris |
| 7,196,180 | B2 | 3/2007 | Aeschlimann et al. |
| 7,399,783 | B2 | 7/2008 | Rosenbloom |
| 2004/0062748 | A1 | 4/2004 | Martinez et al. |
| 2005/0220753 | A1 | 10/2005 | Ji et al. |

FOREIGN PATENT DOCUMENTS

| EP | 296740 A2 | 12/1988 |
| EP | 1273308 A1 | 1/2003 |
| EP | 1496076 A1 | 1/2005 |
| JP | 09-003089 | 1/1997 |
| JP | 10-101705 | 4/1998 |
| JP | 2003-137925 | 5/2003 |
| JP | 2003-138258 | 5/2003 |
| WO | WO 00/74662 A2 | 12/2000 |

OTHER PUBLICATIONS

Young-Jin Kim, Joo Eun Chung, Motoichi Kurisawa, Kiroshi Uyamam, Shiro Kobayashi, Regioselective Synthesis and Structures of (+)-Catechin-Aldehyde polycondensates, Macromol. Chem. Phys. 2003, 204(15), 1863-1868.*

Jankun, J., Selman, S.H., Swiercz, R. and Skrzypczak-Jankun, E., "Why drinking green tea could prevent cancer", Nature, Jun. 5, 1997, p. 561, vol. 387, No. 6633.
Bordoni, A. et al., "Green tea protection of hypoxia/reoxygenation injury in cultured cardiac cells", The Journal of Nutritional Biochemistry, Feb. 2002 pp. 103-111, vol. 13, Issue 2.
Nakagawa, K. et al., "Tea Catechin Supplementation Increases Antioxidant Capacity and Prevents Phospholipid Hydroperoxidation in Plasma of Humans", Journal of Agricultural and Food Chemistry, 1999, pp. 3967-3973, vol. 47, Issue 10.
Terao, J., Piskula, M. and Yao, Q., "Protective Effect of Epicatechin, Epicatechin Gallate, and Quercetin on Lipid Peroxidation in Phospholipid Bilayers", Archives of Biochemistry and Biophysics, Jan. 1994, pp. 278-284, vol. 308, Issue 1.
Isemura, M., Saeki, K., Kimura, T., Hayakawa, S., Minami, T. and Sazuka, M., "Tea catechins and related polyphenols as anti-cancer agents", BioFactors 2000, pp. 81-85, vol. 13, Nos. 1-4.
Ikeda, I., Tsuda, K., Suzuki, Y., Kobayashi, M., Unno, T Tomoyori, H., Goto, H., Kawata, Y., Imaizumi, K., Nozawa, A. and Kakuda, T., "Tea Catechins with a Galloyl Moiety Suppress Postprandial Hypertriacylglycerolemla by Delaying Lymphatic Transport of Dietary Fat in Rats", The Journal of Nutrition, Feb. 2005, pp. 55-159, vol. 135, Issue 2.
Lill, G., Voit, S., Schror, K. and Weber, A-A., "Complex effects of different green tea catechins on human platelets", FEBS Letters, Jul. 10, 2003, pp. 265-270, vol. 546, Issues 2-3.
Sakanaka S. and Okada Y. "Inhibitory Effects of Green Tea Polyphenols on the Production of a Virulence Factor of the Periodontal-Disease-Causing Anaerobic Bacterium *Porphyromonas gingivalis*", Journal of Agricultural and Food Chemistry, Mar. 24, 2004, pp. 1688-1692, vol. 52, Issue 6.
Yokozawa, T., Cho, E. J., Hara, Y. and Kitani, K., "Antioxidative Activity of Green Tea Treated with Radical Initiator 2,2'-Azobis(2-amidinopropane) Dihydrochloride", Journal of Agricultural and Food Chemistry, Oct. 2000, pp. 5068-5073, vol. 48, Issue 10.
Yen, G.C., Chen, H.Y. and Peng, H.H., "Antioxidant and Pro-Oxidant Effects of Various Tea Extracts", Journal of Agricultural and Food Chemistry, Jan. 1997, pp. 30-34, vol. 45, Issue 1.
Yamanaka, N., Oda, O. and Nagao, S., "Green tea catechins such as (-)-epicatechin and (-)—epigallocatechin accelerate Cu2+-induced low density lipoprotein oxidation in propagation phase", FEBS Letters, Jan. 20, 1997, pp. 230-234, vol. 401, Issue 2-3. Roedig-Penman, A. and Gordon, M.H., "Antioxidant Properties of Catechins and Green Tea Extracts in Model Food Emulsions", Journal of Agricultural and Food Chemistry, Nov. 1997, pp. 4267-4270, vol. 45, Issue 11.
Zhao, J., Wang, J., Chen, Y. and Agarwal, R., "Anti-tumor-promoting activity of a polyphenolic fraction isolated from grape seeds in the mouse skin two-stage initiation-promotion protocol and Identification of procyanidin B5-3'-gallate as the most effective antioxidant constituent", Carcinogenesis, Sep. 1999, pp. 1737-1745, vol. 20, Issue 9.
Ariga, T. and Hamano, M., "Radical Scavenging Action and Its Mode in Procyanidins B-1 and B-3 from Azuki Beans to Peroxyl Radicals", Agricultural and Biological Chemistry, 1990, pp. 2499-2504, vol. 54, Issue 10.

(Continued)

*Primary Examiner* — Michael G Hartley
*Assistant Examiner* — Jagadishwar Samala
(74) *Attorney, Agent, or Firm* — Klarquist Sparkman, LLP

(57) ABSTRACT

There is provided a method of conjugating a polymer containing a free aldehyde group with a flavonoid in the presence of an acid catalyst, such that the polymer is conjugated to the C6 or C8 position of the flavonoid A ring. The resulting conjugates may be used to form delivery vehicles to deliver high doses of flavonoids, and may also be used as delivery vehicles to deliver an additional bioactive agent.

10 Claims, 30 Drawing Sheets

OTHER PUBLICATIONS

Saito, M., Hosoyama, H., Ariga, T., Kataoka, S. and Yamaji, N., "Antiulcer Activity of Grape Seed Extract and Procyanidins", Journal of Agricultural and Food Chemistry, Apr. 1998, pp. 1460-1464, vol. 46, Issue 4.

Hagerman, A.E., Riedl, K.M., Jones, G.A., Sovik, K.N., Ritchard, N.T., Hartzfeld, P.W. and Riechel, T.L., "High Molecular Weight Polyphenolics (Tannins) as Biological Antioxidants", Journal of Agricultural and Food Chemistry, May 1998, pp. 1887-1892, vol. 46, Issue 5.

Duweler, K.G. and Rohdewald, P., "Urinary metabolites of French maritime pine bark extract in human.", Pharmazie, 2000, pp. 364-368, vol. 55.

Li, C. and Xie, B., "Evaluation of the Antioxidant and Pro-oxidant Effects of Tea Catechin Oxypolymers", Journal of Agricultural and Food Chemistry, Dec. 2000, pp. 6362-6366, vol. 48, Issue 12.

Chung, J.E., Kurisawa, M., Kim, Y.-J., Uyama, H. and Kobayashi, S., "Amplification of Antioxidant Activity of Catechin by Polycondensation with Acetaldehyde", Biomacromolecules, Jan. 2004, pp. 113-118, vol. 5, Issue 1.

Kurisawa, M., Chung, J.E., Uyama, H. and Kobayashi, S., "Laccase-catalyzed Synthesis and Antioxidant Property of Poly(catechin)", Macromolecular Bioscience, Dec. 2003, pp. 758-764, vol. 3, Issue 12.

Kurisawa, M., Chung, J.E., Kim, Y.-J., Uyama, H. and Kobayashi, S., "Amplification of Antioxidant Activity and Xanthine Oxidase Inhibition of Catechin by Enzymatic Polymerization", Biomacrocolecules, 4, pp. 469-471 (2003).

Kurisawa, M., Chung, J.E., Uyama, H. and Kobayashi S., "Enzymatic Synthesis and Antioxidant Properties of Poly(rutin)", Biomacromolecules, Sep. 2003, pp. 1394-1399, vol. 4, Issue 5.

Kim, Y.-J., Chung, J. E., Kurisawa, M., Uyama, H. and Kobayashi, S., "New Tyrosinase Inhibitors, (+)-Catechin-Aldehyde Polycondensates", Biomacromolecules, Mar. 2004, pp. 474-479, vol. 5, Issue 2.

Kim, Y.-J., Chung, J.E., Kurisawa, M., Uyama, H. and Kobayashi, S., "Superoxide Anion Scavenging and Xanthine Oxidase Inhibition of (+)-Catechin-Aldehyde Polycondensates. Amplification of the Antioxidant Property of (+)-Catechin by Polycondensation with Aldehydes", Biomacromolecules, Mar. 2004, pp. 547-552, vol. 5, Issue 2.

Meijas, L., Reihmann, M.H., Sepulveda-Boza, S. and Ritter, H., "New Polymers from Natural Phenols Using Horseradish or Soybean Peroxidase", Macromolecular Bioscience, Jan. 2003, pp. 24-32, vol. 2, Issue 1.

Guyot, S., Cheynier, V., Souquet, J.-M. and Moutounet, M., "Influence of pH on the Enzymatic Oxidation of (+)-Catechin in Model Systems", Journal of Agricultural and Food Chemistry, Sep. 2005, pp. 2458-2462, vol. 43, Issue 9.

Guyot, S., Vercauteren, J. and Cheynier, V., "Structural determination of colourless and yellow dimers resulting from (+)-catechin coupling catalysed by grape polyphenoloxidase", Phytochemistry, Jul. 1996, pp. 1279-1288, vol. 42, Issue 5.

Lopez-Serrano, M. and Ros Barcelo, A., "Reversed-phase and size-exclusion chromatography as useful tools in the resolution of peroxidase-mediated (+)-catechin oxidation products", Journal of Chromatography A, Jun. 15, 2001, pp. 267-273, vol. 919, Issue 2.

Lopez-Serrano, M. and Ros Barcelo. A., "Comparative Study of the Products of the Peroxidase-Catalyzed and the Polyphenoloxidase-Catalyzed (+)-Catechin Oxidation. Their Possible Implications in Strawberry (Fragaria × ananassa) Browning Reactions", Journal of Agricultural and Food Chemistry, Feb. 27, 2002, pp. 1218-1224, vol. 50, Issue 5.

Hamada, S., Kontani, M., Hosono, H., Ono, H., Tanaka, T., Ooshima, T., Mitsunaga, T. and Abe, I., "Peroxidase-catalyzed generation of catechin oligomers that inhibit glucosyltransferase from *Streptococcus sobrinus*", FEMS Microbiology Letters, Sep. 15, 1996 pp. 35-40, vol. 143, Issue 1.

Dickinson R. G. and Jacobson, N. W. A New Sensitive and Specific Test for the Detection of Aldehydes: Formation of 6-Mercapto-3-substituted-s-triazolo[3,4-b]-s-tetrazines.:, Chemical Communication 1970, pp. 1719-1720.

Morishita Y. et al. Eisei Kensa 29, 811 (1980).

Julkunen-Tiitto, R., "Phenolic Constituents in the Leaves of Northern Willows: Methods for the Analysis of Certain Phenolics", Journal of Agricultural and Food Chemistry, Mar. 1985, pp. 213-217, vol. 33, Issue 2.

Broadhurst, R.B. and Jones, W.T., "Analysis of condensed tannins using acidified vanillin", Journal of the Science of Food and Agriculture, Sep. 1978, pp. 788-794, vol. 29, Issue 9.

Saucier, C., Bourgeois, G., Vitry, C., Roux, D. and Glories, Y., "Characterization of (+)-Catechin-Acetaldehyde Polymers: A Model for Colloidal State of Wine Polyphenols", Journal of Agricultural and Food Chemistry, Apr. 1997, pp. 1045-1049, vol. 45, Issue 4.

Es-Safi, N.-E., Fulcrand, H., Cheynier, V. and Moutounet, M., "Competition between (+)-Catechin and (−)-Epicatechin in Acetaldehyde-Induced Polymerization of Flavanols", Journal of Agricultural and Food Chemistry, May 1999, pp. 2088-2095, vol. 47, Issue 5.

Fulcrand, H., Doco, T., Es-Safi, N.-E., Cheynier, V. and Moutounet, M., "Study of the acetaldehyde induced polymerisation of flavan-3-ols by liquid chromatography-ion spray mass spectrometry", Journal of Chromatography A, Nov. 1, 1996, pp. 85-91, vol. 752, Issue 1-2.

Saucier, C., Guerra, C., Pianet, I., LaGuerre, M. and Glories, Y., "(+)-Catechin-acetaldehyde condensation products in relation to wine-ageing", Phytochemistry, Sep. 1997, pp. 229-234, vol. 46, Issue 2.

Saucier, C., Pianet, I., Laguerre, M. and Glories, Y., "NMR and molecular application to wine ageing", Journal de Chimie Physique et de Physico-Chimie Biologique, Feb. 1998, pp. 357-365, vol. 95, No. 2.

Es-Safi, N.-E., Cheynier, V. and Moutounet, M., "Role of Aldehydic Derivatives in the Condensation of Phenolic Compounds with Emphasis on the Sensorial Properties of Fruit-Derived Foods", Journal of Agricultural and Food Chemistry, Sep. 25, 2002 pp. 5571-5585, vol. 50, Issue 20.

Kim, Y.-J., Chung, J.E., Kurisawa, M., Uyama, H. and Kobayashi, S., "Regioselective Synthesis and Structure of (+)-Catechin-Aldehyde Polycondensates", Macromolecular Chemistry and Physics, Oct. 2003, pp. 1863-1868, vol. 204, Issue 15.

Takagaki, A., Fukai, K., Nanjo, F. and Hara, Y., "Reactivity of green tea catechins with formaldehyde", Journal of Wood Science, Jul. 2000, pp. 334-338, vol. 46, No. 4.

Folin, O. and Ciocalteu, U., "On tyrosine tryptophane determinations in proteins", The Journal of Biological Chemistry, Jun. 1, 1927, pp. 627-650, vol. 73, Issue 2.

Jovanovic, S.V., Steenken, S., Tosic, M., Marjanovic, B. and Simic, M.G., "Flavonoids as Antioxidants", Journal of the American Chemical Society, Jun. 1, 1994, pp. 4846-4851, vol. 116.

Yen, G.C. and Chen, H. Y., "Antioxidant Activity of Tea Extracts in Relation to Their Antimutagenicity", Journal of Agricultural and Food Chemistry, Jan. 1995, 27-32, vol. 43, Issue 1.

Furuno, K., Akasako, T. and Sugihara, N., "The contribution of the pyrogallol moiety to the superoxide radical scavenging activity of flavonoids", Biological and Pharmaceutical Bulletin, Jan. 2002, pp. 19-23, vol. 25, No. 1.

Chung, J.E., Kurisawa, M. and Yang, Y.Y. (2005).

Fantone, J.C. and Ward, P.A., "Polymorphonuclear leukocyte-mediated cell and tissue injury: oxygen metabolites and their relations to human disease", Human Pathology, 1985, pp. 973-978, vol. 16.

Halliwell, B. Free radicals in biology and medicine. (ed. Gutteridge, J. M. C.) (Clarendon Press, Oxford, 1989).

McCord, J.M. and Fridovich, I., "The Reduction of Cytochrome c by Milk Xanthine Oxidase", Journal of Biological Chemistry, Nov. 10, 1968, pp. 5753-5760, vol. 243, Issue 21.

Chiang, H.C., Lo, Y.J. and Lu, F.J., "Xanthine oxidase inhibitors from the leaves of alsophila spinulosa (hook) tryon.", J. Enzyme Inhibition pp. 61-71, vol. 8, Issue 1.

Feher, M.D., Hepburn, A.L., Hogarth, M.B., Ball, S.G. and Kaye, S.A., "Fenofibrate enhances urate reduction in men treated with allopurinol for hyperuricaemia and gout", Rheumatology, Feb. 2003, pp. 321-325, vol. 42, No. 2.

Hagerman, A.E. Tannin-protein interactions. In phenolic Compounds in Food and Their Effects a Health I. Analysis, Occurrence, and Chemistry. ACS Symposium Series 506, Ho C. T., Lee C. Y., Huang M. T., Eds., American Chemical Society, Washington D. C. 1992, 236-247.

Riedl, K.M. and Hagerman, A.E., "Tannin-Protein Complexes as Radical Scavengers and Radical Sinks", Journal of Agricultural and Food Chemistry, Oct. 2001, pp. 4917-4923, vol. 49, Issue 10.

Moini, H., Guo, Q. and Packer, L., "Enzyme Inhibition and Protein-Binding Action of the Procyanidin-Rich French Maritime Pine Bark Extract, Pycnogenol: Effect on Xanthine Oxidase", Journal of Agricultural and Food Chemistry, Nov. 2000, pp. 5630-5639, vol. 48, Issue 11.

Homey, B., Muller, A. and Zlotnik, A., "Chemokines: agents for the immunotherapy of cancer?", Nature Reviews Immunology, Mar. 2002 pp. 175-184, vol. 2, No. 3.

Egilmez, N.K., Jong, Y.S., Iwanuma, Y., Jacob, J.S., Santos, C.A., Chen, F.-A., Mathiowitz, E., Bankert, R.B., "Cytokine immunotherapy of cancer with controlled release biodegradable microspheres in a human tumor xenograft/SCID mouse model", Cancer Immunology, Immunotherapy, Mar. 1998, pp. 21-24, vol. 46, No. 1.

Schwendemann, S.P., Cardamone, M., Klibanov, A. and Langer, R. Stability of proteins and their delivery from biodegradable polymer microsphere. Microparticulate systems for the delivery of proteins and vaccines (S. Cohen, H. Bernstein Eds.) pp. 1-49, Marcel Dekker, New York, 1996.

Chung, J.E., Kurisawa, M., Yang, Y.Y. and Zhuo, L. (2005).

Murray, N.J., Williamson, M.P., Lilley T. H. and Haslam E. "Study of the interaction between salivary proline-rich proteins and a polyphenol by 1H-NMR spectroscopy", European Journal of Biochemistry, Feb. 1994, pp. 923-935, vol. 219, Issue 3.

Baxter, N.J., Lilley, T.H., Haslam, E. and Williamson, M.P, "Multiple Interactions between Polyphenols and a Salivary Proline-Rich Protein Repeat Result in Complexation and Precipitation", Biochemistry, May 6, 1997, pp. 5566-5577, vol. 36, Issue 18.

Siebert, K.J., Troukhanova, N.V. and Penelope, Y.L., "Nature of Polyphenol-Protein Interactions", Journal of Agricultural and Food Chemistry, Jan. 1996, pp. 80-85, vol. 44, Issue 1.

Matsumura, Y. and Maeda, H., "A New Concept for Macromolecular Therapeutics in Cancer Chemotherapy: Mechanism of Tumoritropic Accumulation of Proteins and the Anitumor Agent Smancs", Cancer Research, Dec. 1, 1986 pp. 6387-6392, vol. 46, Issue 12, Part 1.

Jobstl, E., O'Connell, J., Fairclough, J.P.A. and Williamson, M.P., "Molecular Model for Astringency Produced by Polyphenol/Protein Interactions", Biomacromolecules, May 2004, pp. 942-949, vol. 5, Issue 3.

Kurisawa, M., et al., "Oxidative coupling of epigallocatechin amplifies antioxidant activity and inhibits xanthine oxidase activity", Chem. Commun., 2004, pp. 294-295, vol. 126, Issue 3.

Simon, M., et al., "Self-Assembling Nanocomplexes from Insulin and Water-Soluble Branched Polyesters, Poly[(vinyl-3-(diethylamino)- propylcarbamate-co-(vinyl acetate)-co-(vinyl alcohol)]-graft- poly(L-lactic acid): A Novel Carrier for Transmucosal Delivery of Peptides", Bioconjugate Chemistry, Jul. 2004, pp. 841-849, vol. 15, Issue 4.

Morishita Y. et al. Chem Abstr. 94, 61043d (1981).

Nijveldt, R.J. et al., "Flavonoids: a review of probable mechanisms of action and potential applications.", The American Journal of Clinical Nutrition, Oct. 2011, pp. 418-425, vol. 74, Issue 4.

Ahmad, N. et al., "Green Tea Polyphenol Epigallocatechin-3-Gallate Differentially Modulates Nuclear Factor kB in Cancer Cells versus Normal Cells", Archives of Biochemistry and Biophysics, Apr. 15, 2000, pp. 338-346, vol. 376, Issue 2.

Jung, Y.D. and Ellis, L.M., "Inhibition of tumour invasion and angiogenesis by epigallocatechin gallate (EGCG), a major component of green tea.", International Journal of Experimental Pathology, Dec. 2001, pp. 309-316, vol. 62, Issue 6.

Paschka, A. et al., "Induction of apoptosis in prostate cancer cell lines by the green tea component, (−)-epigallocatechin-3-gallate.", Cancer Letters, Aug. 14, 1998, pp. 1-7, vol. 130, Issue 1-2.

Lambert, J.D. and Yang, C.S., "Mechanisms of Cancer Preve Tea Constituents.", The American Society for Nutritional Sciences: The Journal of Nutrition, Oct. 2003, pp. 3262S-3267S, vol. 133, Issue 10.

Yang, C.S. and Wang, Z.Y., "Tea and Cancer.", Journal of the National Cancer Institute, Jul. 7, 1993, pp. 1038-1049, vol. 85, No. 13.

Drinkine et al., "(+)-Catechin-Aldehyde Condensations: Competition Between Acetaldehyde and Glyoxylic Acid", J. Agric. Food Chem., 53:7552-755 (2005).

Chinese Office Action dated Jan. 8, 2010, issued in corresponding Chinese Application No. 200680017596.X (with English translation).

First Official Report issued in corresponding Australian Patent Application No. 2006248166 dated Jan. 17, 2011.

Extended European Search Report date Oct. 6, 2011 issued in corresponding European Patent Application No. 06717169.4.

Young-Jun Kim et al., Regioselective Synthesis and Structures of (+_-Catechin-Aldehyde Polycondensates, Macromol. Chem. Phys. 2003, 204, No. 15.

Chung Joo Eun et al. Enzymatic synthesis and antioxidant property of gelatin-catechin conjugates. Biotechnology Letters 25: 1993-199: 2003.

* cited by examiner

ALDEHYDE CONJUGATED FLAVONOID PREPARATIONS

CROSS-REFERENCE TO RELATED APPLICATIONS

This is a division of application Ser. No. 11/554,450, filed Oct. 30, 2006 now U.S. Pat. No. 7,858,080, which is a continuation-in-part of International Application No. PCT/SG2006/000045, filed Mar. 7, 2006, which claims the benefit of U.S. Provisional Application No. 60/682,801, filed May 20, 2005, the contents of all of which are hereby incorporated by reference.

FIELD OF THE INVENTION

The present invention relates generally to preparations of flavonoids, and particularly to delivery agent-conjugated flavonoids and/or delivery agent-conjugated oligomers of flavonoids.

BACKGROUND OF THE INVENTION

Flavonoids are one of the most numerous and best-studied groups of plant polyphenols. The flavonoids consist of a large group of low-molecular weight polyphonic substances naturally occurring in fruits and vegetables, and are an integral part of the human diet. Dried green tea leaves can contain as much as 30% flavonoids by weight, including a high percentage of flavonoids known as catechins (flavan-3-ol derivatives or catechin-based flavonoids), including (−)-epicatechin, (−)-epigallocatechin, (+)-catechin, (−)-epicatechin gallate and (−)-epigallocatechin gallate.

In recent years, these green tea catechins have attracted much attention because they have been recognized to have biological and pharmacological properties, including antibacterial, antineoplastic, anti-thrombotic, vasodilatory, antioxidant, anti-mutagenic, anti-carcinogenic, hypercholesterolemic, antiviral and anti-inflammatory properties, which have been demonstrated in numerous human, animal and in vitro studies (Jankun J., et al. *Nature* 387, 561 (1997); Bodoni A. et al. *J. Nutr. Biochem.* 13, 103-111 (2002); Nakagawa K. et al. *J. Agric. Food Chem.* 47, 3967-3973 (1999)). These biological and pharmacological properties are potentially beneficial in preventing diseases and protecting the stability of the genome. Many of the beneficial effects of catechins are thought to be linked to the antioxidant actions of the catechins (Terao J., et al. *Arch. Biochem. Biophys.* 308, 278-284 (1994)). Among the catechins, (−)-epigallocatechin gallate (EGCG), which is a major component of green tea, is thought to have the highest activity, possibly due to the trihydroxy B ring and the gallate ester moiety at the C3 position (Isemura M., et al. *Biofactors* 13, 81-85 (2000); Ikeda I., et al. *J. Nutr.* 135, 155 (2005); Lill G., et al. *FEBS Letters* 546, 265-270 (2003); Sakanaka S. and Okada Y. *J. Agric. Food Chem.* 52, 1688-1692 (2004); Yokozawa T., et al., *J. Agric. Food Chem.* 48, 5068-5073 (2000)).

In general, the activity half-life of flavonoids is limited to a few hours inside the body; metabolism of these compounds has not yet been established. Despite the favorable anti-oxidation and anti-cancer properties of the catechins including EGCG, it is impractical to achieve a therapeutic level of this compound in the body by directly ingesting a large amount of green tea, due to the inherent volume constraint. That is, in order to obtain a therapeutic or pharmacological benefit from flavonoids through diet alone, it would be necessary to ingest an amount of food and beverage that is larger than is practical to consume. Moreover, pro-oxidant activity has been reported for several flavonoids including EGCG, making ingesting crude green tea directly a less effective means of delivering EGCG (Yen G. C., et al. *J. Agric. Food Chem.* 45, 30-34 (1997); Yamanaka N., et al. *FEBS Lett.* 401, 230-234 (1997); Roedig-Penman A. and Gordon M. H. *J. Agric. Food Chem.* 1997, 45, 4267-4270).

On the other hand, a relatively high-molecular fraction of extracted plant polyphenols (procyanidins) and synthetically oligomerized (+)-catechin and rutin have been reported to exhibit enhanced physiological properties such as antioxidant and anti-carcinogenic activity compared to low-molecular weight flavonoids, (Zhao J., et al. *Carcinogenesis,* 1999, 20, 1737-1745; Ariga T. and Hamano M. *Agric. Biol. Chem.* 54, 2499-2504 (1990); Chung J. E., et al. *Biomacromolecules* 5, 113-118 (2004); Kurisawa M., et al. *Biomacromolecules* 4, 1394-1399 (2003); Hagerman A. E., et al. *J. Agric. Food Chem.* 46, 1887 (1998)) and without pro-oxidant effects (Hagerman A. E., et al. *J. Agric. Food Chem.* 46, 1887 (1998); Li C. and Xie B. *J. Agric. Food Chem.* 48, 6362 (2000)). However, neither naturally occurring nor synthesized high molecular weight flavonoids are expected to be absorbed and transported to other tissues after ingestion, since these compounds are typically large, form strong complexes with proteins and are resistant to degradation (Zhao J., et al. *Carcinogenesis,* 1999, 20, 1737-1745).

In cases of flavonoids consumed via oral intake of foods and beverages, the flavonoids may play a role as antioxidants to protect the digestive tract from oxidative damage during digestion. However, flavonoids can be expected to remain only in the digestive tract and thus their beneficial physiological activities are not likely to be utilized to other tissues. Moreover, their strong hydrophobicity as well as their tendency to form complexes with proteins makes parenteral delivery of these compounds difficult.

Given the beneficial nature of these compounds, it is desirable to find methods of delivery that would allow for larger quantities to be consumed, or would provide for the use of catechin-based flavonoids in contexts in which they are not normally found, potentially providing increased consumption and/or exposure to the catechin-based flavonoids, thereby increasing the potential to receive the pharmacological benefit of these compounds.

SUMMARY OF THE INVENTION

In one aspect, there is provided a conjugate of a delivery agent containing a free aldehyde and a flavonoid, having the delivery agent conjugated at the C6 and/or the C8 position of the A ring of the flavonoid.

In another aspect, there is provided a delivery vehicle comprising the conjugate described herein.

In a further aspect, there is provided a method of conjugating a delivery agent having a free aldehyde group in the presence of acid to a flavonoid, comprising reacting the delivery agent with the flavonoid in the presence of an acid catalyst.

In yet a further aspect, a method of delivering a catechin-based flavonoid to a subject comprising administering to the subject the conjugate or the delivery vehicle described herein.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1A:
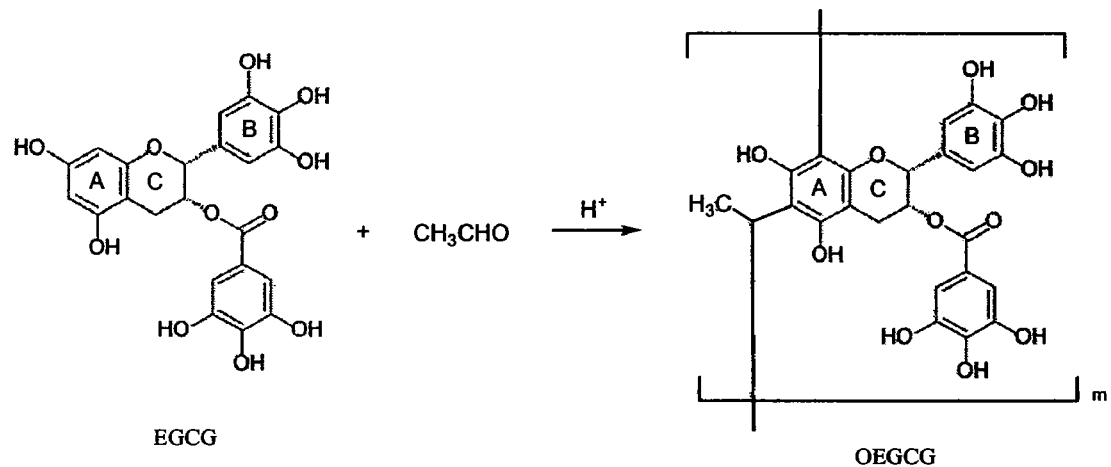
FIG. 1A is a schematic depiction of the oligomerization of (−)-epigallaocatechin gallate (EGCG) to yield oligomeric (−)-epigallaocatechin gallate (OEGCG)

It is generally desirable to find ways to readily increase the concentration of flavonoids in the body and to improve effective delivery of such flavonoids to various tissues in the body.

In order to increase the availability of beneficial flavonoid compounds, the inventors have found that conjugation of flavonoids to various delivery agents through a free aldehyde group on the delivery agent to the A ring of the flavonoid allows for modification of the physical properties of the flavonoid without disrupting the polyphenol structure of the flavonoid, while augmenting the biological and pharmacological properties of the flavonoid.

That is, the aldehyde-mediated conjugation of a delivery agent to the flavonoid results in attachment of the delivery agent at the C6 and/or C8 position of the flavonoid A ring, and does not disrupt or affect the B and C rings of the flavonoid or the various hydroxyl groups on the flavonoid.

Conjugation of a delivery agent to a flavonoid can provide a composition that is suitable for administration to a subject by incorporating the flavonoid into a particular vehicle formed with the delivery agent, and can allow for administration of higher concentrations of flavonoids than can be obtained through diet. The delivery agent can provide stability to the composition, resulting in a composition that is metabolized or degraded more slowly, and which thus may have a longer half-life in the body than the unconjugated flavonoid alone. For example, the delivery agent may be of such a nature that the flavonoid is incorporated into a composition that enhances the water-solubility of the flavonoid, which can avoid uptake by the reticuloendothelial system and subsequent clearance by the kidneys, resulting in a longer half-life in the body. Conjugation of other delivery agents may protect the flavonoid from enzyme degradation.

Thus, there is presently provided a method of conjugating a delivery agent to a flavonoid comprising reacting the delivery agent with the flavonoid in the presence of an acid catalyst, the delivery agent having a free aldehyde group, or a group that is able to be converted to a free aldehyde group in the presence of acid.

The flavonoid may be any flavonoid from the general class of molecules derived from a core phenylbenzyl pyrone structure, and includes flavones, isoflavones, flavanols, flavanones, flavan-3-ols, catechins, anthocyanidins and chalcones. In a particular embodiment the flavonoid is a catechin or a catechin-based flavonoid. A catechin, or a catechin-based flavonoid is any flavonoid that belongs to the class generally known as catechins (or flavan-3-ol derivatives), and includes catechin and catechin derivatives, including epicatechin, epigallocatechin, catechin, epicatechin gallate and epigallocatechin gallate, and including all possible stereoisomers of catechins or catechin-based flavonoids. In particular embodiments, the catechin-based flavonoid is (+)-catechin or (−)-epigallocatechin gallate. (−)-epigallocatechin gallate (EGCG) is thought to have the highest activity among the catechin-based flavonoids, possibly due to the trihydroxy B ring and gallate ester moiety at the C3 position of this flavonoid.

The delivery agent is any chemical group or moiety that contains a free aldehyde or group, or a functional group that can be converted to a free aldehyde group in the presence of acid, for example an acetal group. The delivery agent is capable of being formed into a delivery vehicle, thus allowing for the incorporation of a conjugated flavonoid into the delivery vehicle without compromising the biological or pharmacological properties of the flavonoid. As well, the delivery agent should be biocompatible, and may be biodegradable in some embodiments.

The following discussion refers to an embodiment in which the flavonoid is a catechin-based flavonoid and in which the delivery agent is a polymer. However, it will be understood that the aldehyde condensation reaction between an aldehyde-containing chemical group and a flavonoid is applicable to conjugation of any delivery agent having a free aldehyde group, including following acid treatment of the delivery agent, to any flavonoid, as described above.

Thus, in one embodiment the method involves conjugation of a polymer containing a free aldehyde group or a group that is able to be converted to a free aldehyde group in the presence of acid to a catechin-based flavonoid.

The catechin-based flavonoid may be a single monomeric unit of a catechin-based flavonoid or it may be an oligomer of one or more catechin-based flavonoids. As stated above, conjugation of a polymer to a flavonoid results in augmentation of the flavonoid's biological or pharmacological properties. As well, an oligomer of the catechin-based flavonoid tends to have amplified or augmented levels of the biological and pharmacological properties associated with catechin-based flavonoids, and may even have reduced pro-oxidant effects that are sometimes associated with monomeric catechin-based flavonoids. Thus, in one embodiment, the catechin-based flavonoid is an oligomerized catechin-based flavonoid having amplified or augmented flavonoid properties.

Oligomers of catechin-based flavonoids are known, including oligomers prepared through enzyme-catalyzed oxidative coupling and through aldehyde-mediated oligomerization. An aldehyde-mediated oligomerization process results in an unbranched oligomer that has defined linkages, for example through carbon-carbon linkages such as $CH-CH_3$ bridges linked from the C6 or C8 position on the A ring of one monomer to the C6 or C8 position on the A ring of the next monomer, including in either possible stereoconfiguration, where applicable. Thus, the $CH-CH_3$ linkage may between the C6 position of the A ring of one monomer and either of the C6 or C8 position of the next monomer or it may be between the C8 position of the A ring of the first monomer and either of the C6 or C8 position of the next monomer. For example, FIG. 1A depicts oligomeric (−)-epigallocatechin gallate (OEGCG) produced from an aldehyde-mediated oligomerization method, which is connected through C6-C8 linkages of (−)-epigallocatechin gallate monomers.

The oligomer of the catechin-based flavonoid may be of 2 or more monomeric units linked together. In certain embodiments, the catechin-based flavonoid oligomer has from 2 to 100 flavonoid monomer units, from 10 to 100, from 2 to 80, from 10 to 80, from 2 to 50, from 10 to 50, from 2 to 30, from 10 to 30, from 20 to 100, from 30 to 100 or from 50 to 100 monomeric units.

The polymer may be any polymer having a free aldehyde group prior to conjugation with the catechin-based flavonoid, or having a group that is converted to an aldehyde group in the presence of acid, for example an acetal group. Furthermore, it will be understood that the polymer should be non-toxic, biocompatible and suitable for pharmacological use. The polymer may also have other desirable properties, for example, the polymer may have low immunogenicity, and it may be biodegradable or non-biodegradable depending on the desired biological application of the composition, for example, for controlled release of catechin-based flavonoids or other bioactive agents at a particular site in a body.

The polymer may be chosen based on its particular characteristics and its ability to form certain types of delivery vehicles. For example, the polymer may be an aldehyde-terminated poly(ethylene glycol), or it may be hyaluronic acid derivatized with an aldehyde group, or a derivative of such polymers. Alternatively, the polymer may be a phenoxymethyl(methylhydrazono) dendrimer (PMMH), for example, cyclotriphosphazene core PMMH or thiophosphoryl core PMMH. The polymer may also be any biological polymer, modified to contain a free aldehyde group or a group that is convertible to an aldehyde in the presence of acid, for example an aldehyde-modified protein, peptide, polysaccharide or nucleic acid. In one particular embodiment the polymer is an aldehyde-terminated poly(ethylene glycol) (PEG-CHO). In another particular embodiment, the polymer is aldehyde-derivatized hyaluronic acid, hyaluronic acid conjugated with aminoacetylaldehyde diethylacetal, or either of the aforementioned hyaluronic acid polymers derivatized with tyramine.

The free aldehyde group on the polymer allows for the conjugation of the polymer in a controlled manner to either the C6 or the C8 position of the A ring, or both, of the flavonoid structure, thus preventing disruption of the flavonoid structure, particularly the B and C rings of the flavonoid, and thus preserving the beneficial biological and pharmacological properties of the flavonoid.

Figure 1B:
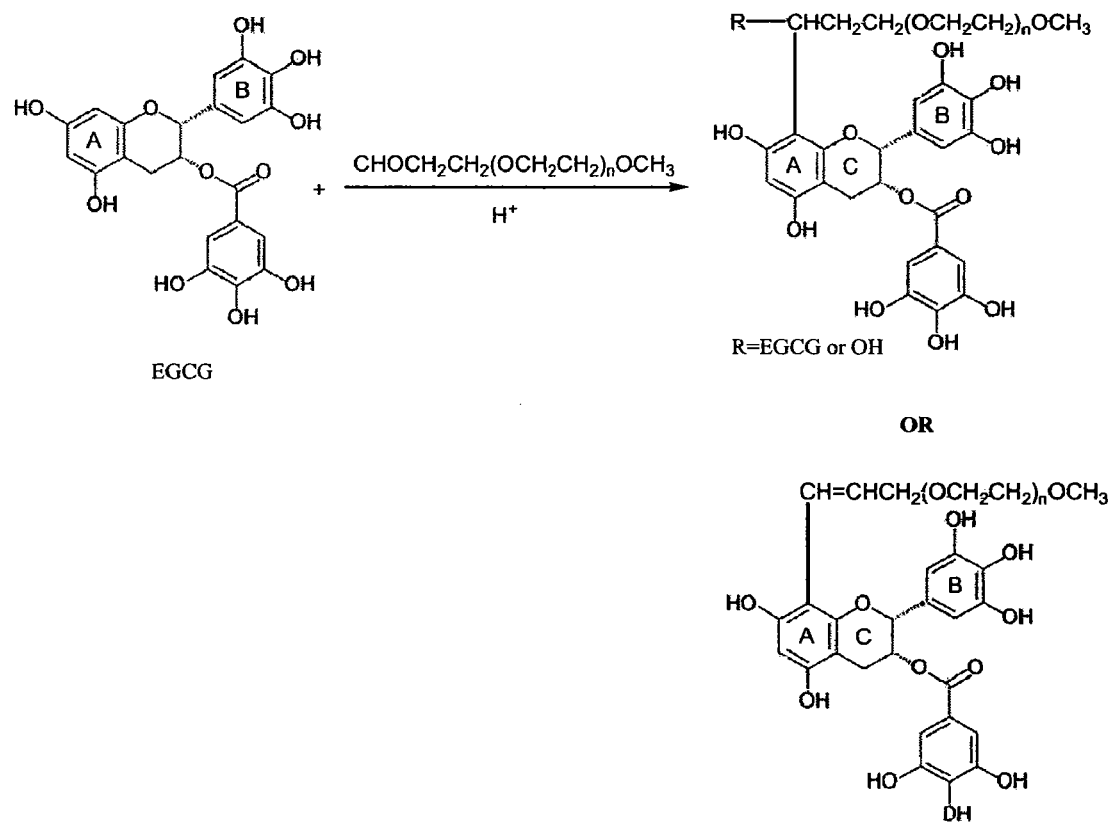
FIG. 1B is a schematic depiction of the conjugation of poly(ethylene glycol) (PEG) and EGCG to yield the PEG-epigallaocatechin gallate conjugate (PEG-EGCG)
Figure 1C:
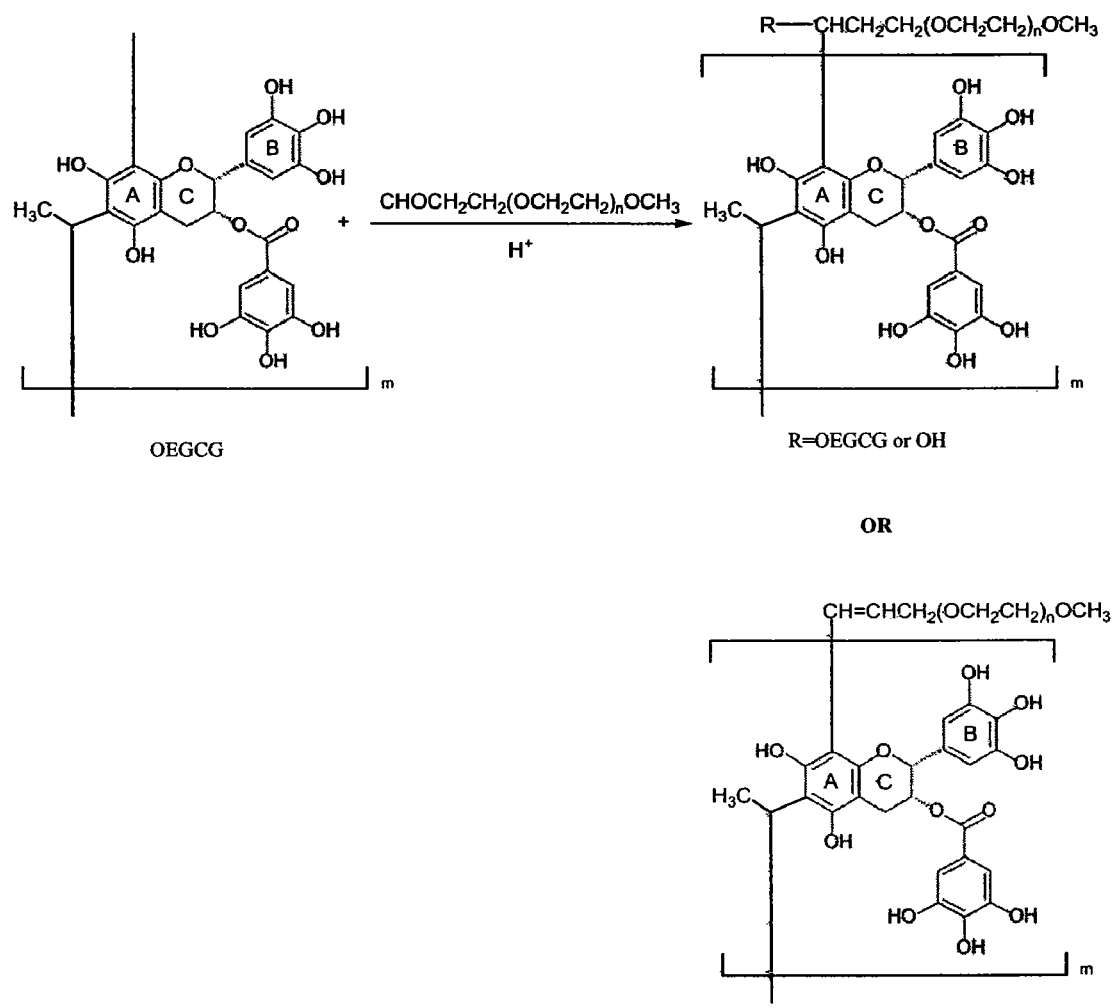
FIG. 1C is a schematic depiction of the conjugation of PEG and OEGCG to yield poly(ethylene glycol)-oligomeric epigallaocatechin gallate conjugate (PEG-OEGCG)

The polymer is conjugated to the catechin-based flavonoid via a reaction of the aldehyde group of the polymer with the C6 and/or the C8 position of the A ring of the catechin-based flavonoid, as shown in FIG. 1B and FIG. 1C.

The conjugate is synthesized using acid catalysis of a condensation of the aldehyde group of the polymer with the catechin-based flavonoid, or using acid to convert a functional group on the polymer to a free aldehyde prior to condensation of the aldehyde group with the catechin-based flavonoid.

To conjugate the polymer and the catechin-based flavonoid, the polymer and the catechin-based flavonoid may be separately dissolved in a suitable solvent. The polymer with the free aldehyde is added, for example by dropwise addition, to the solution containing the catechin-based flavonoid, in the presence of an acid. The reaction is allowed to go to completion. Following the conjugation reaction, excess unreacted polymer or catechin-based flavonoid can be removed from the conjugated composition, for example by dialysis or by molecular sieving.

The ratio of catechin-based flavonoid to polymer may be varied, so that there is only one polymer moiety attached to the catechin-based flavonoid portion of the polymer, or so that there is a catechin-based flavonoid portion attached at more than one position on the polymer, or so that the catechin-based flavonoid portion has two polymer portions attached, one at either of the C6 and C8 positions of the catechin-based flavonoid.

The ratio of polymer to catechin-based flavonoid in the final composition can be controlled through the ratio of starting reagents. For example, when the molar ratio of polymer moiety to catechin-based flavonoid moiety is about 1, a single polymer moiety will be attached to a single catechin-based flavonoid moiety (either monomeric or oligomeric may be used). However, at higher concentrations of polymer, for example at a 10:1 molar ratio of polymer to catechin-based flavonoid, a composition having a tri-block structure of polymer-flavonoid-polymer may be obtained.

A conjugate of a polymer containing a free aldehyde and a catechin-based flavonoid, having the polymer conjugated at the C6 and/or the C8 position of the A ring of the flavonoid is also contemplated.

Conjugation of the polymer also allows for the incorporation of catechin-based flavonoids into various compositions or vehicles. By selection of the particular polymer containing a free aldehyde group based on the physical properties of the polymer, it is possible to incorporate flavonoids into a variety of different vehicle types, allowing for the delivery of high concentrations of flavonoids in different contexts to various targeted areas of the body.

Thus, the present conjugate resulting from the above-described method may be formed into a delivery vehicle, depending on the nature of the polymer portion of the conjugate. The delivery vehicle may be used to deliver the catechin-based flavonoid to a body, including a particular targeted site in a body, depending on the nature of the delivery vehicle. Optionally, a bioactive agent may be included in the delivery vehicle, which may then be simultaneously delivered to the site in the body. Thus, there is provided a delivery vehicle comprising a composition that comprises a catechin-based flavonoid conjugated to a polymer through a free aldehyde group on the polymer, the delivery vehicle optionally further comprising a bioactive agent.

The bioactive agent may be any agent that has a biological, pharmacological or therapeutic effect in a body, and includes a protein, a nucleic acid, a small molecule or a drug. A bioactive agent that is a protein may be a peptide, an antibody, a hormone, an enzyme, a growth factor, or a cytokine. A bioactive agent that is a nucleic acid may be single stranded or double stranded DNA or RNA, a short hairpin RNA, an siRNA, or may comprise a gene encoding a therapeutic product. Also included in the scope of bioactive agent are antibiotics, chemotherapeutic agents and antihypertensive agents.

In one particular embodiment, the delivery vehicle is a micellar nanocomplex, which is suitable for parenteral delivery of catechin-based flavonoids, and optionally bioactive agents to a particular site within a body. The polymer is chosen to have properties that allow it to assemble with the catechin-based flavonoid portion of the composition, protecting the flavonoid from the solution environment. If a suitable solvent is chosen in which the polymer portion of the conjugate is soluble and is more soluble than the catechin-based flavonoid, the conjugate will self-assemble, excluding the solution from the flavonoid core, thus allowing for assembly of micellar complexes.

In a particular embodiment of the micellar nanocomplex delivery vehicle, the polymer chosen is aldehyde-terminated PEG, or a derivative thereof. PEG is a polymer widely used as a pharmacological ingredient, and possesses good hydrophilic, non-toxic, non-immunogenic and biocompatibility characteristics with low biodegradability.

By conjugating PEG-CHO to a catechin-based flavonoid, a conjugate is formed that has strong self-assembly tendencies. In one embodiment, PEG is conjugated to a monomer of a catechin-based flavonoid, to form a PEG-flavonoid. The delivery vehicle is formed together with non-conjugated catechin-based flavonoids, and optionally a bioactive agent. Thus, the central core contains relatively high concentrations of a flavonoid and the external shell of the micellar nanocomplex comprises the conjugated PEG-monomeric flavonoid, and is assembled in a two-step process. In a particular embodiment, the central core is oligomeric EGCG and the external core is made up of conjugated PEG-EGCG.

Formation of this two-step assembly of the delivery vehicle results in temporary partial or complete masking of the biological activities of the oligomeric flavonoid that is incorporated into the core of the delivery vehicle. For example, while assembled into core of the delivery vehicle, the augmented properties of the oligomerized EGCG are less available, due to physical interactions with other molecules in the assembled core portion of the delivery vehicle. Upon release from the delivery vehicle, for example by fusion of the vehicle with a cellular phospholipid membrane, the components of the delivery dissociate, unmasking the biological properties of the oligomeric catechin-based flavonoid.

Figure 2A:
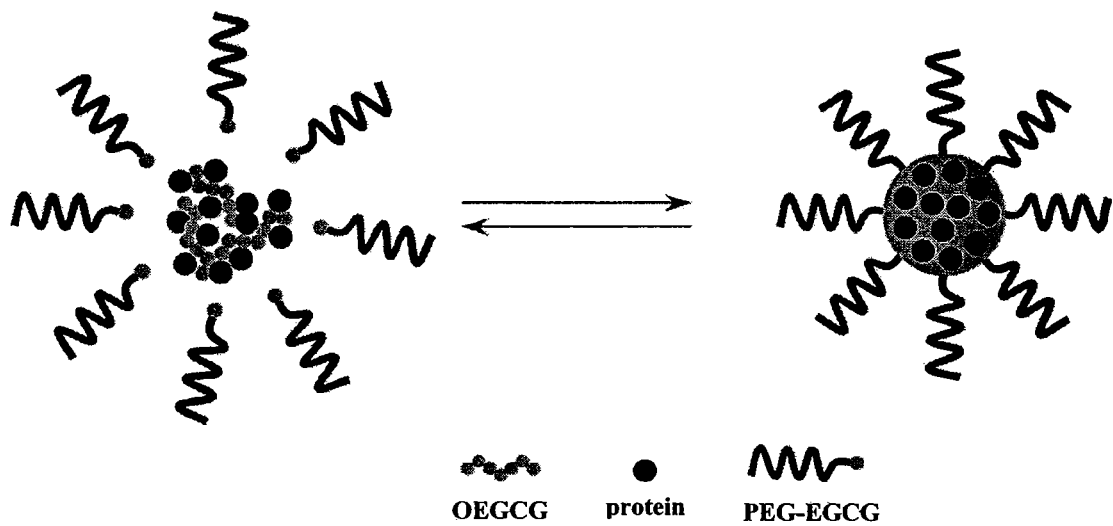
FIG. 2A is a schematic depiction of a micellar nanocomplex system comprising the self-assembled OEGCG/protein complex surrounded by PEG-EGCG.

This embodiment of the delivery vehicle is well suited to deliver bioactive agents. Since the catechin-based flavonoids have a rigid, multi-ring core structure, these molecules associate well with bioactive agents such as proteins and nucleic acids, as well as other molecules containing ring structures, likely by stacking of the catechin rings with the ring or rings on the bioactive agent. Thus, an oligomeric catechin-based flavonoid can be used to associate with the bioactive agent prior to assembly in the micellar nanocomplex, as shown in FIG. 2A.

The concentration of the bioactive agent is chosen depending on the total amount of bioactive agent that is to be delivered to a particular site in a body, and on the amount of bioactive agent that can be included in the micellar nanocomplex without destabilizing the micellar structure. In certain embodiments, up to 50%, or up to 40%, w/w of the micellar complex may comprise the bioactive agent.

The biological activity of the bioactive agent is also temporarily partially or completely masked while incorporated into the present delivery vehicles. As with the oligomeric catechin-based flavonoid, the biological properties of the bioactive agent are masked or sequestered, making them less available while the bioactive agent is assembled in the delivery vehicle, meaning that the bioactive agent is not able to exert bioactivity or interact with other molecules in a bioactive manner while contained in the delivery vehicle. Upon release of the bioactive agent from the delivery vehicle, the biological properties of the bioactive agent are once again available, and the bioactive agent is able to exert a biological effect.

Figure 2B:
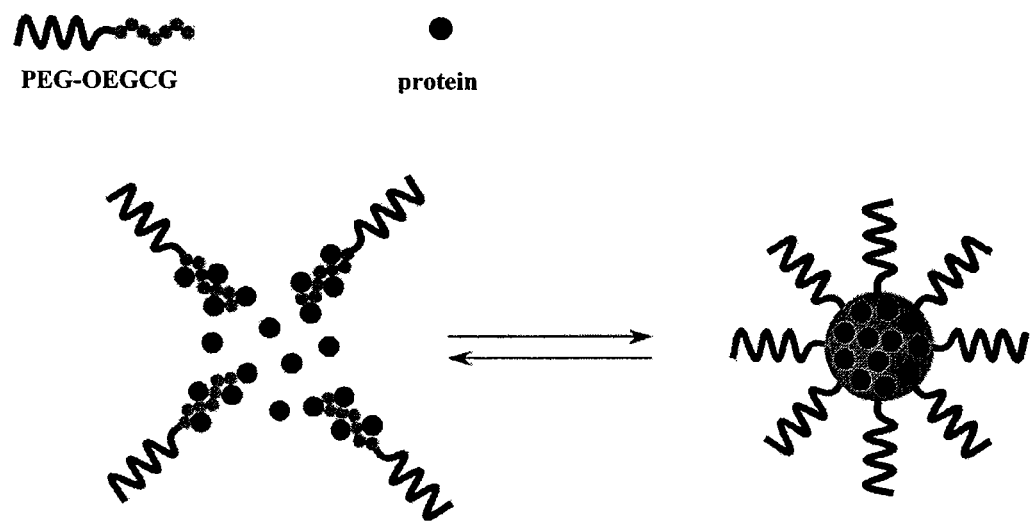
FIG. 2B is a schematic depiction of a micellar nanocomplex of a PEG-OEGCG/protein complex.

In another embodiment, PEG is conjugated to an oligomeric catechin-based flavonoid. This embodiment of the delivery agent has strong self-assembly properties and can be self-assembled in a single step process. As with the two-step assembly micellar nanocomplex above, the single-step assembling micellar nanocomplex may optionally include a bioactive agent. FIG. 2B describes a nanocomplex comprising PEG-OEGCG and a protein.

The above micellar nanocomplexes are of nanoscale dimensions, and may be from about 1 nm to about 10000 nm in diameter, or from about 20 nm to about 4000 nm in diameter, or from about 20 nm to about 100 nm in diameter. The size of the micellar nanocomplexes can be varied by varying the length of the oligomerized catechin-based flavonoid, the length of the polymer, and the concentration of unconjugated oligomerized catechin-based flavonoid. The size of the micellar nanocomplex may be pH dependent, depending on the polymer used. For example, in micellar nanocomplexes in which the conjugated polymer is PEG, the diameter of the micelles tends to decrease with increasing pH.

Generally, the micellar nanocomplexes undergo self assembly and thus little synthesis is required. For the two step process, the components that are to form the core are dissolved in a suitable solvent, for example in diluted DMSO or methanol, and are allowed to assemble. The solvent is a solvent in which the core components are soluble, and which may be miscible in water, or which may be volatile, or from which the assembled micelles can otherwise be isolated or extracted. As indicated above, the core components may be for example a bioactive agent and a catechin-based flavonoid, for example an oligomeric catechin-based flavonoid. The polymer-catechin-based flavonoid conjugate that is to form the outer shell is then added to the solution and the micellar complex is allowed to form.

For the one step self-assembly process, the polymer-catechin-based flavonoid conjugate, optionally with a bioactive agent, is dissolved in a suitable buffer as described for the two-step process and the micellar nanocomplex is allowed to assemble.

This micellar nanocomplex system provides the ability to achieve controlled biodistribution of catechin-based flavonoids and prolonged circulation half-life in bloodstream due to the PEG outer shell, as well as amplified pathological activities of the catechin-based flavonoid compound, with the added benefit that such compounds may be accompanied by therapeutic effect of an additional bioactive agent loaded in the inner core of the micelle. Where the bioactive agent is a sensitive molecule such as a protein, the nanoscale micelles offer a convenient delivery vehicle with the advantage of a gentle, self-assembly method that does not involve the mechanical, thermal and chemical stresses that can be associated with conventional encapsulation techniques currently used, which conventional techniques may lead to denaturation of sensitive bioactive agents such as proteins.

In another particular embodiment, the delivery vehicle is a hydrogel, which can be used as a wound or burn dressing, for sustained release delivery of a bioactive agent, as a support for tissue regeneration, for treatment of arthritis, or for cosmetic applications such as a facial mask.

The polymer is chosen to have good swellability characteristics and to have appropriate groups available for cross-linking of the polymer moieties, and to be non-toxic and biocompatible, and in some embodiments to be biodegradable.

In a particular embodiment of the hydrogel, the polymer is aldehyde derivatized hyaluronic acid, or a derivative of hyaluronic acid such as hyaluronic acid aminoacetylaldehyde diethylacetal conjugate, or a tyramine derivative of aldehyde-derivatized hyaluronic acid or hyaluronic acid aminoacetylaldehyde diethylacetal conjugate.

Conjugates comprising a hyaluronic acid-catechin-based flavonoid can be readily cross-linked to form a hydrogel, without disruption of the biological or pharmacological properties of the flavonoid. Such hydrogels may also optionally comprise a bioactive agent as described above, for release of the bioactive agent at the site where the hydrogel is applied.

The hyaluronic acid-flavonoid conjugate is synthesized by reacting the hyaluronic acid with the catechin-based flavonoid under acidic conditions, for example from about 1 to about 5, or for example at pH of about 1. The conjugated polymer-flavonoid is then purified, for example by dialysis, and then mixed with bioactive agent and a cross-linking agent, such as hydrogen peroxide. A cross-linking catalyst is added, for example horseradish peroxidase, and the hydrogel may then be quickly poured in to a mold to form a desired shape before the cross-linking reaction is completed. For example, the hydrogel may be formed into a slab suitable for application as a wound dressing.

The components of the hydrogel may also be injected and reacted to form the hydrogel in vivo, for example by injecting an uncrosslinked conjugate, optionally with a bioactive agent, together with a cross-linking agent, such as hydrogen peroxide and a cross-linking catalyst, for example, horseradish peroxidase. Such a hydrogel is useful for drug delivery to a specific site in a body, or for tissue engineering.

Since hyaluronic acid has multiple sites that may react with the flavonoid during the conjugation reaction, by varying the concentration of the catechin-based flavonoid in the starting reaction, it is possible to vary the degree of conjugation between the hyaluronic acid polymer and the catechin-based flavonoid. For example, the ratio of reactants may be adjusted so that the resulting conjugate has from about 1% to about 10% of the sites on the polymer conjugated with the flavonoid. Alternatively, additional hyaluronic acid that has not been conjugated can be added to the mixture prior to cross-linking of the hydrogel so that some of the polymer molecules in the hydrogel will not be conjugated to the flavonoid.

The above described compositions and delivery vehicles are well-suited for controlled and targeted delivery of catechin-based flavonoids to particular sites within the body. The flavonoids can provide antibacterial, antineoplastic, antithrombotic, vasodilatory, antioxidant, anti-mutagenic, anti-carcinogenic, hypercholesterolemic, antiviral and anti-inflammatory activity at the targeted site. Thus, the above conjugates and delivery vehicles are useful for a variety of treatment applications. In addition, the delivery vehicles can include an additional bioactive agent, making the delivery vehicles useful in the treatment of a wide range of disorders or diseases. For example, immunoregulatory peptides and proteins including cytokines and growth factors have emerged as an important class of drugs for the treatment of cancer, myelodepression and infectious disease.

Thus, there is presently provided a method of delivering a catechin-based flavonoid to a subject comprising administering a conjugate of a polymer containing a free aldehyde and a catechin-based flavonoid, having the polymer conjugated at the C6 and/or the C8 position of the A ring of the flavonoid is also contemplated, as described above. In certain embodiments, the conjugate is formed into a delivery vehicle, such as a micellar nanocomplex or a hydrogel, as described above.

The subject is any animal, including a human, in need of catechin-based flavonoids, and may be in further need of an additional bioactive agent.

The conjugate may be administered using known methods, which will depend on the form of the conjugate. Non-oral routes are preferred, particularly if a bioactive agent is being administered simultaneously in the same form with the conjugate. If the conjugate is formulated as a solution, or in the form of micellar nanoparticles, the conjugate may be delivered parenterally, including intravenously, intramuscularly, or by direct injection into a targeted tissue or organ. If the conjugate is formulated as a hydrogel, the conjugate may be applied topically or by surgical insertion at a wound site.

The conjugate may be administered in combination with a bioactive agent, particularly where the conjugate is formulated as a delivery vehicle as described above.

When administered to a patient, the conjugate is administered in an amount effective and at the dosages and for sufficient time period to achieve a desired result. For example, the conjugate may be administered in quantities and dosages necessary to deliver a catechin-based flavonoid which may function to alleviate, improve, mitigate, ameliorate, stabilize, prevent the spread of, slow or delay the progression of or cure an infection, disease or disorder, or to inhibit, reduce or impair the activity of a disease-related enzyme. A disease-related enzyme is an enzyme involved in a metabolic or biochemical pathway, which when the pathway is interrupted, or when regulatory control of the enzyme or pathway is interrupted or inhibited, the activity of the enzyme is involved in the onset or progression of a disease or disorder.

The effective amount of conjugate to be administered to a subject can vary depending on many factors such as the pharmacodynamic properties of the conjugate, including the polymer moiety and the catechin-based flavonoid moiety, the mode of administration, the age, health and weight of the subject, the nature and extent of the disorder or disease state, the frequency of the treatment and the type of concurrent treatment, if any, and the concentration and form of the conjugate.

One of skill in the art can determine the appropriate amount based on the above factors. The conjugate may be administered initially in a suitable amount that may be adjusted as required, depending on the clinical response of the subject. The effective amount of conjugate can be determined empirically and depends on the maximal amount of the conjugate that can be administered safely. However, the amount of conjugate administered should be the minimal amount that produces the desired result.

The invention is further illustrated by the following non-limiting examples.

EXAMPLES (−)-Epigallocatechin gallate (EGCG), a main ingredient of green tea, exhibits numerous biological and pharmacological effects. In the following examples, conjugates of poly(ethylene glycol) with EGCG or oligomeric EGCG (OEGCG) were synthesized using aldehyde-mediated condensation by an acid catalyst. The synthesized compounds were characterized with molecular weight, NMR spectra, phenolic analysis, UV-VIS spectra, DSC thermogram, and ζ-potential.

Example 1

Conjugation of polyethylene glycol with (−)-epigallocatechin gallate or with oligomeric (−)-epigallocatechin gallate In this study, we synthesized conjugates of poly(ethylene glycol) (PEG) with (−)-epigallocatechin gallate (EGCG) or oligomerized EGCG (OEGCG). PEG-EGCG or PEG-OEGCG conjugation using aldehyde-terminated PEG (PEG-CHO) was carried out by Baeyer acid-catalyzed condensation between an aldehyde moiety at the end of PEG chain and a nucleophilic phloroglucinol ring of the EGCG moiety (FIG. 1).

Materials: (−)-Epigallocatechin gallate (EGCG) was purchased from KURITA LTD., Japan. Aldehyde-terminated polyethylene glycol (PEG-CHO) was purchased from NOF Co., Japan. Acetic acid, acetaldehyde, PURPALD™, Folin-Ciocalteu phenol reagent, sodium carbonate, vanillin and dimethylsulfoxide-$d_6$ were purchased from Sigma-Aldrich. 1N sodium hydroxide was purchased from Wako Pure Chemical Industries, Japan. Other reagents and solvents are commercially available and used as received.

Synthesis of PEG-epigallocatechin gallate conjugate: PEG-CHO and EGCG were separately dissolved in a mixture of acetic acid/water/ethanol or acetic acid/water/DMSO. The molar ratio of EGCG was varied in excess to PEG-CHO. The reaction was started by dropwise addition of PEG-CHO solution and performed at 20° C. (pH from 1 to 5) under air or nitrogen atmosphere for varied reaction time. The resulting products were dialyzed (molecular weight cutoff: $3.5 \times 10^3$) against 1000 times the volume of methanol at room temperature for two days. The dialysate was replaced to distilled water six times and the remaining solution was lyophilized to give the conjugates of PEG and (−)-epigallocatechin gallate, or PEG-EGCG.

$^1$H NMR (DMSO-$d_6$): δ 2.6-3.0 (H-4 of C ring), 3.2-3.7 (CH$_3$O and CH$_2$CH$_2$O of PEG), 4.9-5.0 (H-2 of C ring), 5.5 (H-3 of C ring), 5.8-6.0 (H-6 and 8 of A ring), 6.3-6.5 (H-2" and 6" of galloyl moiety), 6.7-6.9 (H-2' and 6' of B ring).

$^{13}$C NMR (DMSO-$d_6$): δ 31.5 (C-4 of C ring), 47.8-49 (CH$_2$CHO of PEG), 58.9 (CH$_3$O of PEG), 70.7-72.1 (CH$_2$CH$_2$O of PEG), 106.3-106.4 (C-2' and 6' of B ring), 109.5 (C-2" and 6" of galloyl moiety), 146.2-146.4 (C-3' and 5' of B ring and C-3" and 5" of galloyl moiety).

Synthesis of oligomeric epigallocatechin gallate: EGCG was dissolved in a mixture of acetic acid/water/DMSO or acetic acid/water/ethanol. The reaction was started by addition of acetaldehyde and performed at 20° C. (pH from 1 to 5) under air or a nitrogen atmosphere for varied reaction time. The resulting products were dialyzed (molecular weight cutoff: $1 \times 10^3$) in a same way described above. The remaining solution was lyophilized to give oligomeric epigallocatechin gallate (OEGCG).

$^1$H NMR (DMSO-$d_6$): δ 1.1-1.9 (CHCH$_3$), 2.6-3.1 (H-4 of C ring), 3.0-3.5 (H-3 of C ring), 4.9-5.1 (H-2 of C ring), 5.1-5.4 (CHCH$_3$), 6.4-6.5 (H-2" and 6" of galloyl moiety), 6.8-6.9 (H-2' and 6' of B ring).

$^{13}$C NMR (DMSO-$d_6$): δ 15.6-19 (CHCH$_3$), 19-24 (CHCH$_3$), 26.6-27.4 (C-4 of C ring), 68.5-68.6 (C-3 of C-ring), 77.3-77.4 (C-2 of C ring), 106.2-106.3 (C-2' and 6' of B ring), 109.5-109.6 (C-2" and 6" of galloyl moiety), 120.0-120.1 (C-1" of galloyl moiety), 129.3-129.5 (C-4c of A ring), 133.1-133.2 (C-1' of B ring), 139.4 (C-4' of B ring and C-4" of galloyl moiety), 146.2-146.5 (C-3' and 5' of B ring and C-3" and 5" of galloyl moiety), 150-158 (C-5, 7 and 8b of A ring), 166 (C-a of galloyl moiety).

Synthesis of PEG-oligomeric epigallocatechin gallate: PEG-CHO was dissolved in a mixture of acetic acid/water/ethanol or acetic acid/water/DMSO. OEGCG was dissolved in a same solvent with various molar ratios (0.1-1) to those of PEG-CHO. The solution of PEG-CHO was added dropwise and the reaction was carried out at 20-50° C. (pH from 1 to 5) under air or nitrogen atmosphere for varied reaction time. The resulting opaque products were dialyzed (molecular weight cutoff: 5000) in a same way described above. After centrifugation (rpm=3.5×10$^4$) the precipitate was collected and washed by distilled water in triplicate, followed by lyophilization to give the conjugate of PEG and oligomeric (−)-epigallocatechin gallate (PEG-OEGCG).

$^1$H NMR (DMSO-d$_6$): δ 1.1-1.5 (CHCH$_3$), 2.6-3.1 (H-4 of C ring), 3.2-3.7 (CH$_3$O and CH$_2$CH$_2$O of PEG), 4.9-5.0 (H-2 of C ring), 5.1-5.4 (CHCH$_3$), 6.4-6.5 (H-2" and 6" of galloyl moiety), 6.8-6.9 (H-2' and 6' of B ring).

$^{13}$C NMR (DMSO-d$_6$): δ 70.7-72.2 (CH$_2$CH$_2$O of PEG), 77.3-77.4 (C-2 of C ring), 106.2-106.4 (C-2' and 6' of B ring), 109.5-109.6 (C-2" and 6" of galloyl moiety), 120.0-120.1 (C-1" of galloyl moiety), 129.3-129.5 (C-4c of A ring), 133.1-133.2 (C-1' of B ring), 139.4 (C-4' of B ring and C-4" of galloyl moiety), 146.2-146.5 (C-3' and 5' of B ring and C-3" and 5" of galloyl moiety), 150-158 (C-5, 7 and 8b of A ring), 166 (C-a of galloyl moiety).

Measurements: Molecular weight was estimated by size exclusion chromatography (SEC) (Waters 2690 equipped with RI-2410 detector, polystyrene standard) with Waters Styragel HR4E/HR5E columns using THF as an eluant at a flow rate of 1 ml/min at 40° C., after acetylation. $^1$H and $^{13}$C NMR were recorded on a Bruker 400-MHz nuclear magnetic resonance (NMR) spectrometer.

The aldehyde moiety of unreacted PEG-CHO was quantitatively assessed using 4-amino-3-hydrazino-5-mercapto-1,2,4-triazole (PURPALD™) which is exceedingly specific and sensitive to aldehydes and which yields purple-to-magenta-colored 6-mercatriazolo-[4,3-b]-s-tetrazines.[31,32] 100 μl of a sample solution was dropped into 3 ml of the PURPALD™ solution (7.5 mg/ml 1N NaOH). After aeration at room temperature, the absorption maxima of the solutions were recorded at 545 nm using UV-VIS spectrometer (JASCO V-510 UV/VIS/NIR spectrometer, Japan). Since the PURPALD™ is sensitive to even a small amount of aldehyde present in air, and resultantly produces a color reaction, a negative control in air was measured and subtracted from the values. Unreacted PEG-CHO was determined using PEG-CHO standard curve. The results of this PURPALD™ assay were compared to that of NMR measurement.

Phenolic content of conjugates was assessed by Folin-Ciocalteu assay and vanillin-HCl assay. Folin-Ciocalteu assay has been used for total phenolics determination by many researchers (Julkunen-tiitto R. *J. Agric. Food Chem.* 33, 21-217 (1985)). 15 μl of sample was added to 300 μl of water. 150 μl of Folin-Ciocalteu phenol reagent was added and the solution was vigorously shaken. Immediately, 750 μl of 20% sodium carbonate solution was added and the mixture was made up to 1.5 ml with water, following shaking again. After 20 min the absorptivity of the mixture was read at 720 nm using a UV-VIS spectrometer. Vanillin-HCl method has been used for catechins and condensed tannin determination (Broadhurst R. B. and Jones W. T. *J. Sci. Food Afric.* 29, 788-794 (1978)). For this assay, 100 μl of a sample was added to 1 ml of 4% vanillin in methanol and the mixture was shaken vigorously. 0.5 ml of concentrated HCl was added then, and the mixture was immediately shaken again. The absorptivity was read at 500 nm after keeping the mixture at room temperature for 20 min. The phenolic content of synthesized compounds using these two assays was determined using EGCG standard curves measured in the same manners. Each measurement was run in triplicate.

The melting temperatures (T$_m$) of products were measured with DSCQ100 TA Instruments. The measurements were calibrated using indium and carried out at temperatures from −40 to 200° C. under nitrogen purge at a scanning rate of 20° C./min. ζ-potential of sample solutions was determined by ZetaPALS Zeta Potential Analyzer (BROOKHAVEN INSTRUMENTS Co.) at 25° C. Each measurement was run in triplicate.

Aldehyde-mediated conjugation between polyethylene glycol and (−)-epigallocatechin gallate or oligomerized (−)-epigallocatechin gallate: In this study, conjugation of polyethylene glycol (PEG) with EGCG or oligomeric EGCG (OEGCG) was carried out using an aldehyde-mediated condensation by an acid catalyst. Synthesis of OEGCG is summarized in Table 1. The reaction was carried out with an excess of acetaldehyde under varied reaction conditions. Oligomers were obtained with several thousands molecular weight after purification by dialysis (MWCO=1000). The molecular weight was measured by SEC after acetylation since interaction between the many hydroxyl groups present on the EGCG units and the SEC column results in a lower estimation of molecular weight. Both molecular weight and yields were not affected by reaction time but were very affected by solvents and reaction atmosphere: both the molecular weight and yields were higher in the dimethylsulfoxide (DMSO) and water mixture than the ethanol and water mixture, although an increase in the amount of water in the solvent mixture decreased molecular weight and yield. The reaction in N$_2$ atmosphere produced higher molecular weight and yields, maybe due to O$_2$ in air terminating the oligomerization of EGCG. Resulting oligomers were also soluble in good solvents for EGCG, such as DMSO, N,N-dimethylformamide, acetone, ethanol, methanol, tetrahydrofuran and an alkaline aqueous solution except for water, and not soluble in chloroform and hexane in which neither was EGCG.

$^1$H and $^{13}$C NMR analysis of the product revealed that condensation of EGCG in the presence of acetaldehyde gave EGCG oligomers linked through a CH—CH$_3$ bridge at the C6 and C8 position of the phloroglucinol ring (A ring) (FIG. 1). Singlet peaks due to H6 and H8 of A ring observed at δ $^1$H 5.83 and 5.93 disappeared after oligomerization, and new peaks due to the methyl and methine protons of the CH—CH$_3$ bridge appeared at δ $^1$H 1.48 and 5.08 (δ $^{13}$C 21.2 and 16.2), respectively. All peaks for OEGCG were broadened and have lower intensity compared with those for EGCG.

Conjugation of PEG with EGCG and OEGCG was summarized in Table 2 and Table 3, respectively. After PEG-EGCG conjugation was carried out, unreacted EGCG was removed by dialysis (MWCO=3.5×10$^3$). In order to completely consume PEG-CHO, an excess amount of EGCG was fed into the reactor. When EGCG was fed with a 20 times larger molar amount than that of PEG-CHO in a N$_2$ atmosphere, the product was shown to contain no unreacted PEG-CHO, as analyzed by NMR (δ 9.65 (s, CHO)) and spectrophotometric assay using PURPALD™.

The molecular weight of conjugates showed that only one chain of PEG-CHO was conjugated to the EGCG, even though EGCG has two available link positions for aldehyde at C6 and C8 (Table 2). This may be due to steric hindrance following the conjugation of a single PEG chain at either of the C6 and C8 positions of A ring. However, PEG-OEGCG conjugates were obtained as both bi- and tri-block conjugates (PEG-OEGCG and PEG-OEGCG-PEG), when PEG-CHO was fed with a ten times lager molar amount than that of OEGCG (Table 3). By feeding with same molar ratio of OEGCG and PEG-CHO, the conjugation produced bi-block conjugate alone without tri-block conjugate.

The reaction in DMSO and a $N_2$ atmosphere resulted in high yields, as in the case of EGCG oligomerization mentioned above. All PEG-OEGCG conjugates were not water soluble including a conjugate of longer chain PEG with Mn=10000, while all of PEG-EGCG conjugates were water soluble. PEG-OEGCG was separated by centrifugation of an opaque aqueous solution after unreacted OEGCG was removed by dialysis against methanol. NMR analysis revealed that the supernatant was unreacted PEG-CHO and the precipitate was PEG-OEGCG conjugates. $^1$H and $^{13}$C NMR spectra of PEG-EGCG conjugate exhibited all intrinsic peaks belonged to PEG and EGCG, and the spectra of PEG-OEGCG also showed broadened peaks for OEGCG including $CHCH_3$ bridges as well as for PEG (FIG. 1).

Phenolic determination of conjugates: The EGCG moiety content of PEG-EGCG and PEG-OEGCG conjugates was assessed using vanillin and Folin-Ciocalteau assays which are commonly used for phenolic quantification in plant material. Folin-Ciocalteau assay is a protein determination method used for detecting tyrosine, tryptophan and cysteine residue of proteins (Folin O. and Ciocalteu. U. *J. Biol. Chem.* 73, 62-650 (1927)). This assay is nonspecific for phenol groups and also reacts with urea, chitosan and guanine to yield deep blue compounds. Vanillin-concentrated HCl assay (Broadhurst R. B. and Jones W. T. *J. Sci. Food Afric.* 29, 788-794 (1978)) is frequently used to detect catechins and procyanidins (condensed tannin). Standard curves were prepared using EGCG. All the standards tested in both assays showed a linear relationship between absorptivity and standard concentration varying in a range from 125 µM to 4 mM and from 62.5 µM to 2 mM for Folin-Ciocalteau and vanillin assay, respectively. The vanillin assay for PEG-EGCG and PEG-OEGCG solutions was quite reproducible and gave nearly same amount as the concentrations that were calculated based on their molecular weight. However, the Folin-Ciocalteau assay yielded 48.3±18.9% and 126.5±43.2% higher concentrations than the concentrations calculated based on molecular weight for PEG-EGCG and PEG-OEGCG, respectively.

Figure 3:
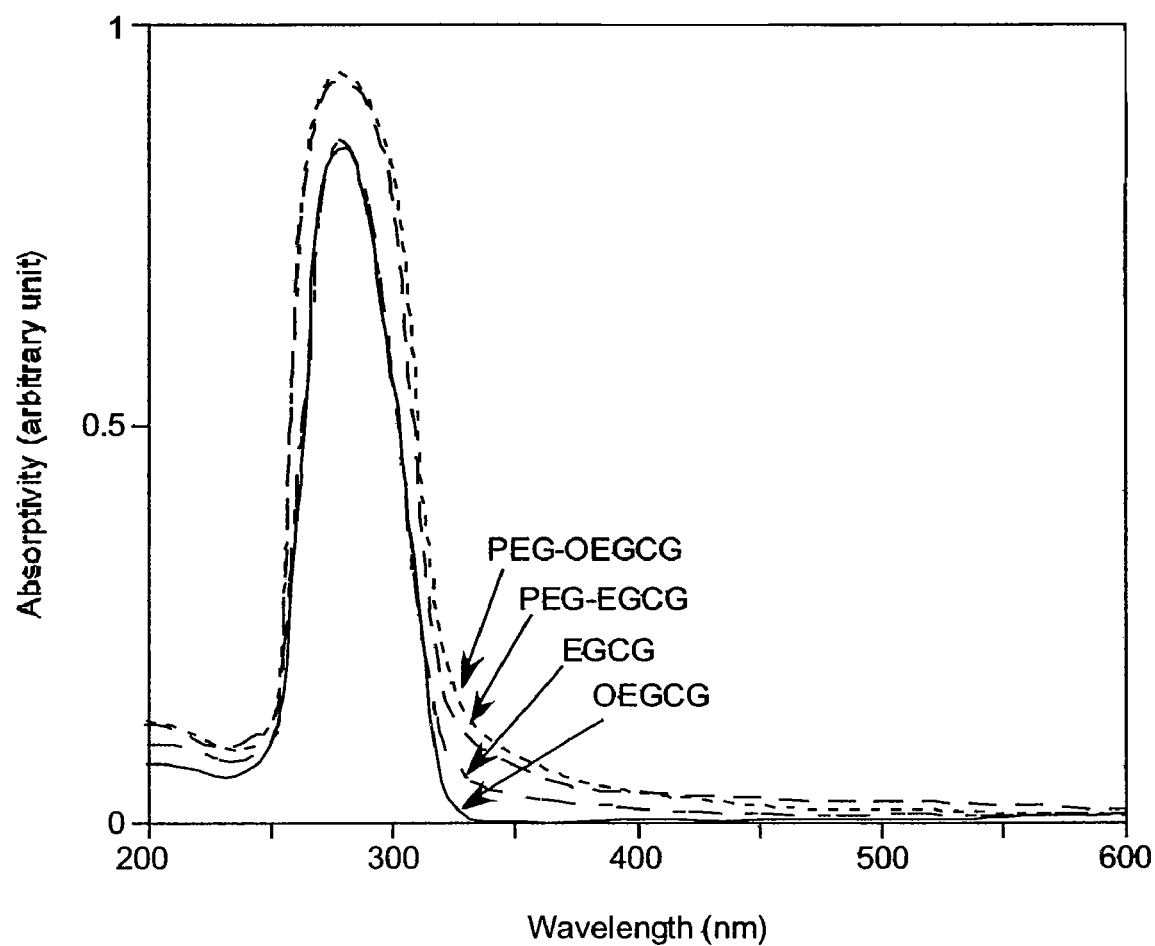
FIG. 3 is UV-VIS spectra of EGCG, OEGCG, PEG-EGCG, and PEG-OEGCG in an aqueous solution.

Optical property: FIG. 3 depicts the UV-VIS spectra of OEGCG, PEG-EGCG and PEG-OEGCG. These compounds were characterized in a manner similar to that of the precursors. EGCG showed an absorption maximum at 280 nm, indicating that the original flavanic skeleton is retained. In addition, we found that polymerized (+)-catechin by oxidative coupling using enzyme catalysts showed another absorption maxima at 388 nm in addition to that at 280 nm, giving a complicated structure, while (+)-catechin condensed through a $CH—CH_3$ bridge showed absorption maximum only at 280 nm. Therefore, the UV-VIS spectra of the present OEGCG, PEG-EGCG and PEG-OEGCG were considered further evidence for their structure shown by NMR as described above.

Figure 4:
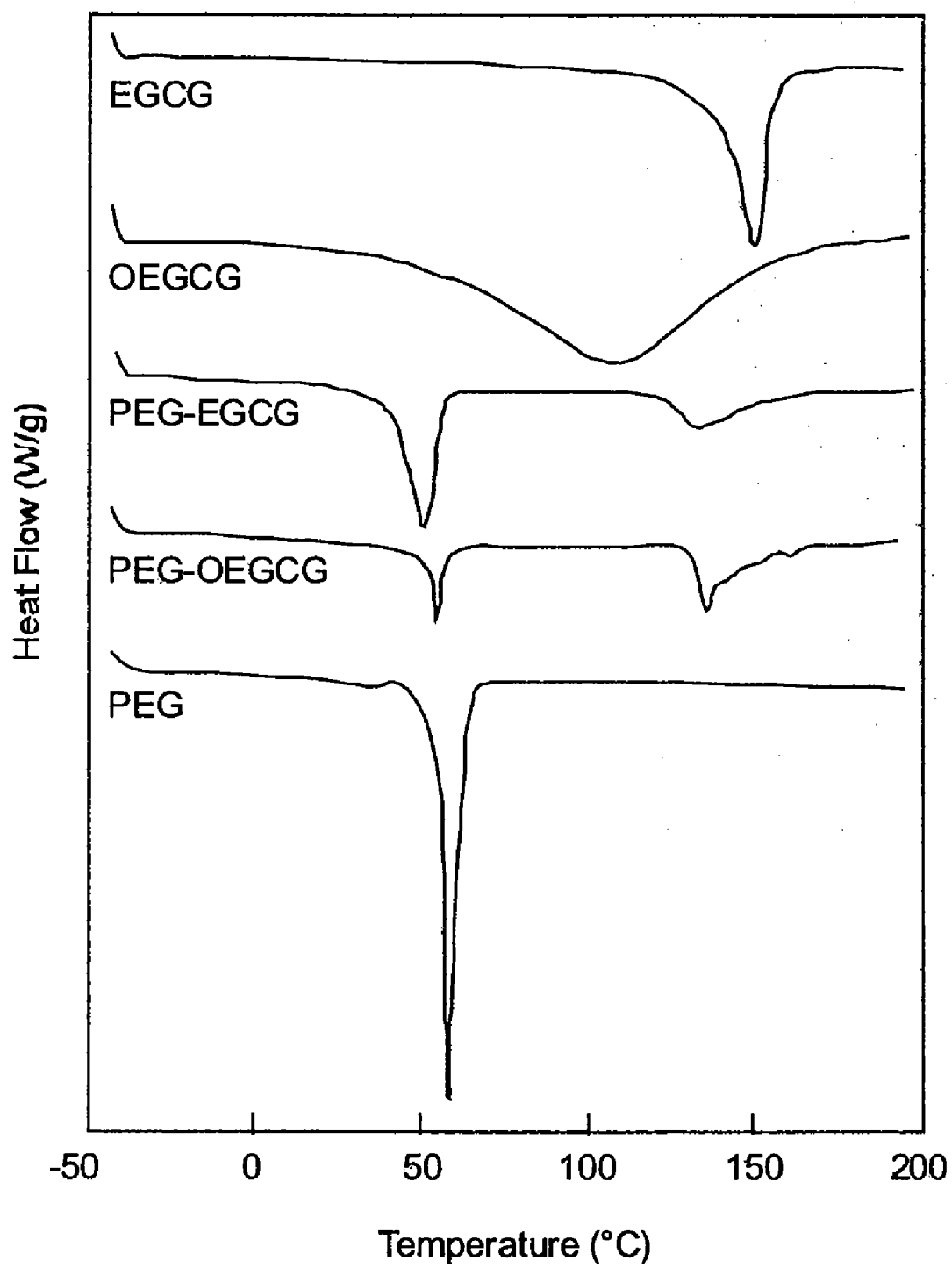
FIG. 4 is a DSC thermodiagram for EGCG, OEGCG, PEG-EGCG, PEG-OEGCG, and PEG.
Figure 5:
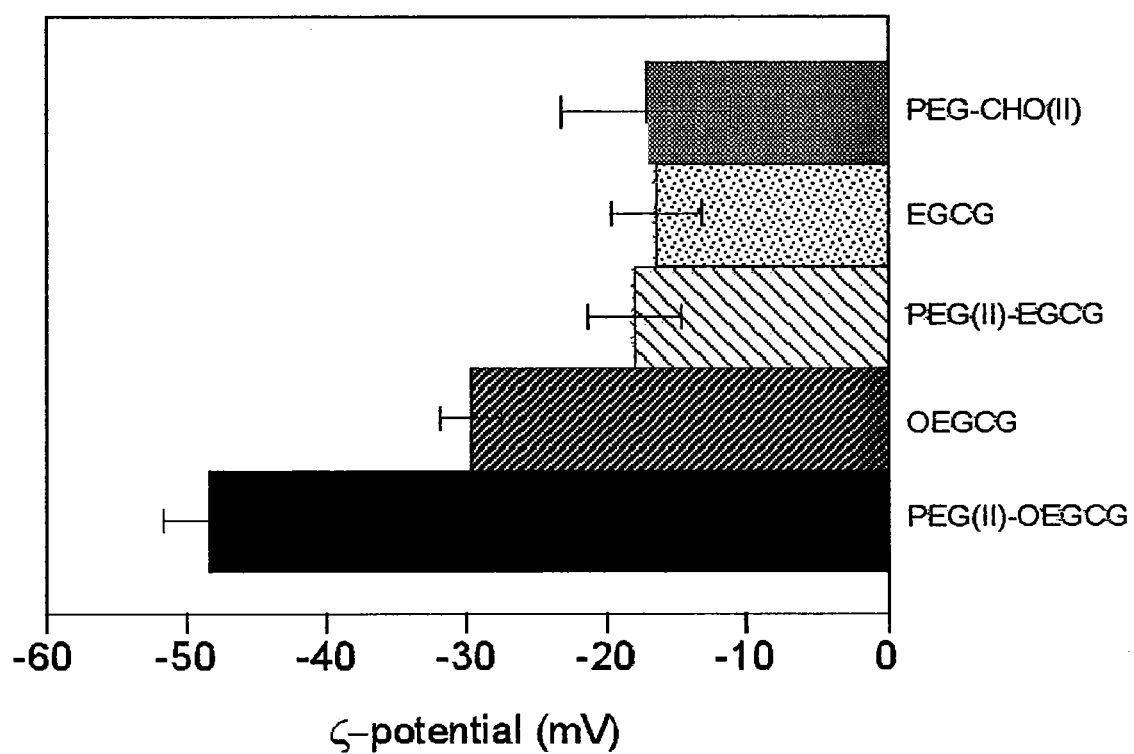
FIG. 5 is plot of ζ-potential of PEG, EGCG, PEG-EGCG, OEGCG, and PEG-OEGCG in PBS.

Thermal property: Thermal property of OEGCG, PEG-EGCG and PEGC-OEGCG was characterized by DSC measurement (FIG. 4). Endotherm peaks which correspond to the melting point ($T_m$) of PEG and EGCG were observed at 62.0 and 150.5° C., respectively. OEGCG showed a broadened Tm peak shifted to lower temperature compared to EGCG, reflecting a decrease in crystallinity. The DSC thermograms of PEG-EGCG and PEG-OEGCG had bimodal peaks corresponding to PEG and EGCG or OEGCG. $T_m$s originating from PEG were also shifted to lower temperature and the heat capacity of PEG in melting ($\Delta H_{T_m}$) became smaller, with a 26% and 73% decrease when conjugated with EGCG and OEGCG, respectively. These data indicate that the conjugation and oligomerization occurred as described.

ζ-potential: ζ-potential of the oligomers and conjugates were measured in PBS (FIG. 5). PEG and EGCG exhibited a slightly negative surface charge having similar values, and the PEG-EGCG conjugate showed no difference in charge compared to EGCG. On the other hand, OEGCG revealed a more negative charge than that of EGCG and the conjugation of OEGCG with PEG resulted in an apparently stronger negative charge than both PEG-EGCG and OEGCG.

Example 2

Augmentation of Physiological Activity of (−)-epigallocatechin gallate by oligomerization and Conjugation with PEG Materials: (−)-Epigallocatechin gallate (EGCG) was purchased from KURITA LTD., Japan. Aldehyde-terminated polyethylene glycol (PEG-CHO) was purchased from NOF Co., Japan. Acetic acid, acetaldehyde, dimethylsulfoxide-$d_6$, 1,1-diphenyl-2-picryl-hydrazyl (DPPH), Xanthine, Xanthine oxidase (XO), nitroblue tetrazolium (NBT), 2-amino-2-hydroxymethyl-1,3-propanediol (Tris) and polyethylene glycol (PEG) 8000 were purchased from Sigma-Aldrich. Urokinase (uPA) and SPECTROZYME™ UK were purchased from American Diagnostica Inc. Other reagents and solvents are commercially available and used as received.

Synthesis of OEGCG, PEG-EGCG or PEG-OEGCG: Oligomeric EGCG (OEGCG) and poly(ethylene glycol) conjugates with EGCG (PEG-EGCG) or OEGCG (PEG-OEGCG) were synthesized as described above. For OEGCG synthesis, EGCG was dissolved in a mixture of acetic acid/water/DMSO. The reaction was started by addition of acetaldehyde and performed at 20° C. (pH from 1 to 5) under a nitrogen atmosphere for 24 hr. The resulting products were dialyzed (molecular weight cutoff: $1 \times 10^3$) against 1000 times the volume of methanol at room temperature for two days, and then the remaining solution was lyophilized to give OEGCG. For conjugates synthesis, PEG-CHOs and EGCG or OEGCG were separately dissolved in a mixture of acetic acid/water/DMSO. The reaction was started by dropwise addition of PEG-CHO solution and performed at 20° C. (pH from 1 to 5) under a nitrogen atmosphere for 24 hr. The resulting products were dialyzed in a same way described above (molecular weight cutoff: $3.5 \times 10^3$). The PEG-EGCG and conjugate was obtained by lyophilization of dialyzed remaining solution. The PEG-OEGCG conjugate was precipitated by centrifugation (rpm=$3.5 \times 10^4$) before dialysis (molecular weight cutoff: 5000) and then lyophilized. The molecular weight was estimated by size exclusion chromatography (Waters 2690 equipped with RI-2410 detector, polystyrene standard) with Waters Styragel HR4E/HR5E columns using THF as an eluent at a flow rate of 1 ml/min at 40° C., after actetylation. $^1$H and $^{13}$C NMR were recorded on a Bruker 400-MHz nuclear magnetic resonance (NMR) spectrometer.

Diphenyl-picryl-hydrazyl scavenging activity: Different amounts of a sample were mixed with the chemically stable free radical 1,1-diphenyl-2-picryl-hydrazyl (DPPH) solution and absorbance at 519 nm was continuously recorded for 30 min at 25° C. using a UV-visible spectrophotometer (JASCO V-510 UV/VIS/NIR spectrometer, Japan). All analyses were run in triplicate and the results were averaged.

Superoxide anion scavenging activity: Superoxide anion was generated using xanthine and xanthine oxidase (XO), and measured by the nitroblue tetrazolium (NBT) reduction method. A test sample was mixed in a buffer solution (pH 7.0)

containing xanthine and NBT at 25° C. Measurement began with the addition of XO. Production of superoxide anion was followed spectrophotometrically at 560 nm for 10 min at 25° C. using a UV-visible spectrophotometer. All analyses were run in triplicate and the results were averaged. Superoxide scavenging activity was calculated according to the following formula:

Superoxide scavenging activity(%) =
$$\frac{absorbance_{control} - absorbance_{sample}}{absorbance_{control}} \times 100$$

Xanthine oxidase inhibitory activity: The activity of XO was measured spectrophotometrically by monitoring the formation of uric acid at 295 nm for 30 min using a UV-visible spectrometer. The assay was carried out under the same conditions as the superoxide anion assay, and the percentage activity was calculated.

uPA inhibitory activity: Various amounts of a sample were mixed with uPA in a buffer solution, and incubated for 15 min at 37° C. The mixture solution was added with SPECTROZYME™ and absorbance at 405 nm was recorded for 10 min using a microplate reader.

Results: Oligomerized (−)-epigallocatechin gallate (OEGCG) and conjugates of poly(ethylene glycol) with EGCG (PEG-EGCG) or the oligomer (PEG-OEGCG) were synthesized by the aldehyde-mediated condensation described above. The molecular weights estimated by size exclusion chromatography after acetylation, were Mw=4000, Mw/Mn=1.2; Mw=7900, Mw/Mn=1.2; and Mw=10100, Mw/Mn=1.1 for OEGCG, PEG-EGCG, and PEG-OEGCG, respectively.

Figure 6:
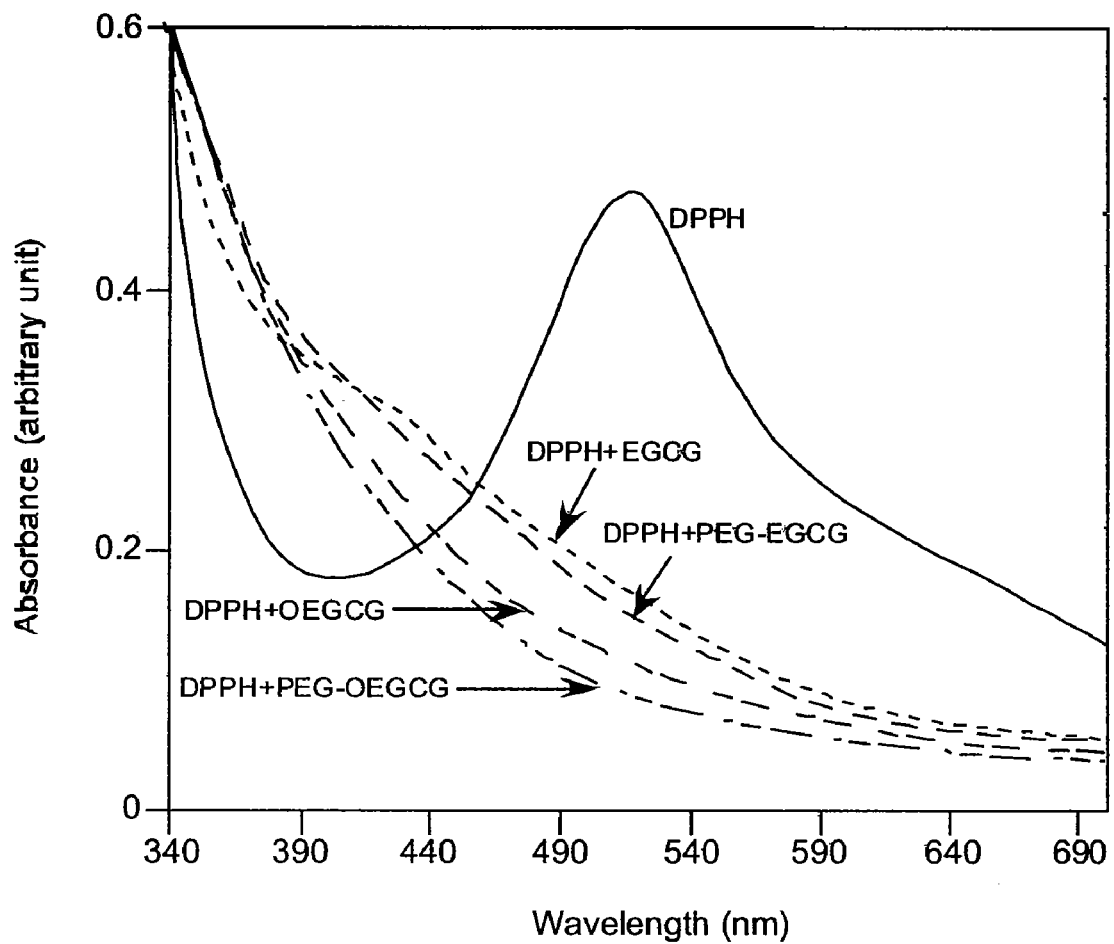
FIG. 6 is UV-VIS spectra of DPPH solutions treated with EGCG, OEGCG, PEG-EGCG, and PEG-OEGCG, measured at 519 nm.

Diphenyl-picryl-hydrazyl scavenging activity and Superoxide anion scavenging activity: The 1,1-diphenyl-2-picryl-hydrazyl radical (DPPH) assay, which measures hydrogen atom donating activity, provides an evaluation of antioxidant activity due to free radical scavenging. DPPH, a purple-coloured stable free radical, is reduced into the yellow-coloured diphenylpicryl hydrazine, as the radical is scavenged by antioxidants through donation of hydrogen. The compound capable of DPPH scavenging shows decreased absorbance at 519 nm as an indication of free radical scavenging activity. Addition of sample solutions showed significantly decreased absorbance maxima at 519 nm in all cases of OEGCG, PEG-EGCG and PEG-OEGCG (FIG. 6). The DPPH scavenging activity of samples was expressed by $IC_{50}$ (the concentration needed to scavenge DPPH by 50%), as shown in Table 4. The concentration-dependent free radical scavenging activities of OEGCG, PEG-EGCG and PEG-OEGCG were amplified, compared to the $IC_{50}$ observed for intact EGCG. These activities were also much higher than those of commercial antioxidants, vitamin C and dibutylhydroxytoluen (BHT).

A mixture of xanthine and XO generates superoxide anion, which reduces nitroblue tetrazolium (NBT) to give the blue chromogen formazan and increases UV absorbance at 560 nm. Compounds capable of scavenging superoxide anion, such as superoxide dismutase (SOD), inhibit NBT reduction. We found amplified concentration-dependent SOD-like activity than that observed for intact EGCG with lower $IC_{50}$ (the concentration needed to scavenge superoxide anion by 50%) in the case of PEG-EGCG, PEG-OEGCG and OEGCG, indicating that these compounds are more potent scavengers against superoxide anion than unmodified EGCG. Since compounds capable of scavenging superoxide anion can also affect NBT reduction, samples were investigated for their effects on these processes. A control experiment revealed that the samples did not directly reduce NBT in the range of concentrations tested. Evaluation of scavenging activity against DPPH and superoxide anion provided direct evidence of the free radical scavenging potential of those compounds. The results of the DPPH and superoxide anion assays indicated that the antioxidant activity was amplified on an EGCG unit-basis by the oligomerization and/or PEG conjugation of EGCG. These results imply that a single constituent EGCG unit within any of the oligomers and conjugates (OEGCG, PEG-EGCG or PEG-OEGCG) has a more potent scavenging activity than that of one EGCG unit alone in non-modified form.

Figure 7:
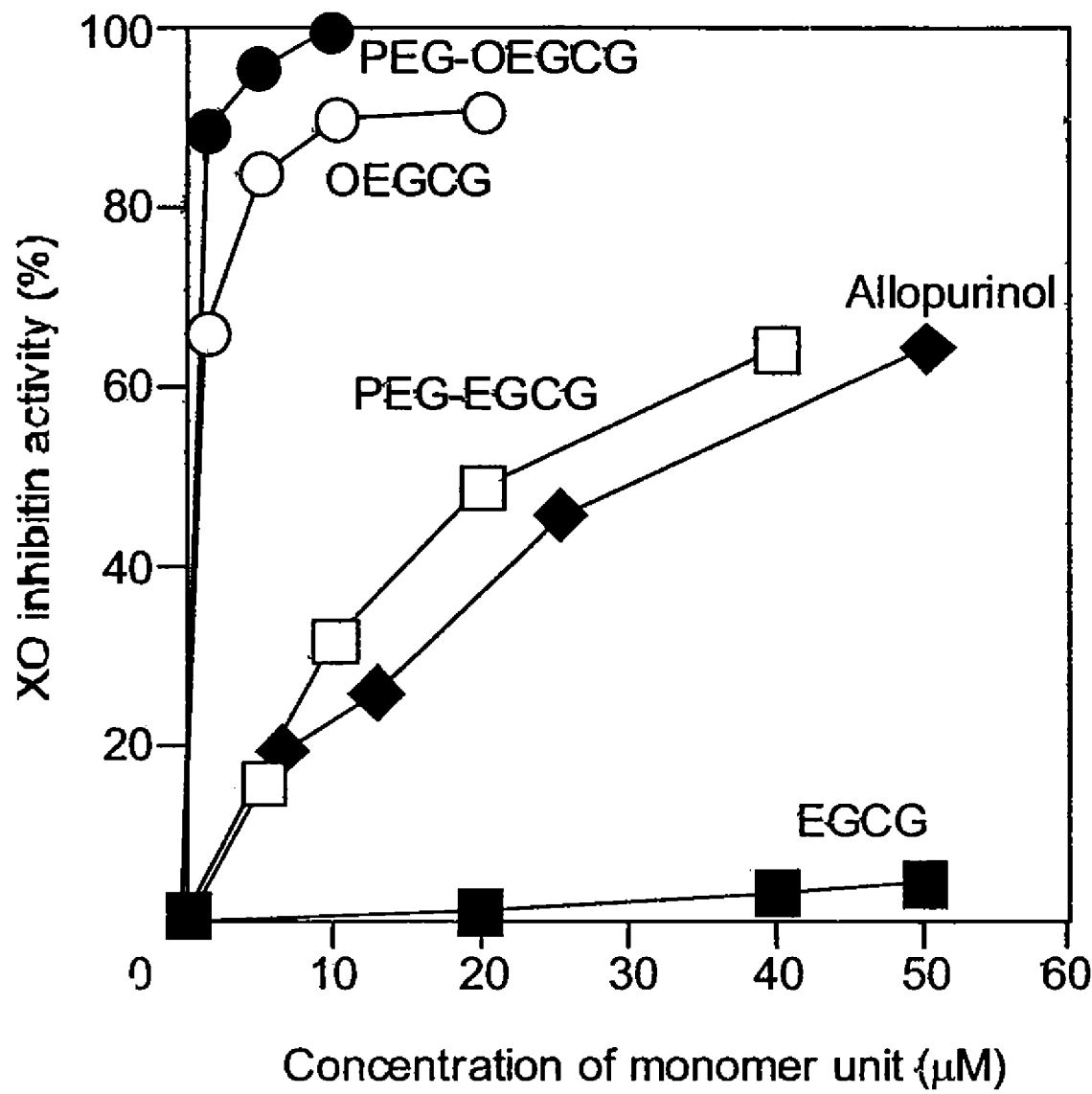
FIG. 7 is a graph depicting XO inhibition activity of EGCG, OEGCG, PEG-EGCG, PEG-OEGCG, and Allopurinol (n=8)
Figure 8:
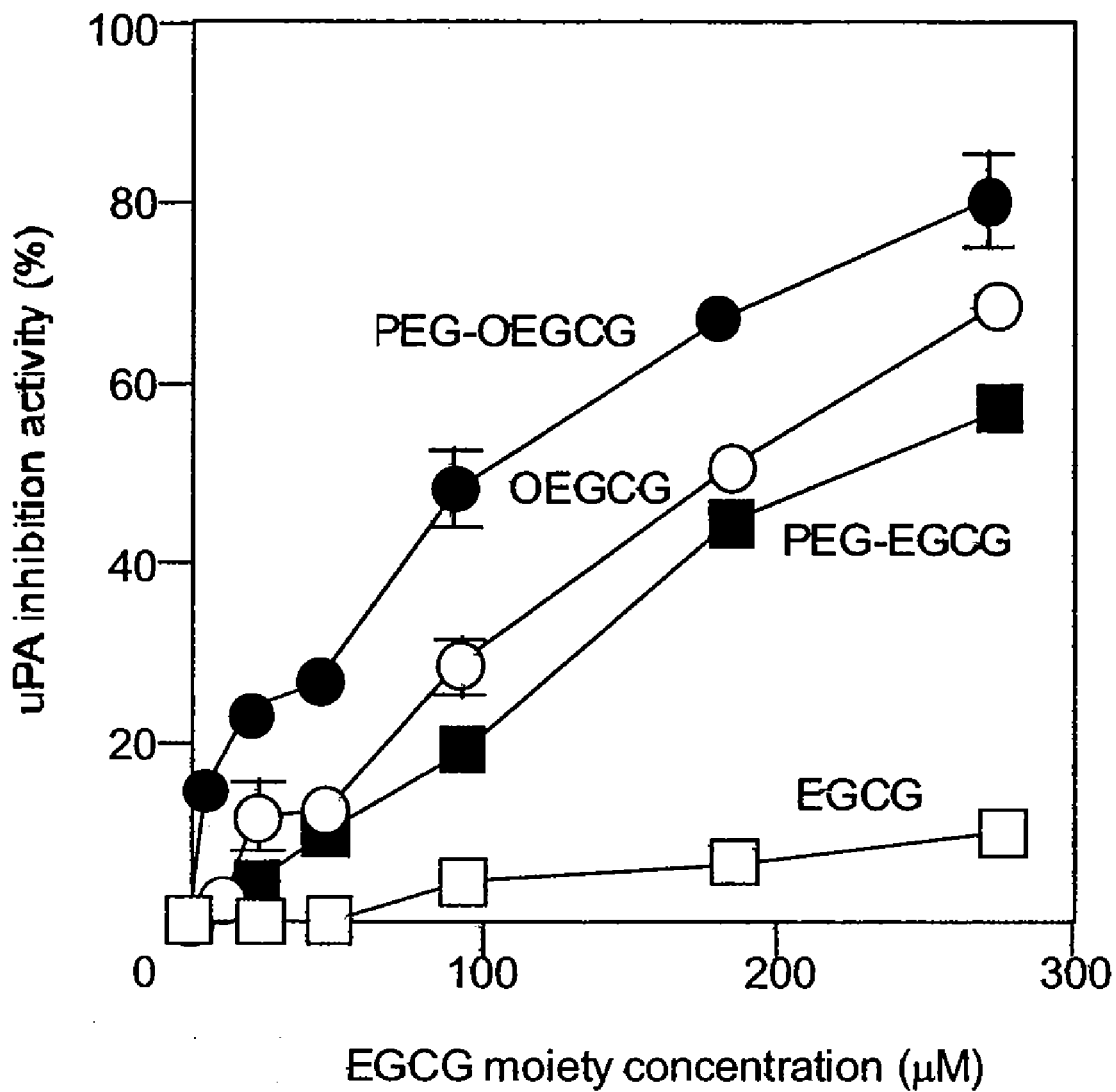
FIG. 8 is a graph depicting uPA inhibition activity of EGCG, OEGCG, PEG-EGCG, and PEG-OEGCG (n=8)

Xanthine oxidase inhibitory activity: XO is not only an important biological source of reactive oxygen species but also the enzyme responsible for the formation of uric acid associated with gout leading to painful inflammation in the joints (McCord J. M. and Fridovich I. *J. Biol. Chem.* 1968, 243, 5753; Chiang H. C., Lo Y. J. and Lu F. J. *J. Enzyme Inhibition* 1994, 8, 61). FIG. 7 shows XO inhibitory activity assessed by evaluating uric acid formation from XO. All of OEGCG, PEG-EGCG, and PEG-OEGCG exhibited higher inhibition activities than that of allopurinol, a frequently used commercial inhibitor for gout treatment (Feher M. D., et al. *Rhermatology* 42, 321 (2003)), in a concentration dependent manner. In contrast, EGCG showed lower inhibition activity, namely less than about 5% inhibition over the range of concentrations tested. The inhibition activities measured using 10 μM of samples were 100, 89.3, 30.7, 22.6, and 1.2% for PEG-OEGCG, OEGCG, PEG-EGCG, and allopurinol, and EGCG, respectively. Since compounds capable of inhibiting XO can also positively affect the activity to scavenge superoxide radicals, the XO inhibitory activity might partly contribute to the results showed in Table 4. However, the XO inhibitory activity was lower than superoxide radical scavenging activity in a range of tested concentrations. Therefore, the greater inhibition effect of OEGCG and those conjugates on the superoxide anion scavenging appears to result predominantly from superoxide radical scavenging rather than from XO inhibition. These results demonstrate that the EGCG oligomers and PEG conjugates possess a higher potential for both superoxide anion scavenging and XO inhibition, as compared with unmodified EGCG.

uPA inhibitory activity: Human cancers need proteolytic enzymes to invade cells and form metastases. One of these enzyme is urokinase (uPA). Inhibition of uPA can decrease tumor size or even cause complete remission of cancers in mice. The known uPA inhibitors are unlikely to be used in anticancer therapy because of their weak inhibitory activity or high toxicity. EGCG was demonstrated to bind to uPA, blocking His 57 and Ser 195 of the uPA catalytic triad and extending towards Arg 35 from a positively charged loop of uPA. Such localization of EGCG would interfere with the ability of uPA to recognized its substrates and inhibit enzyme activity. EGCG showed very low uPA inhibition activity over a range of tested concentrations (FIG. 8). However, OEGCG, PEG-EGCG and PEG-OEGCG showed higher inhibition activities in an EGCG-unit concentration-dependent manner.

Example 3

Micellar Nanocomplex of OEGCG and PEG-EGCG

Materials: (−)-Epigallocatechin gallate (EGCG) was purchased from KURITA LTD., Japan. Aldehyde-terminated polyethylene glycol (PEG-CHO) was purchased from NOF Co., Japan. Acetic acid, acetaldehyde, bovine serum albumin (BSA), fluorescein isothiocyanate-bovine albumin (FITC-BA), PURPALD™ and vanillin were purchased from Sigma-Aldrich. Other reagents and solvents are commercially available and used as received.

Synthesis of OEGCG, PEGCG and POEGCG: Oligomeric EGCG (OEGCG) and poly(ethylene glycol) conjugates with EGCG (PEG-EGCG) were synthesized as above. For OEGCG synthesis, EGCG was dissolved in a mixture of acetic acid/water/DMSO. The reaction was started by addition of acetaldehyde and performed at 20° C. (pH from 1 to 5) under a nitrogen atmosphere for 24 hr. The resulting products were dialyzed (molecular weight cutoff: $1 \times 10^3$) against 1000 times the volume of methanol at room temperature for two days, and then the remaining solution was lyophilized to give OEGCG. For conjugates synthesis, PEG-CHOs and EGCG were separately dissolved in a mixture of acetic acid/water/DMSO. The reaction was started by dropwise addition of PEG-CHO solution and performed at 20° C. (pH from 1 to 5) under a nitrogen atmosphere for 24 hr. The resulting products were dialyzed in a same way described above (molecular weight cutoff: $3.5 \times 10^3$). The PEG-EGCG and conjugate was obtained by lyophilization of dialyzed remaining solution. The molecular weight was estimated by size exclusion chromatography (Waters 2690 equipped with RI-2410 detector, polystyrene standard) with Waters Styragel HR4E/HR5E columns using THF as an eluent at a flow rate of 1 ml/min at 40° C., after acetylation (Mw=4000; Mw/Mn=1.2 and Mw=7900; Mw/Mn=1.2 for OEGCG and PEG-EGCG, respectively).

Interaction of oligomeric (−)-epigallocatechin gallate with protein or DNA: 10 μM of OEGCG stock solutions in DMSO or methanol with various final concentrations (0-0.14 mg/ml) were added to 2 ml of BSA solution in PBS with various concentrations (0-100 mg/ml). Complexes of OEGCG and proteins were formed immediately after mixing by spontaneous self-assembly. The size of complexes was measured at the indicated times for 2 days using particle analyzer (ZetaPALS, BROOKHAVEN INSTRUMENTS Co.). Formation of DNA complex with OEGCG was observed in a same way. ζ-potential of the sample solutions was measured at 25° C. using zeta potential analyzer (ZetaPALS, BROOKHAVEN INSTRUMENTS Co.). Each measurement was run in triplicate.

Micellar nanocomplex carrier formation and characterization: 50 μl of PEG-EGCG solution in DMSO prepared with various concentrations was added to OEGCG/BSA complex solutions to form the micellar nanocomplex (MNC) carrier. The MNC solution was ultrafiltered three times using ultrafiltration membrane (molecular cut off=200000) to remove an excess of flavonoic compounds and protein which not participated in MNC. Size and ζ-potential of MNC were measured at 25° C. using particle analyzer and zeta potential analyzer, respectively. Phenolic content of MNC was assessed by vanillin-HCl assay. 100 μl of a sample was added to 1 ml of 4% vanillin in methanol and the mixture was shaken vigorously. 0.5 ml of concentrated HCl was added then, and the mixture was immediately shaken again. The absorptivity was read at 500 nm after incubating the mixture at room temperature for 20 mM. The phenolic content was determined using EGCG standard curves measured in the same manner; each measurement was run in triplicate. To determine the amount of protein loaded in a MNC carrier, FITC-BA loaded MNC was fabricated in 10 mM Tris (pH 7.0) in a same manner described above and the fluorescence intensity was measured using spectrofluorometer. Wavelengths of excitation and emission were set at 491 nm and 519 nm, respectively. The loading efficiency of protein was determined by dividing the mass of the loaded protein by the initial mass of protein in feed. The amount of protein loaded was expressed as a percentage determined by dividing the mass of the loaded protein by the mass of lyophilized MNC. The morphology of MNC was observed at 200 kV using a transmission electron microscope (TEM) (FEI Tecnai G2 F20 S-Twin). 100 μl of MNC solution stained with 0.001 mg/ml of phosphotungstic acid was fixed on a copper grid coated with carbon film and dried at room temperature for overnight.

Figure 9:
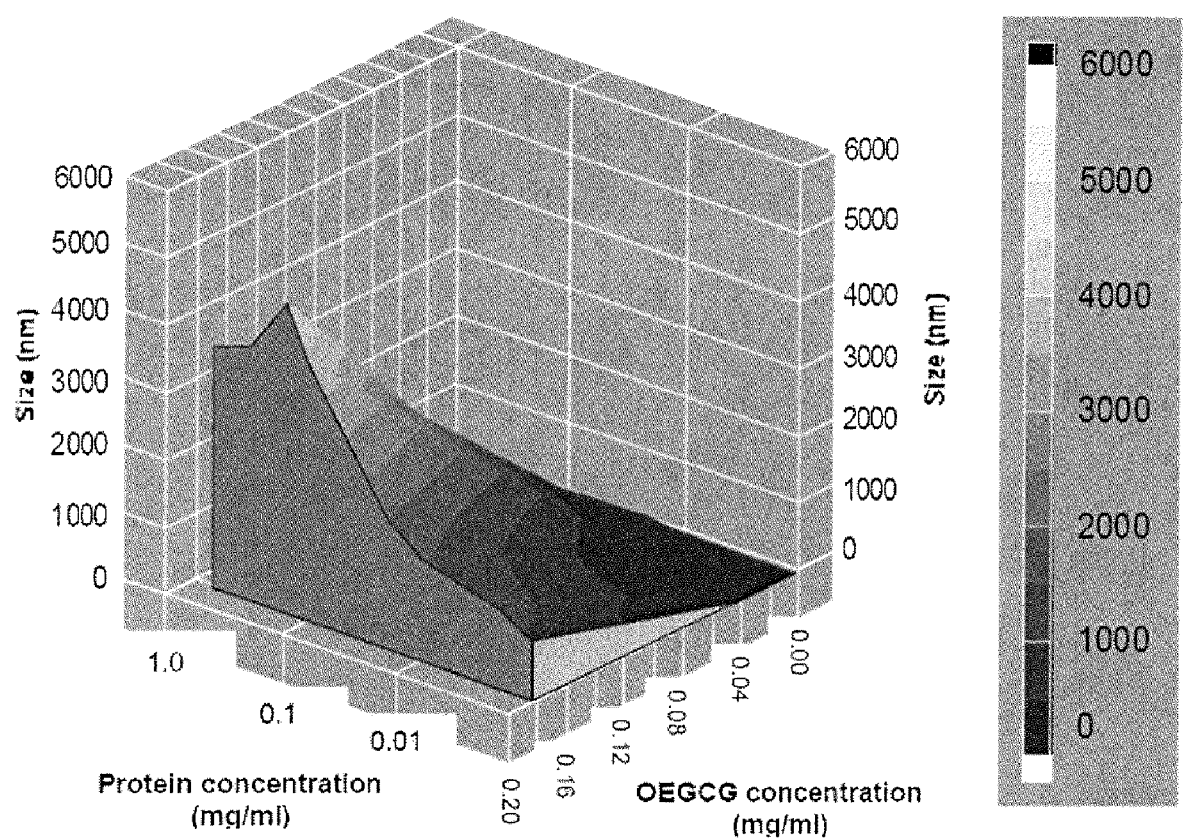
FIG. 9 is a graph showing the effect of OEGCG and protein concentration on the size of the micellar nanocomplex.

Results: In this experiment, complex formation of oligomeric EGCG (OEGCG) with BSA was characterized in terms of the complex size (FIG. 9). When OEGCG was added to BSA solution, the size of particles in the mixture immediately increased due to complex formation. The size of the complex increased with increasing OEGCG concentration at a constant BSA concentration, while no increase in the size was observed with EGCG addition in the range of concentrations tested. As the BSA concentration was varied, the complex increased in size up to a maximum size, after which point the complex size decreased with increasing BSA concentration. These results imply that the complex forms as the protein molecules are bound by OEGCG molecules (Baxter N. J., et al. *Biocehmistry*, 36, 5566-5577 (1997); Siebert K. J., et al. *J. Agric. Food Chem.* 44, 80-85 (1996)). Therefore, when the BSA concentration is less than a critical amount, OEGCG is present in excess allowing for larger particles to form. When the protein concentration is high, complex formation is limited to a smaller size as a resulting of fewer OEGCG molecules available to form a bridge between multiple protein molecules. The complexes were observed to be stable over 2 days.

Figure 10:
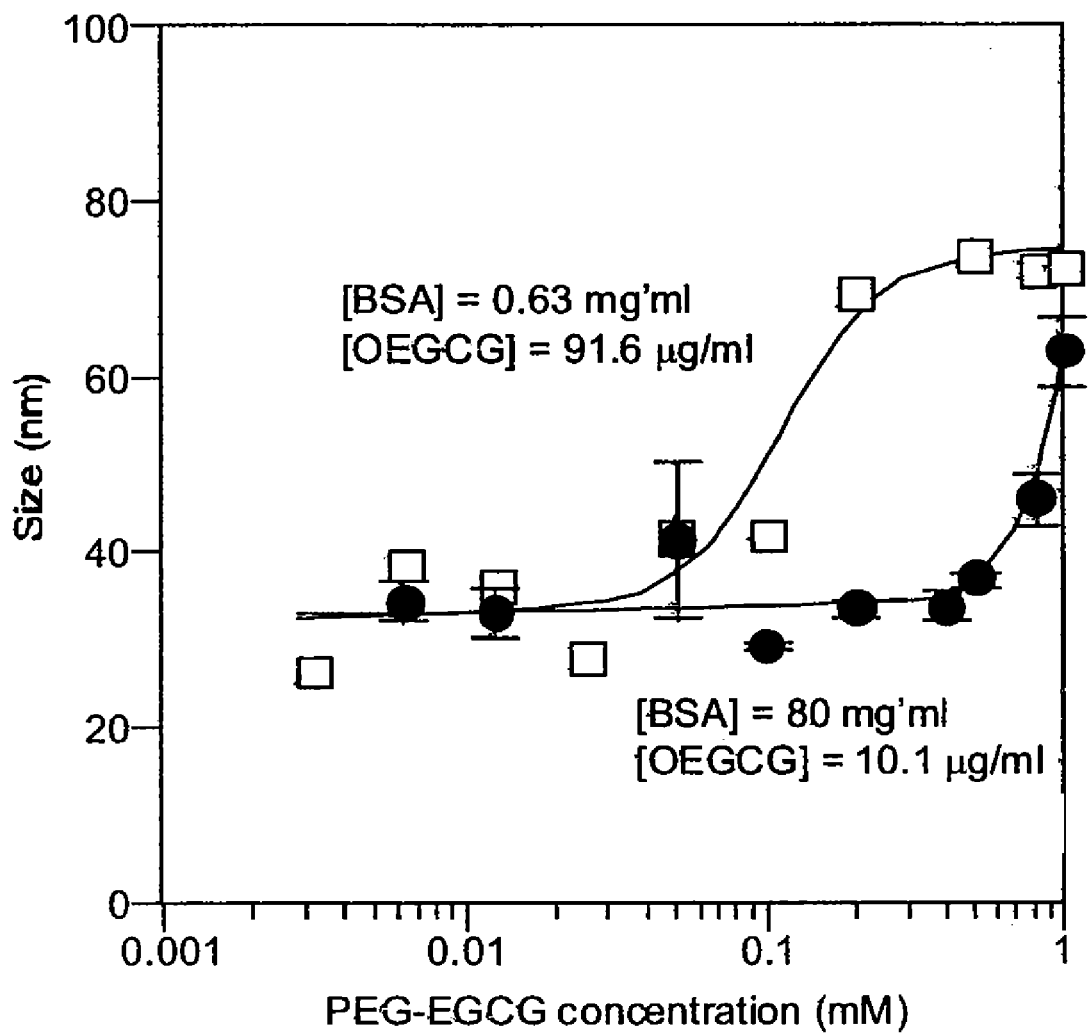
FIG. 10 is a graph showing the effect on size of the micellar nanocomplex upon PEG-EGCG addition, at varying concentrations of PEG.
Figure 11:
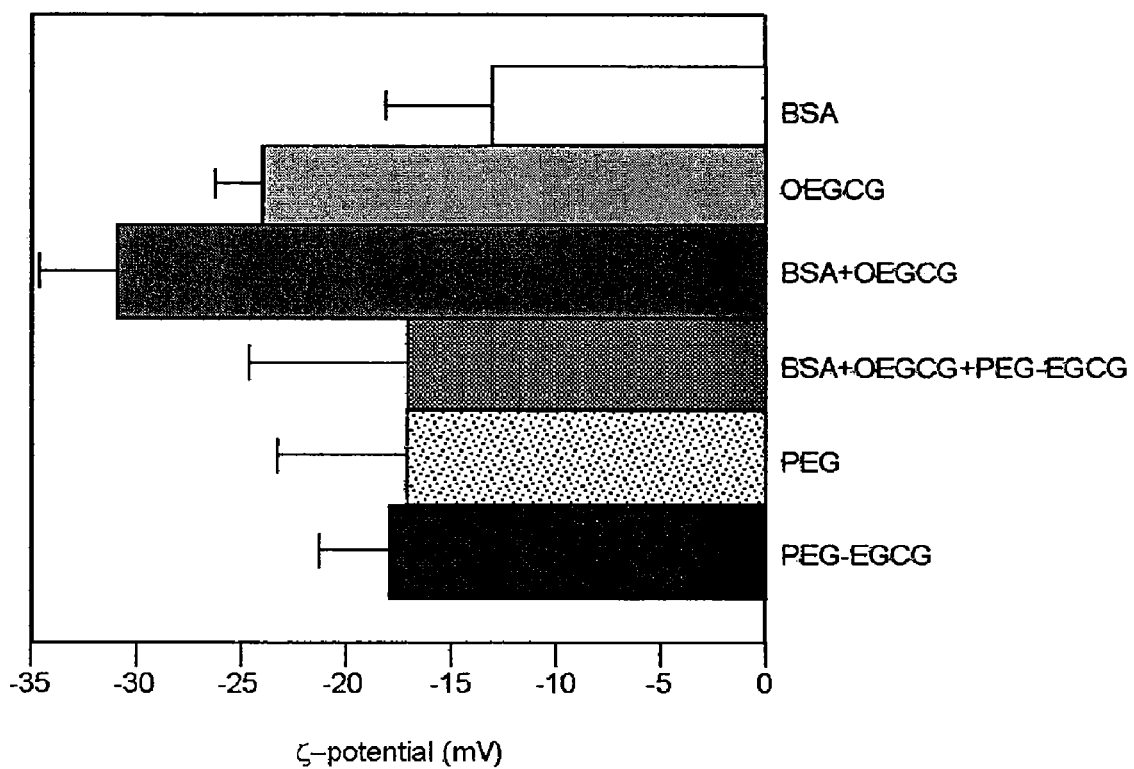
FIG. 11 shows the ζ-potential of the various components in PBS.

PEG-EGCG was successively added to the OEGCG/BSA complex solution with increasing concentrations and the resulting complex size was observed (FIG. 10). Two combinations with different concentrations of OEGCG and BSA were chosen initially to obtain the OEGCG/BSA complex with a diameter of around 30 nm. The size rapidly increased above a certain PEG-EGCG concentration and stopped on around 80 nm, indicating the micellar nanocomplex (MNC) formation by PEG-EGCG assembled surrounding OEGCG/protein complexes. For lower concentrations of BSA, the PEG-EGCG amount needed to form the micelle was relatively smaller, compared to that needed for higher concentrations of BSA.

ζ-potential measurement the complexes also demonstrated the MNC formation (FIG. 11). Surface charge of OEGCG/BSA complexes showed more negative charge than either BSA or OEGCG alone. However, the complex had the same surface charge as that of PEG alone, after addition of PEG-EGCG to the OEGCG/BSA complexes, indicating that the micellar structure is surrounded by PEG chains.

Figure 12:
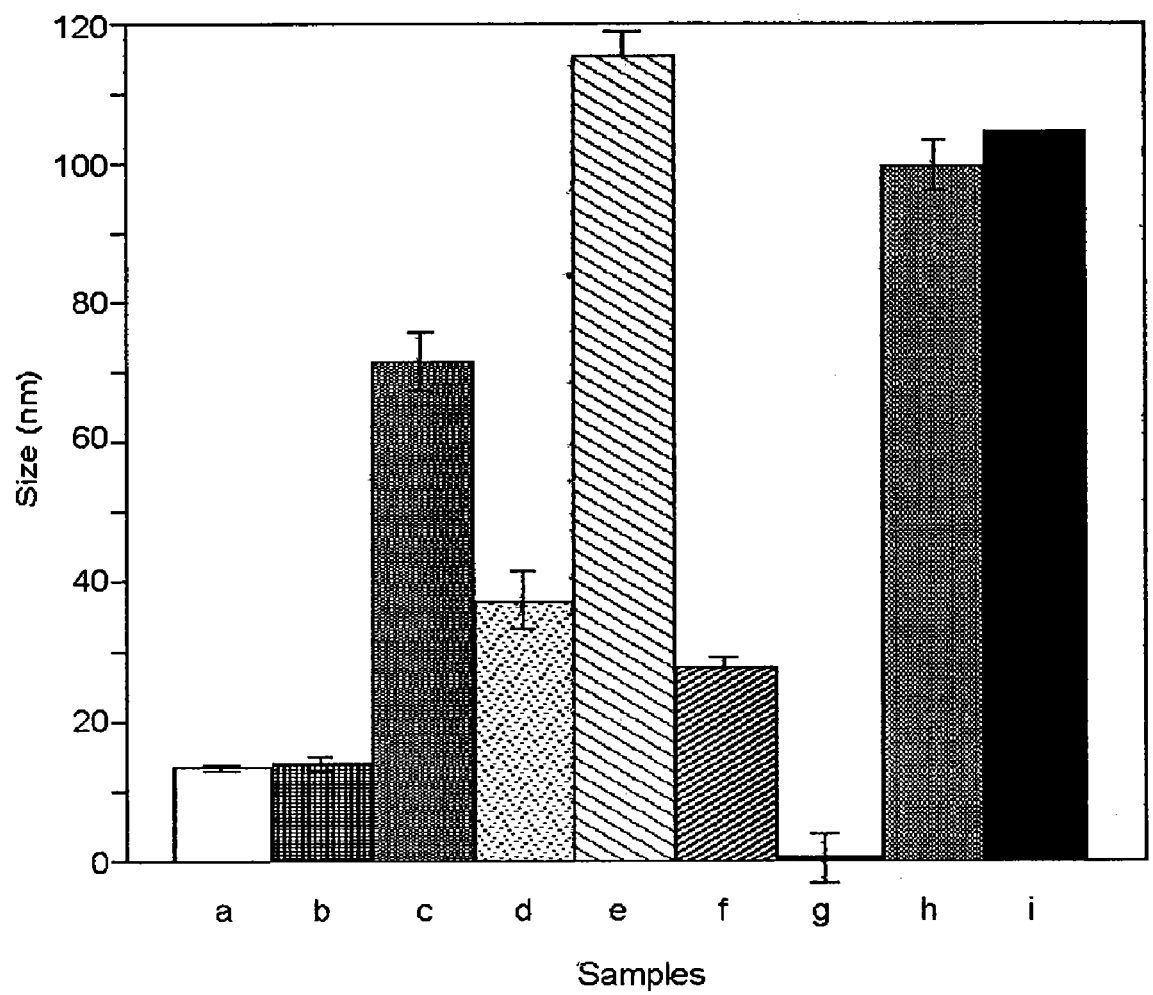
FIG. 12 is a graph indicating the size of the micellar nanocomplex formed in the presence or absence of OEGCG [a: BSA; b: BSA+PEG; c: BSA+PEG−EGCG; d: (BSA+PEG-EGCG)+BSA; e: PEG-EGCG; f: PEG-EGCG+BSA; g: PEG-EGCG in DMSO; h: (BSA+OEGCG)+PEG-EGCG; ((BSA+OEGCG)+PEG−EGCG)+BSA]

In the absence of OEGCG, PEG-EGCG still formed micellar complexes with BSA alone by self-assembly between EGCG moiety of PEG-EGCG and BSA (FIG. 12). Also, the hydrophobic interaction of EGCG moiety was able to drive self-assembly between PEG-EGCGs themselves and formed micelles in an aqueous solution. However, both of the assembly in the absence of OEGCG were not stable enough and showed serious reduction of size when protein was further added, indicating micelle dissociation. In contrast, the complex formed by PEG-EGCG and OEGCG/BSA did not show a change in size upon further addition of protein, likely due to OEGCG stabilization of the nanocomplex structure by strong hydrophobic and hydrogen bonding interaction.

To assess the amount of protein loaded in the nanocomplex, a FITC-BA loaded micelle was fabricated and measured. The protein amount loaded was 39.3% and the loading efficiency was 60.9%. In addition, the flavonoid amount loaded together was determined using the vanillin-HCl method. When the vanillin assay was used for determination of EGCG unit in OEGCG, PEG-EGCG and PEG-OEGCG, the result was quite reproducible and gave nearly same amount as the amount calculated based on their molecular weight. Vanillin-HCl assay revealed 58.5% of flavonoid loading amount with 7.3% loading efficiency.

Figure 13A:
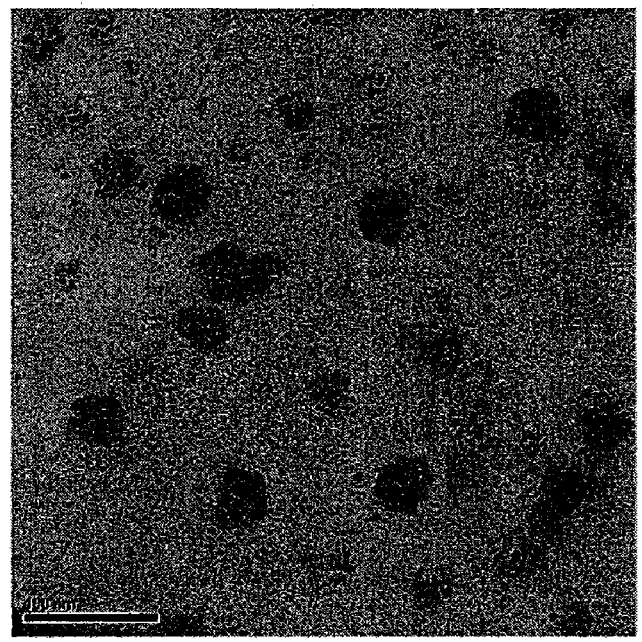
FIG. 13A is a TEM image of the OEGCG/protein, PEG-EGCG micellar nanocomplex.
Figure 13B:
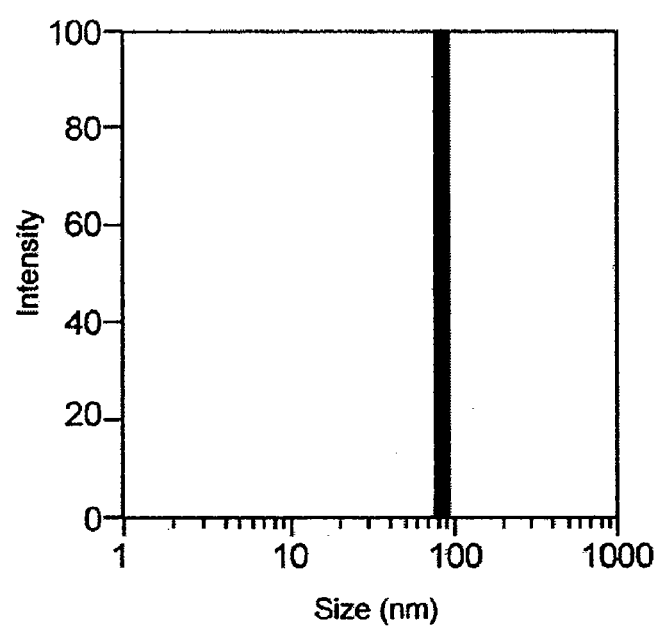
FIG. 13B indicates the size distribution of the OEGCG/protein, PEG-EGCG micellar nanocomplex as measured by light scattering.

Light scattering analysis of the nanocomplex showed a monodispersed particle size around 80 nm (FIG. 13B). TEM image showed a spherical compact shape of the nanocomplex showing good consistency with the size observed by light scattering (FIG. 13A).

Figure 14:
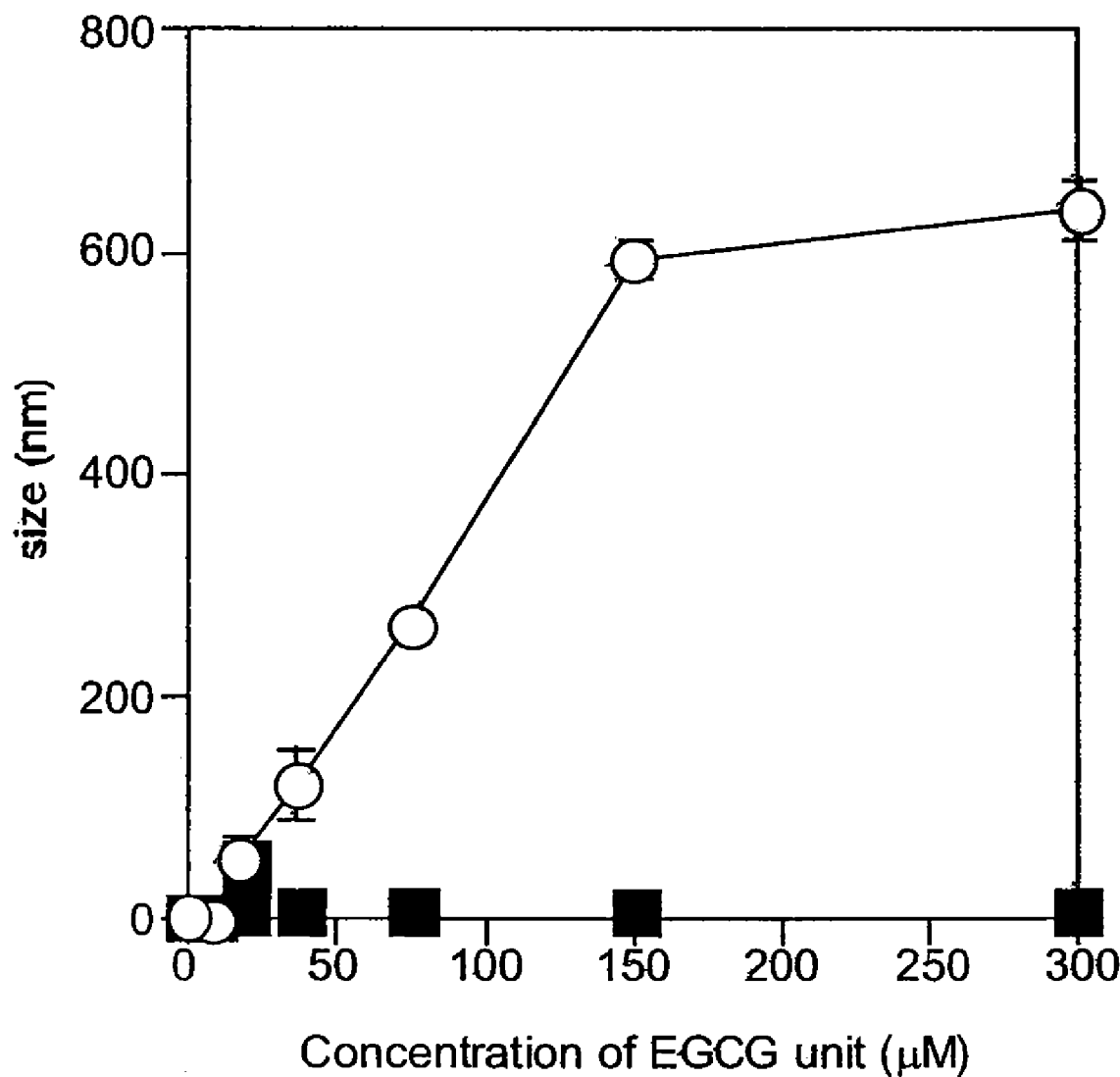
FIG. 14 is a graph indicating the size of the complex formed with DNA [○: OEGCG+DNA; ■: EGCG+DNA]

FIG. 14 indicates that OEGCG forms complexes with DNA as well. The complex size measured by light scattering increased with increase in the concentration of EGCG units of OEGCG. Unmodified EGCG was not observed to form complexes with DNA in a range of concentration tested.

Example 4

PEG-OEGCG Micellar Nanocomplex Formation

Materials: (−)-Epigallocatechin gallate (EGCG) was purchased from KURITA LTD., Japan. Aldehyde-terminated polyethylene glycol (PEG-CHO) was purchased from NOF Co., Japan. Acetic acid, acetaldehyde, bovine serum albumin (BSA) were purchased from Sigma-Aldrich. Other reagents and solvents are commercially available and used as received.

Synthesis of OEGCG, PEG-EGCG and PEG-OEGCG: Oligomeric EGCG (OEGCG) and poly(ethylene glycol) conjugates with EGCG (PEG-EGCG) were synthesized as above. For OEGCG synthesis, EGCG was dissolved in a mixture of acetic acid/water/DMSO. The reaction was started by addition of acetaldehyde and performed at 20° C. (pH from 1 to 5) under a nitrogen atmosphere for 24 hr. The resulting products were dialyzed (molecular weight cutoff: $1 \times 10^3$) against 1000 times the volume of methanol at room temperature for two days, and then the remaining solution was lyophilized to give OEGCG. For conjugates synthesis, PEG-CHOs and EGCG or OEGCG were separately dissolved in a mixture of acetic acid/water/DMSO. The reaction was started by dropwise addition of PEG-CHO solution and performed at 20° C. (pH from 1 to 5) under a nitrogen atmosphere for 24 hr. The resulting products were dialyzed in a same way described above (molecular weight cutoff: $3.5 \times 10^3$). The PEG-EGCG and conjugate was obtained by lyophilization of dialyzed remaining solution. The PEG-OEGCG conjugate was precipitated by centrifugation (rpm=$3.5 \times 10^4$) before dialysis (molecular weight cutoff: 5000) and then lyophilized. The molecular weight was estimated by size exclusion chromatography (Waters 2690 equipped with RI-2410 detector, polystyrene standard) with Waters Styragel HR4E/HR5E columns using THF as an eluent at a flow rate of 1 ml/min at 40° C., after acetylation (Mw=4000, Mw/Mn=1.2; Mw=7900, Mw/Mn=1.2; and Mw=10100, Mw/Mn=1.1 for OEGCG, PEG-EGCG, and PEG-OEGCG, respectively).

Micellar nanocomplex carrier formation: 50 µl of PEG-OEGCG solution in DMSO prepared at various concentrations was added to BSA, EGCG, OEGCG and OEGCG-BSA complex solutions to form the micellar nanocomplex (MNC) carrier. The MNC solution was ultrafiltered three times using ultrafiltration membrane (molecular cut off=200000, ADVANTEC) to remove an excess of uncomplexed flavonoic compounds and protein. The size of MNC was measured at 25° C. using a particle analyzer (ZetaPALS, BROOKHAVEN INSTRUMENTS Co.).

Figure 15:
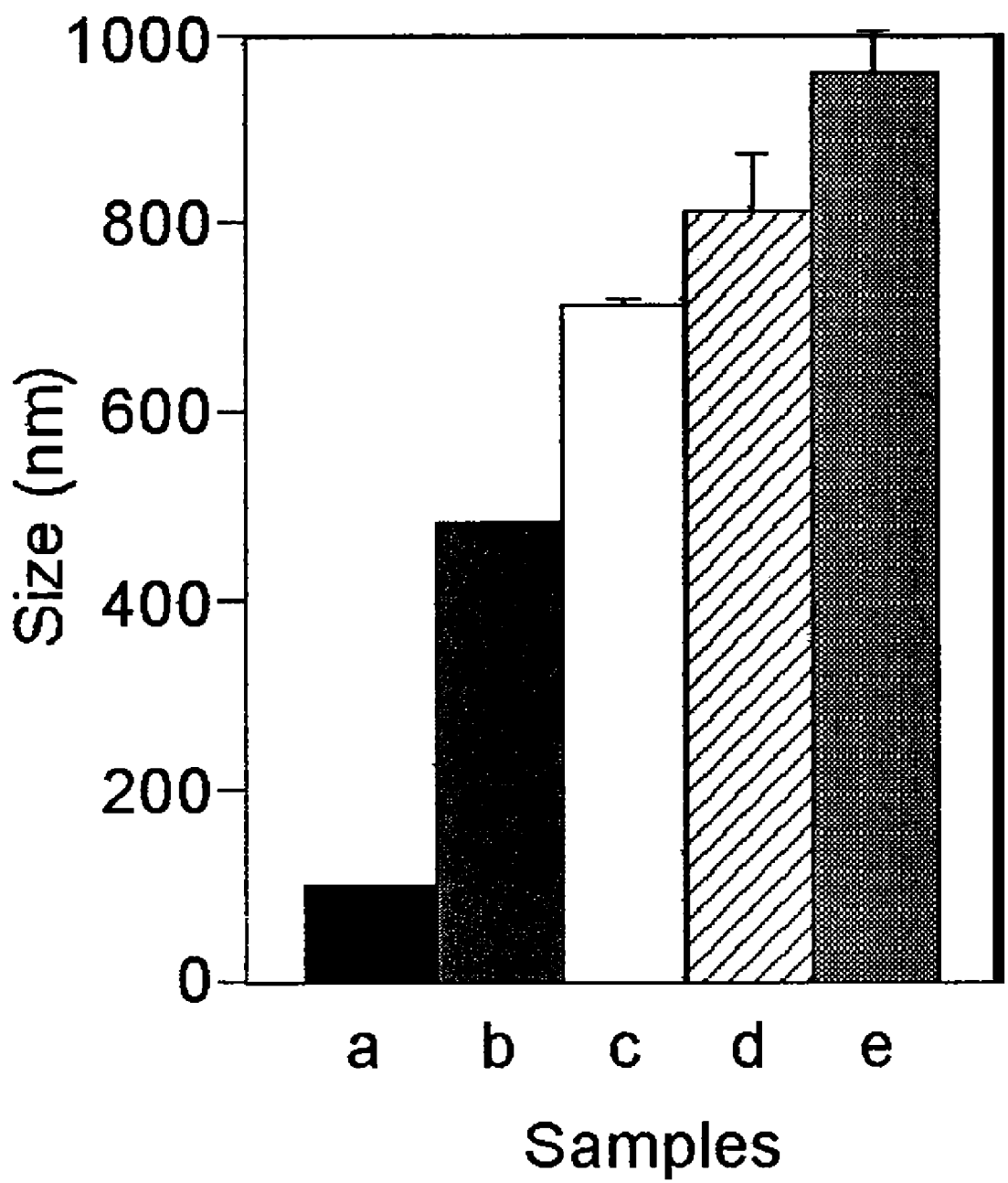
FIG. 15 is a graph showing the size of the complex formed in the various samples [a: (BSA+OEGCG)+PEG-EGCG; b: OEGCG+PEG-EGCG; c: (OEGCG+PEG-EGCG)+BSA; d: OEGCG+PEG; e: (OEGCG+PEG)+BSA]

Results: When PEG-EGCG was added to the OEGCG-protein complex formed in advance, PEG-EGCG spontaneously assembled surrounding the complex and formed micellar complex (MNC) with the complex size around 100 nm. Interestingly, if PEG-EGCG was added directly to OEGCG before complex formation with protein, an insoluble haze-like complex with a size around 500 nm was formed (FIG. 15). This may be due to a strong complex formation of OEGCG with the PEG chain. A similar phenomenon was observed upon addition of OEGCG and unmodified PEG, indicating a strong interaction exists between the OEGCG and PEG chains.

Figure 16:
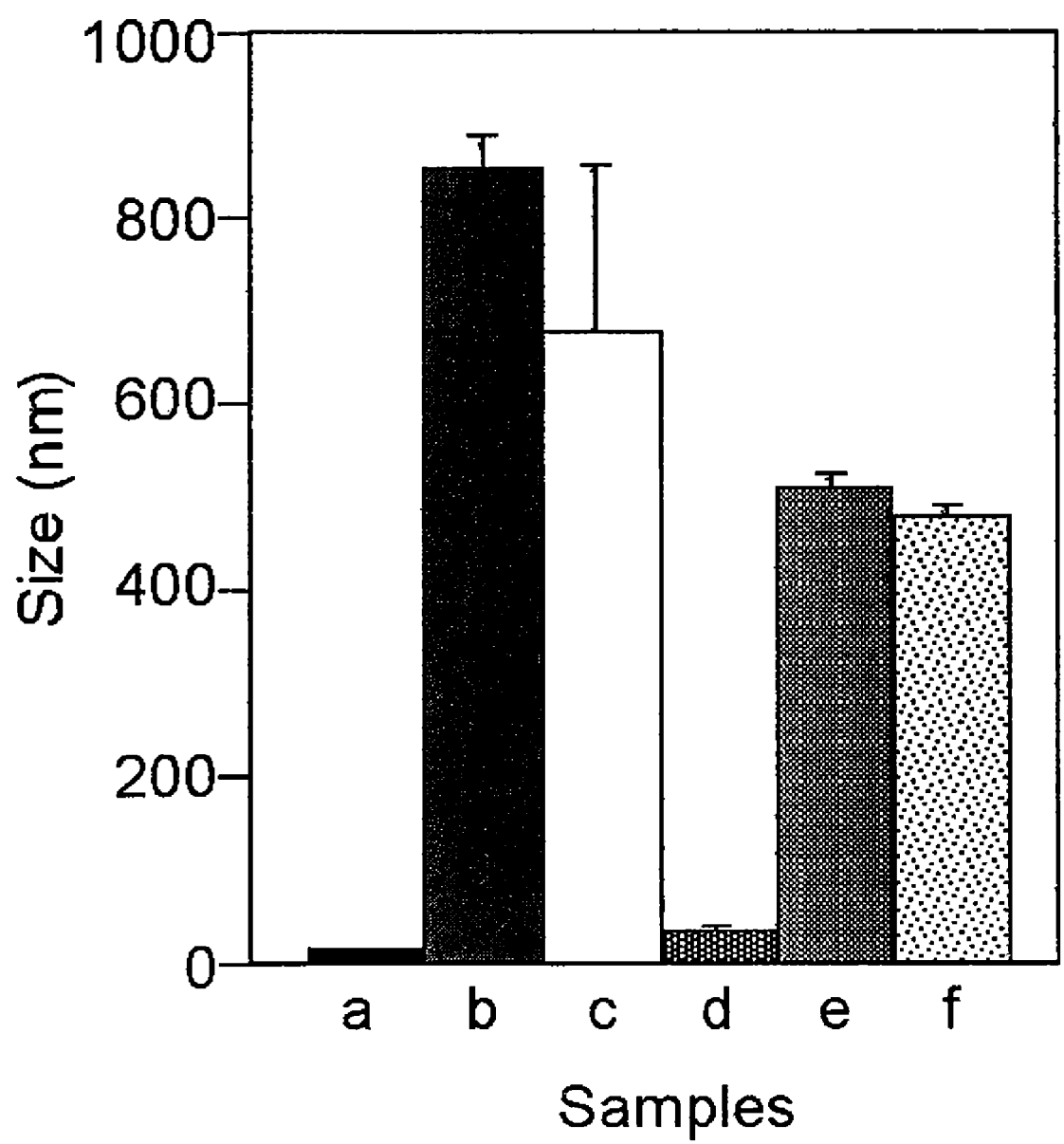
FIG. 16 is a graph showing the size of the complex formed in the various samples [a: BSA; b: BSA+PEG-OEGCG; c: b after ultrasonication; d: BSA+OEGCG; e: (BSA+OEGCG)+PEG-OEGCG; f: e after ultrasonication]

When PEG-OEGCG was added to protein, a large complex formed with a complex size of above 800 nm (FIG. 16). This complex may be induced by intra- and intermolecular complexation between the PEG segment and the OEGCG segment in the conjugate molecule as well as between the conjugates and protein. Unlike in the PEG-EGCG system, addition of PEG-OEGCG to an OEGCG-protein complex formed in advance also resulted in large complexes, even though the size decreased somewhat upon addition of the PEG-OEGCG. These huge complexes were stable against physical crushing energy like ultrasonication.

Figure 17:
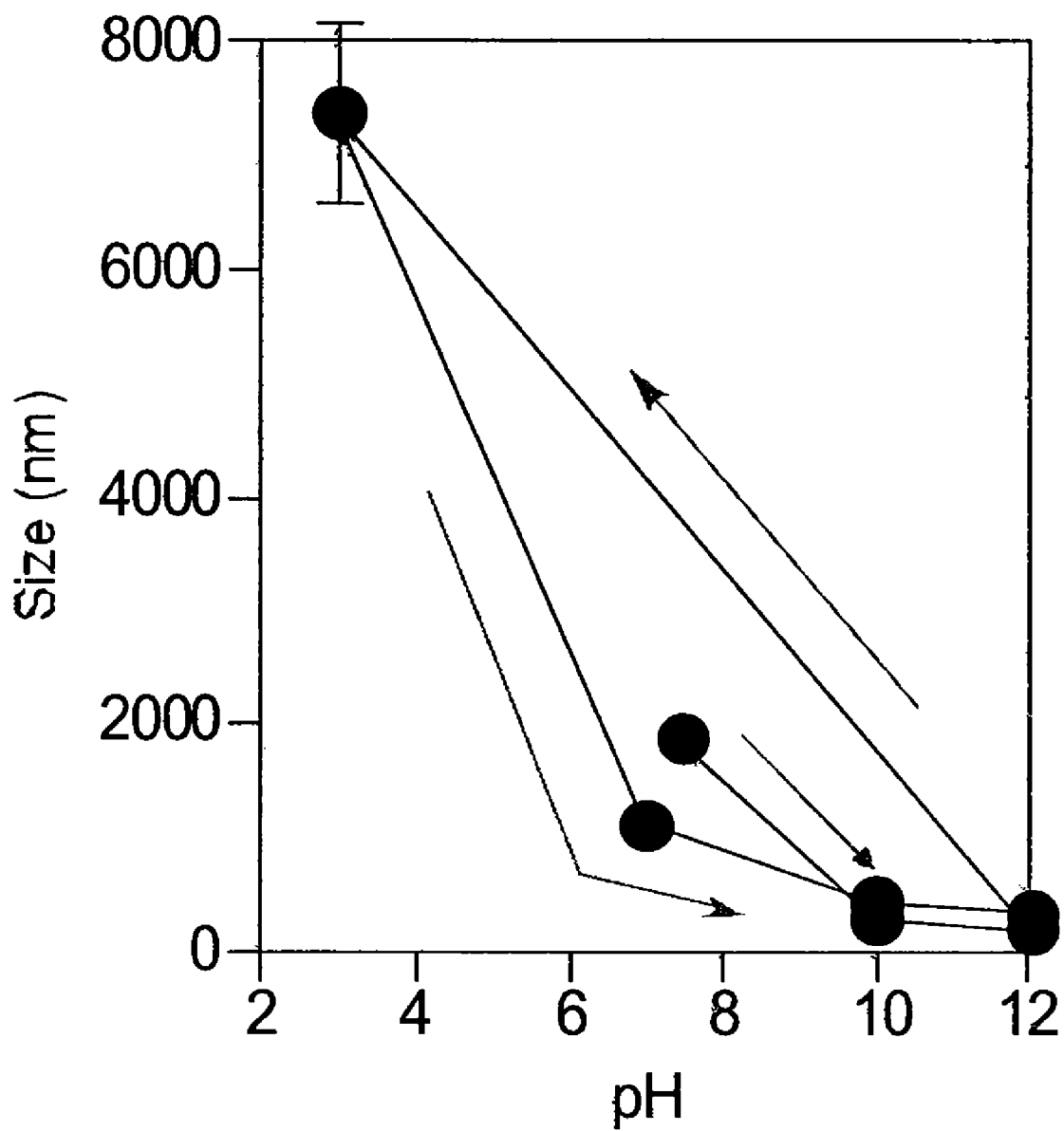
FIG. 17 is a graph showing the effect of pH on PEG-OEGCG complexation.
Figure 18:
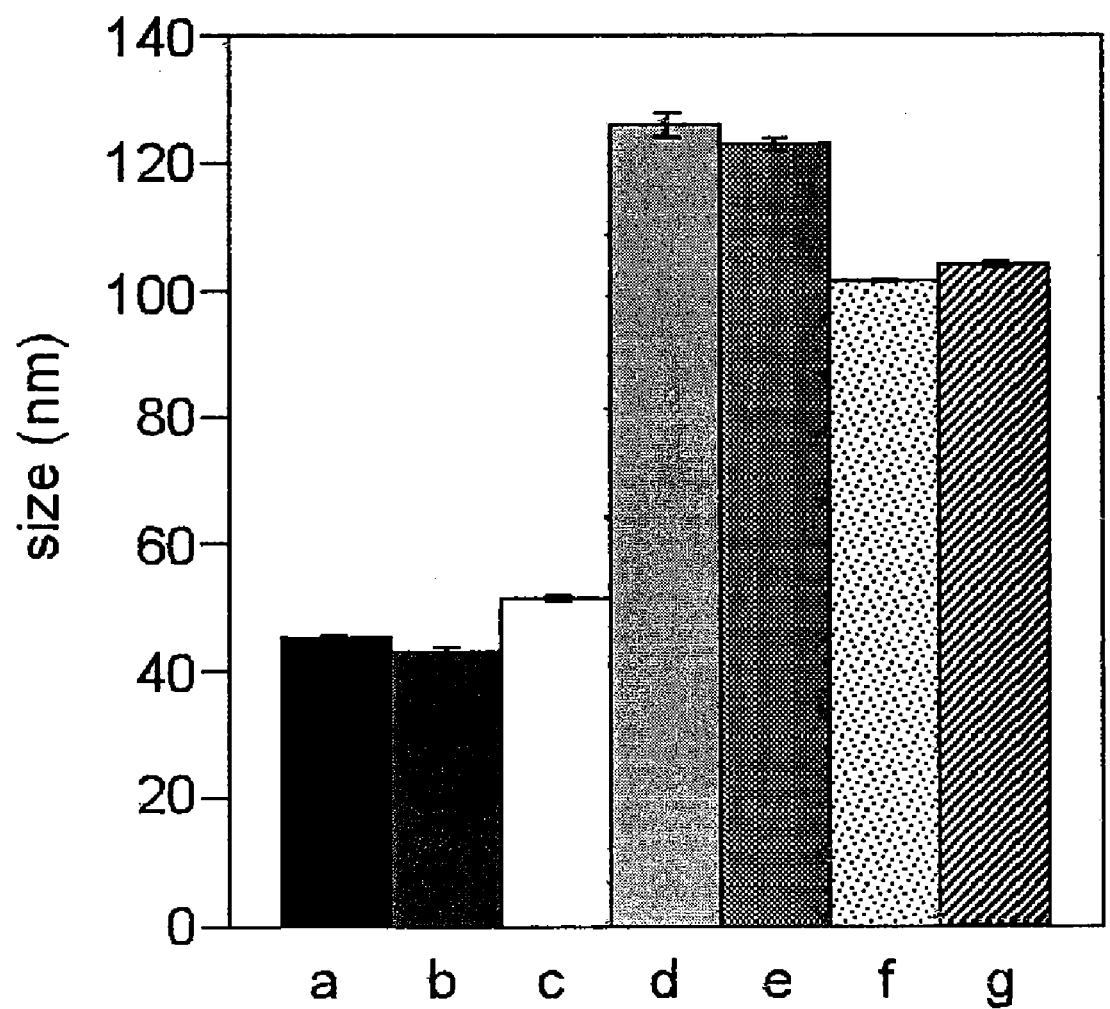
FIG. 18 is a graph showing the size of the complex formed in the various samples [a: PEG-OEGCG in distilled water; b: EGCG+PEG-OEGCG in distilled water; c: OEGCG+PEG-OEGCG in distilled water; d: BSA+PEG-OEGCG in distilled water; e: (BSA+EGCG)+PEG-OEGCG in distilled water; f: (BSA+OEGCG)+PEG-OEGCG in distilled water; g: f after replaced in PBS]

However, the strong complexation of PEG-OEGCG was significantly affected by pH and ionic strength of the medium. FIG. 17 shows the reversible size changes of PEG-OEGCG complexes as pH is varied in the direction of the arrows. Moreover, in distilled water, PEG-OEGCG formed soluble complex with protein, EGCG, OEGCG, and OEGCG-protein complexes, giving a size of around 100 nm (FIG. 18). The complexes once formed in distilled water did not showed size increase again, even when they were placed back in PBS, possible because the OEGCG segments were protected inside the core of the nanocomplex. The strong interaction of OEGCG with PEG may be attributable to the increase in hydrophobicity and hydrogen bonding of these compounds in acidic and salt-containing solutions.

Example 5

Injectable Biodegradable Hydrogels for Drug Delivery and Tissue Engineering

Figure 19:
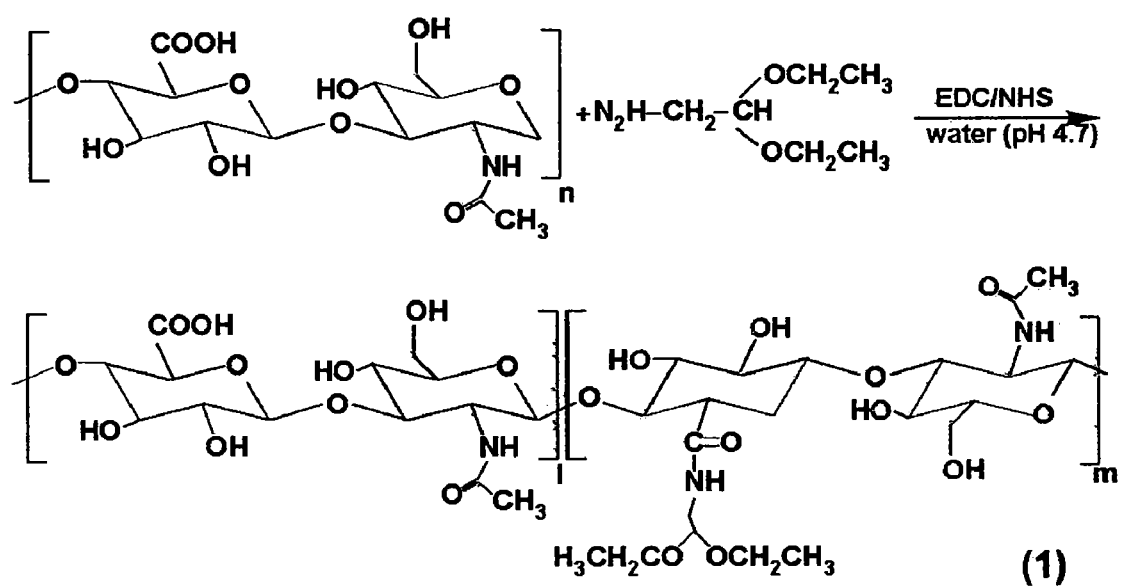
FIG. 19 is a representation of the synthesis method of hyaluronic acid-aminoacetylaldehyde diethylacetal conjugate.

Synthesis of hyaluronic acid-aminoacetylaldehyde diethylacetal (HA-ADD) conjugate: The HA-AAD conjugate ((1) in FIG. 19) was synthesized by following the general protocol as follows. Hyaluronic acid (HA) (1 g, 2.5 mmol) was dissolved in 100 ml of distilled water. To this solution aminoacethlaldehyde dietylacetal (1.2 g, 9 mmol) was added. The pH of the reaction mixture was adjusted to 4.7 by the addition of 0.1M HCl. N-Hydroxysuccinimide (0.34 g, 3.0 mmol) and 1-ethyl-3-[3-(dimethylamino)propyl]carbodiimide hydrochloride (EDC) (0.575 g, 3.0 mmol) were added to the solution. After mixing, the pH of the reaction was maintained at 4.7. The solution was kept at room temperature for 24 h under gentle stirring. The mixture was subjected to purification by dialysis (molecular weight cut off=1000).

Figure 20:
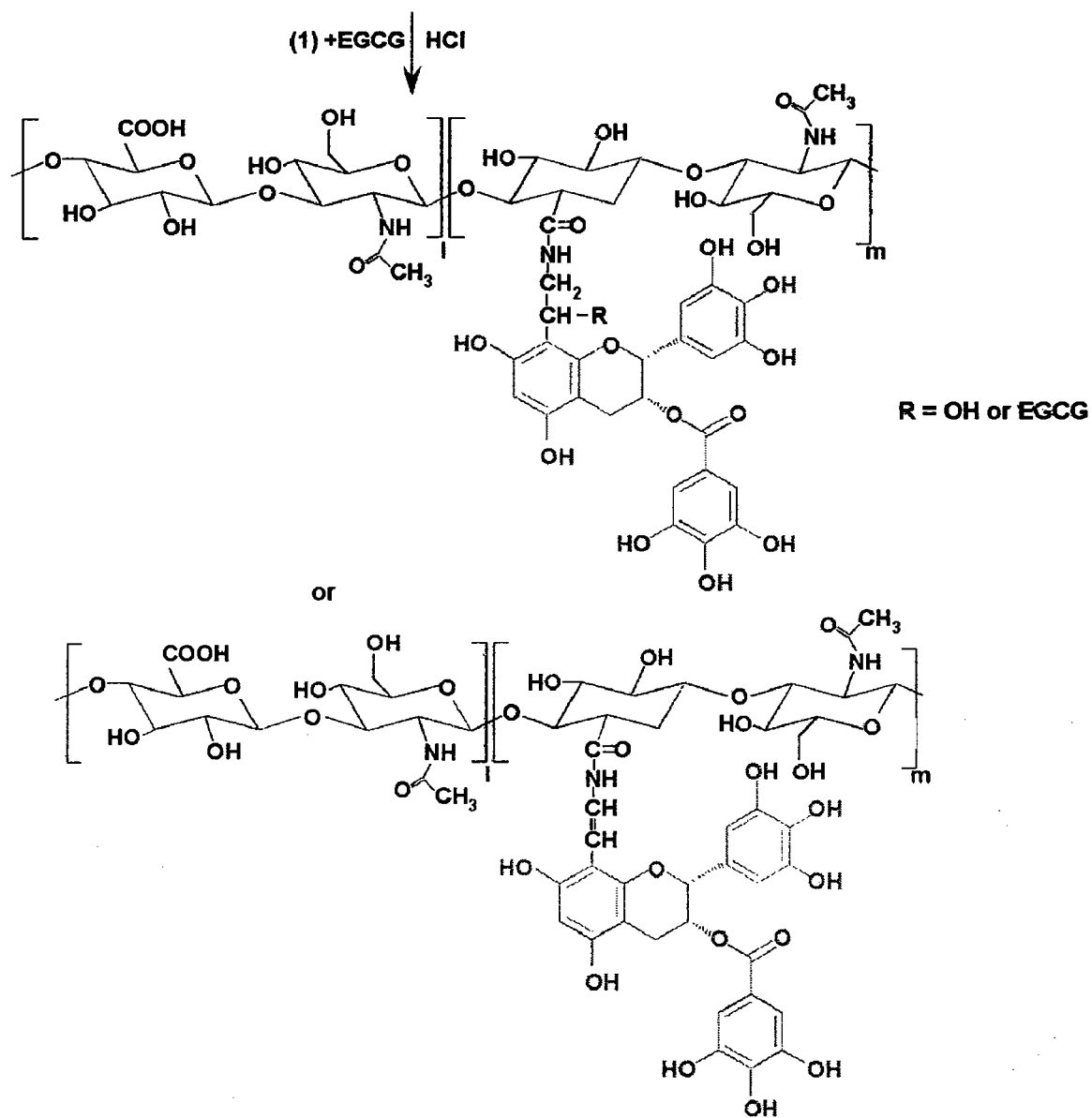
FIG. 20 is a representation of the synthesis method of hyaluronic acid-EGCG conjugate.
Figure 21:
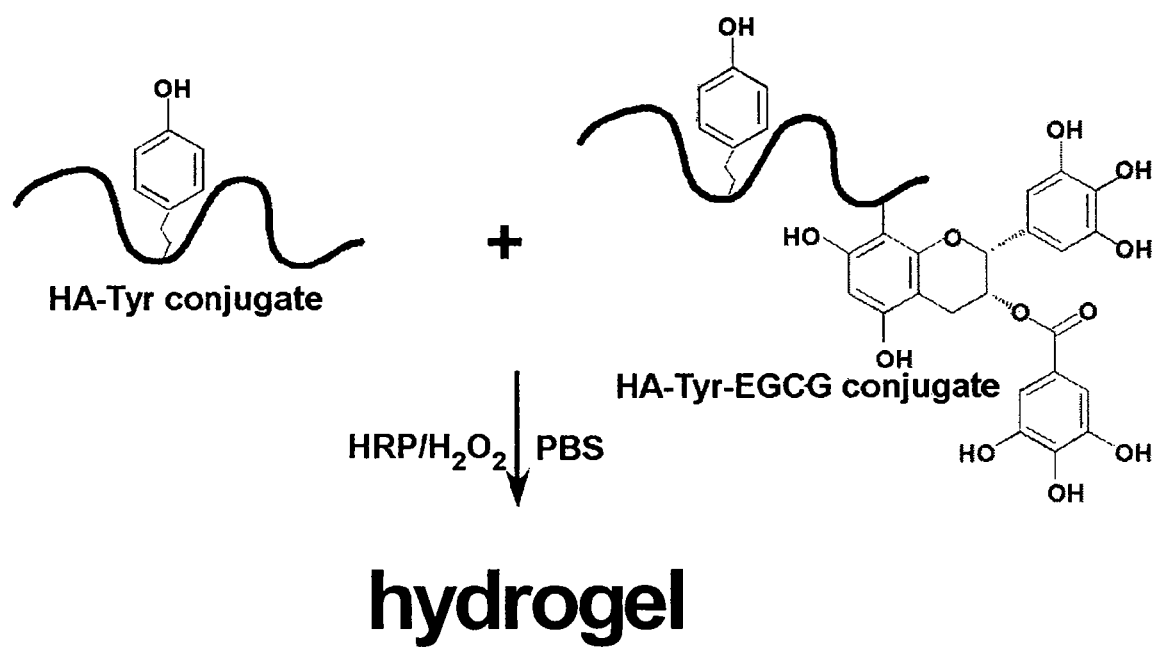
FIG. 21 is a schematic depiction of synthesis of an hyaluronic acid-tyramine-EGCG (HA-Tyr-EGCG) hydrogel.

Synthesis of hyaluronic acid-epigallocatechin gallate (HA-EGCG) conjugate: HA-EGCG conjugate was synthesized as follows. 1 g of HA-AAD conjugate (1) was dissolved in 60 ml of distilled water. The pH of the solution was adjusted to 1 by addition of HCl. 5 ml of EGCG solution dissolved in DMSO (0.2 g/ml) was added. The solution was kept at room temperature under nitrogen atmosphere for 24 h with gentle stirring. The mixture was subjected to purification by dialysis (molecular weight cut off=1000), to yield the HA-EGCG conjugate as shown in FIG. 20.

Hydrogel synthesis and BSA release from the hydrogel: Slab-shaped hydrogels were prepared by injecting a solution mixture of HA-Tyr, HA-Tyr-EGCG containing FITC labeled bovine serum albumin (BSA), horseradish peroxidase (HRP) and $H_2O_2$ between two glass plates separated by spacers. After the reaction was complete, the resulting hydrogels were placed in 50 ml of PBS and examined for BSA release from the hydrogel by measuring the fluorescence intensity of FITC-BSA.

Figure 22A:
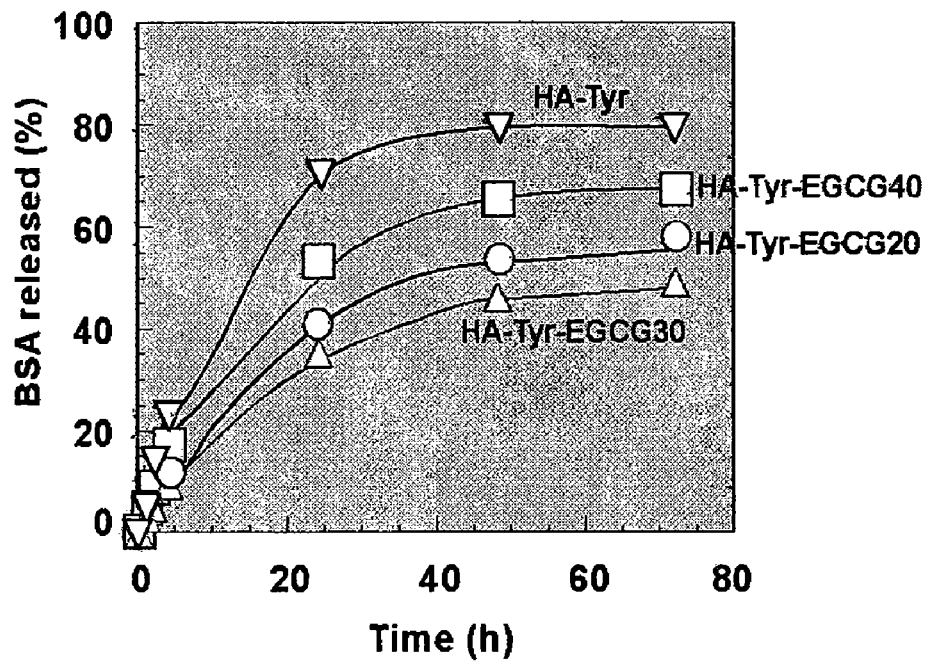
FIG. 22A is a graph showing the amount of FITC-BSA released from various HA-Tyr-EGCG hydrogels.
Figure 22B:
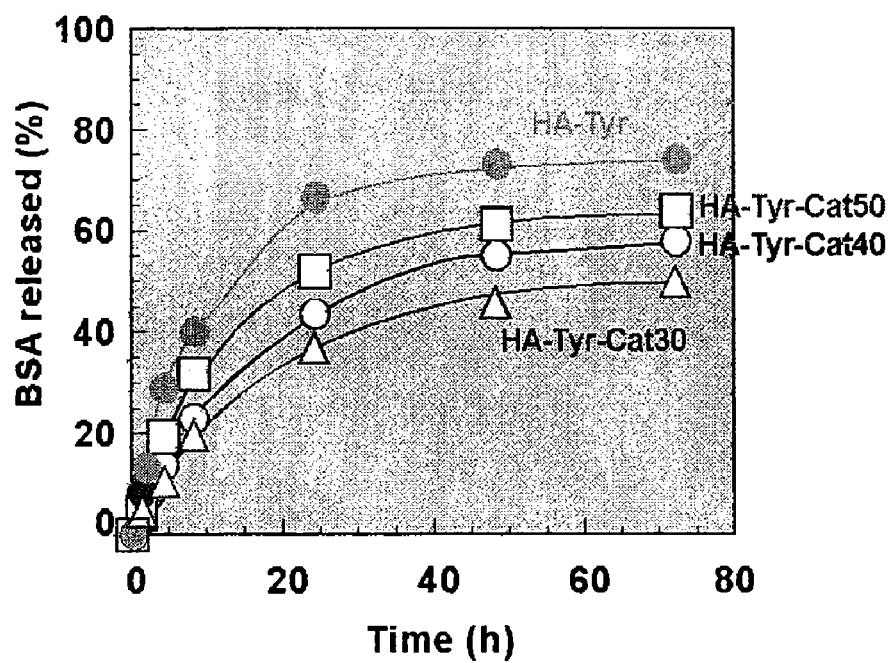
FIG. 22B is a graph showing the amount of FITC-BSA released from various HA-Tyr-catechin hydrogels.

Hydrogels containing EGCG or catechin showed less BSA released compared to that of HA-Tyr with no catechin-based flavonoid (FIG. 22A and FIG. 22B, respectively). This may be due to hydrophobic interactions such π-π stacking between proline side-chains in BSA and the EGCG or catechin moiety in the conjugates. Thus, protein release from the hydrogels containing catechin-based flavonoids may be slower, and would have longer half-life in the body. The hydrogels may also be prepared using the HA-EGCG conjugate described above (or another HA-catechin-based flavonoid conjugate such as HA-catechin) without any tiramine content. In FIG. 22, the hydrogels are composed of varying wt % of catechin-based flavonoid. For example, HA-Tyr-EGCG40 comprises 60 wt % of HA-Tyr and 40 wt % of HA-Tyr-EGCG.

Figure 23A:
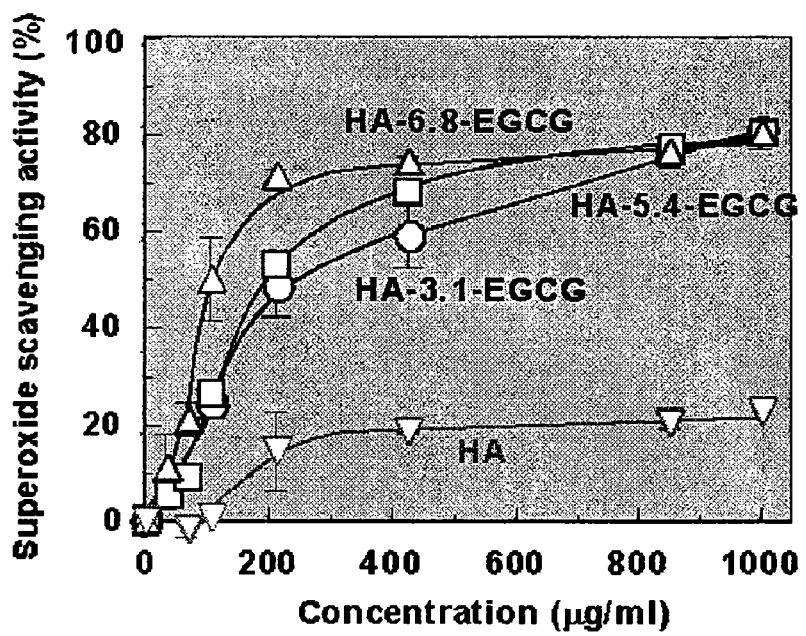
FIG. 23A is a graph showing the superoxide scavenging activity of various hyaluronic acid-EGCG (HA-EGCG) conjugates.
Figure 23B:
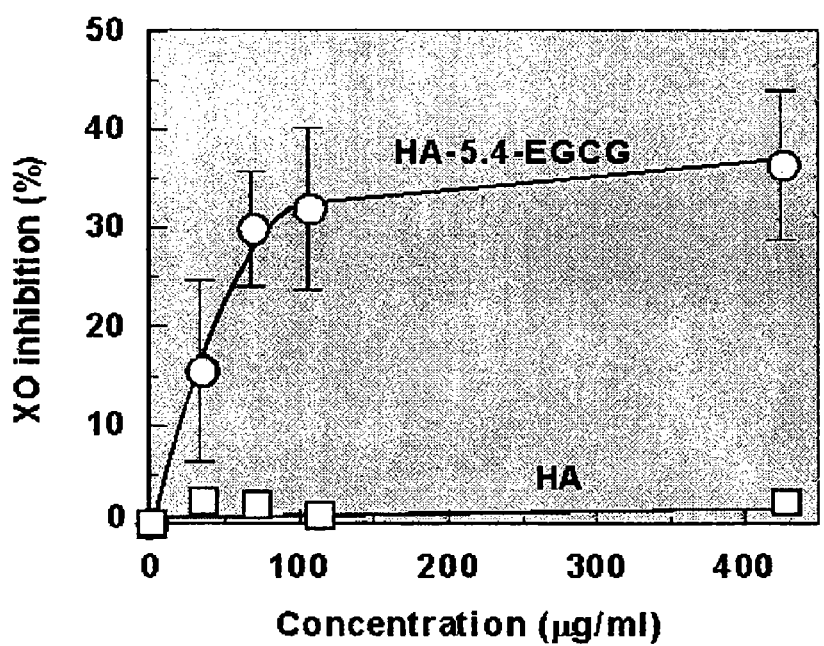
FIG. 23B is a graph showing the xanthine oxidase inhibition activity of various HA-EGCG conjugates.

Xanthine oxidase inhibition and superoxide scavenging activity of HA-EGCG conjugates: These experiments were performed as described above. The results are shown in FIG. 23A and FIG. 23B. In these figures, the ratio of conjugated catechin-based flavonoid to the repeating unit of HA is shown in the name of each conjugate. For example, HA-6.8-EGCG means that the conjugation degree of EGCG to the repeating unit of HA is 6.8%.

Figure 24:
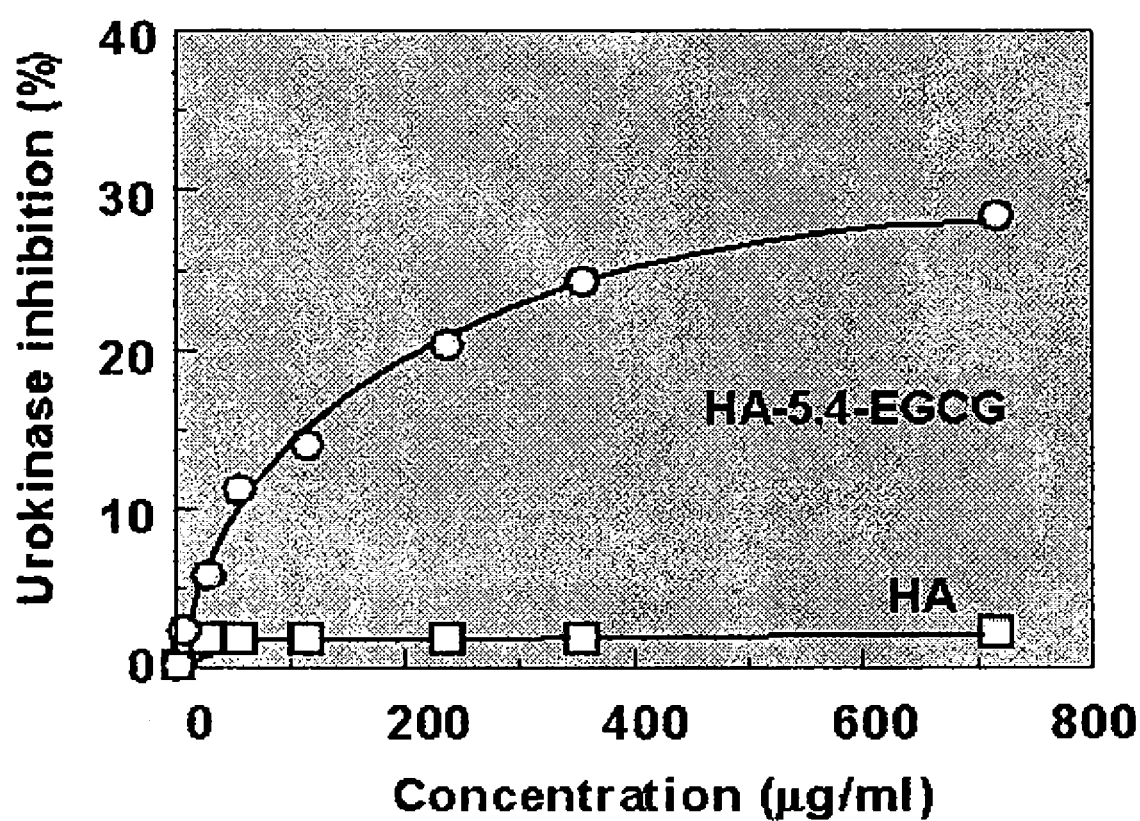
FIG. 24 is a graph showing the urokinase inhibition activity of an HA-EGCG conjugate.

Urokinase inhibition of HA-EGCG conjugates: These experiments were performed as described above. The results are shown in FIG. 24.

Example 6

Reversible Activities of Protein and oligo-epigallocatechin-3-gallate (OEGCG) Upon Complexation and Dissociation Materials and Methods Polymer Synthesis and Characterization: To synthesize OEGCG, EGCG (KURITA LTD., Japan) (1 g) was dissolved in a mixture of acetic acid/water/DMSO. The reaction was started by addition of acetaldehyde (7.2 ml) and performed at 20° C. (pH from 1 to 5) under a nitrogen atmosphere for 48 h. The resulting products were dialyzed (molecular weight cut-off=2000) against 1000 times the volume of DMSO gradually replacing by distilled water. The remaining solution was lyophilized to give OEGCG. To synthesize PEG-EGCG aldehyde-terminated PEG (PEG-CHO, Mw 5000, NOF Co., Japan) (0.35 g) and EGCG (0.65 g) were separately dissolved in a mixture of acetic acetic acid/water/DMSO. The reaction was started by dropwise addition of PEG-CHO solution and performed at 20° C. (pH from 1 to 5) under a nitrogen atmosphere for 48 h. The resulting products were dialyzed (molecular weight cutoff=3500) in a same way described above. The remaining solution was lyophilized to give PEG-EGCG.

Complex characterization: The size and polydispersity of complexes were evaluated by dynamic light scattering measurements using a 90Plus particle sizer (Brookhaven instruments. Co.). ζ-potential of the sample solutions was measured at 25° C. using zeta potential analyzer (ZetaPALS, Brookhaven instruments Co.). The morphology of the complexes was observed at 200 kV using a transmission electron microscope (TEM) (FE1 Tecnai $G^2$ F20 S-Twin).

Activity Assessment: Xanthine Oxidase (from buttermilk, Wako Chemical, XO): XO activity was measured by determining uric acid production at 295 nm in a UV-Vis spectrophotometer (Hitachi, Japan). The solution contained of protein (50 μg/ml) and OEGCG (50 μg/ml)) in a 0.1M phosphate buffer with or without Triton X-100 (0.1%). Each measurement was run in triplicate.

α-Amylase (from *Apergillus oryzae*, Fluka): amylase activity was assayed with an activity kit from Molecular Probes (E-11954) using a fluorescence spectrophotometer (Hitachi, Japan) with excitation wavelength at 505 nm and emission wavelength at 512 nm. The solution contained protein (2.5 μg/ml) and OEGCG (2.5 μg/ml) in a 0.1M phosphate buffer with or without Triton X-100 (0.1%). Each measurement was run in triplicate.

Lysozyme (from egg white, Sigma Chemical): activity of lysozyme was determined spectrophotometically at 450 nm by the decrease in turbidity due to the cleavage of glucosidic linkages of *miccrococcus lysodeikticus* using a UV-Vis spectrophotometer (Hitachi, Japan). The solution mixture contained protein (2.5 μg/ml) and OEGCG (2.5 μg/ml) with or without Triton X-100 (0.1%). Each measurement was run in triplicate.

Radical scavenging activity: $ABTS^{-+}$ was prepared by mixing a 7 mM ABTS stock solution with 2.45 mM potassium persulfate ((1/1, v/v). The decolorization reaction was initiated by adding $ABTS^{-+}$ to samples in a phosphate buffer and immediately measured at 734 nm using a UV-V is spectrophotometer (Hitachi, Japan).

Figure 25:
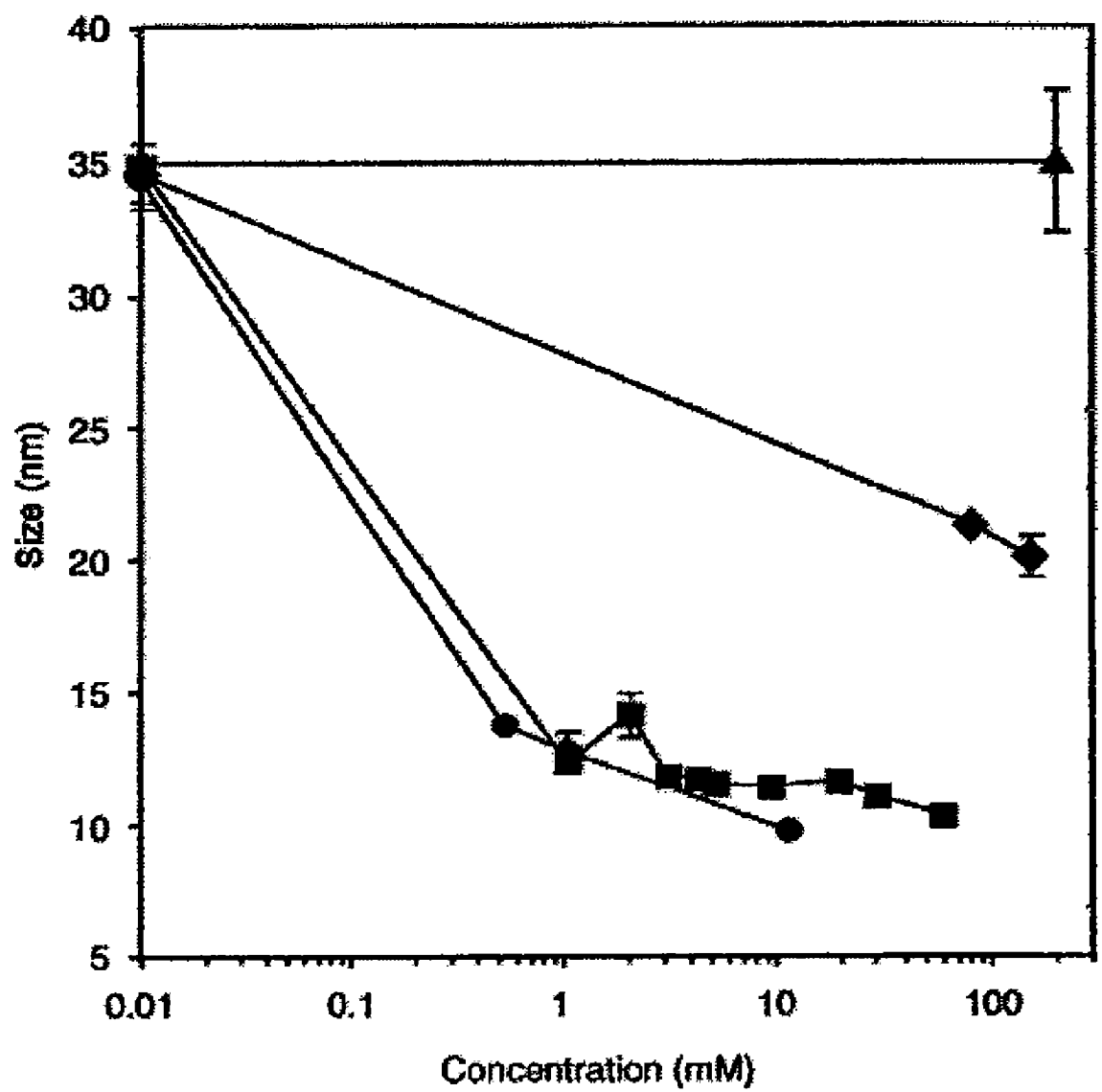
FIG. 25 is a graph showing the size of the BSA/OEGCG complexes by adding urea (triangles), SDS (diamonds), Triton X-100 (squares) and Tween 20 (circles)

Results: To investigate the interaction mode of the complexation, Triton X-100, Tween 20, sodium dodecyl sulphate (SDS) and urea were added to the complex (FIG. 25). Complexes were efficiently dissociated by Triton X-100, Tween 20 and SDS due to hydrophobic competition. Relatively high molecular weight non-ionic detergents, Triton X-100 and Tween 20 were more effective in dissociating the complexes than SDS. However, urea, which has the ability to participate in the formation of strong hydrogen bonds and is not intrinsically hydrophobic, was ineffective in accomplishing dissociation of the complexes in the range of concentrations tested. This result shows that the dominant mode of interaction between OEGCG and protein might be hydrophobic interaction rather than hydrogen bonding.

The polyphenols are renowned for binding to preferred sites and regions on the protein where its aromatic, proline and histidine residues are most readily accommodated by the development of hydrophobic interactions. The association is firmly reinforced by the hydrogen bonds between phenolic hydroxyl groups of polyphenols and polar groups such as the carbonyl group in the vicinity of the binding site of the polyphenol to the peptide linkages of protein surface. OEGCG may bind to proteins in a multidentate fashion at more than one point and cross-link different protein molecules.

Figure 26:
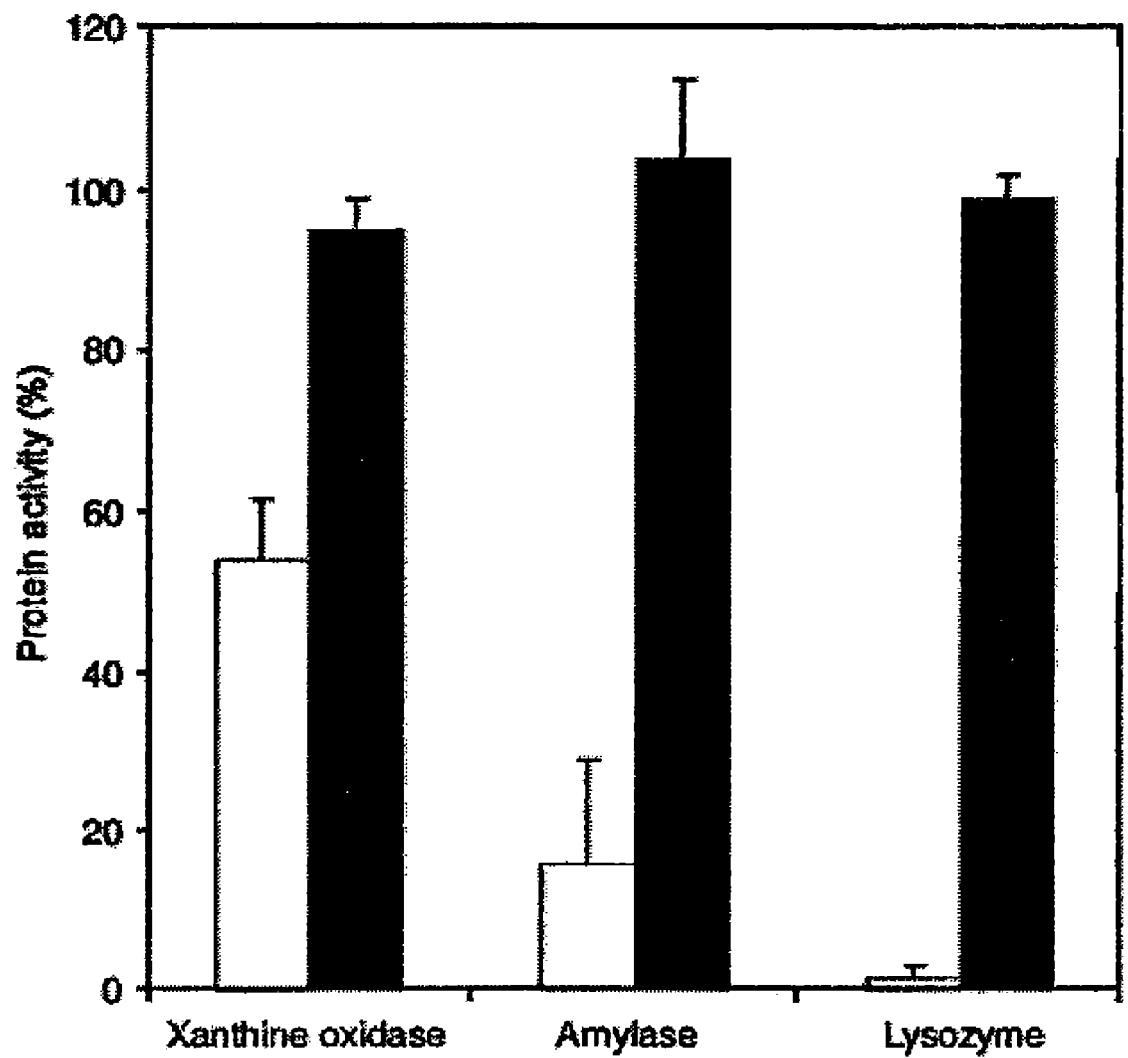
FIG. 26 is a graph showing the activities of various enzymes upon the complexation with OEGCG (white bars) and after the dissociation by Triton X-100 (black bars)

FIG. 26 demonstrates that activities of various proteins were restrained by complexation with OEGCG, but the activities were fully restored when the complexes were dissociated by Triton X-100, implying the conformation change of protein affecting its activity was reversible upon the dissociation.

Figure 27:
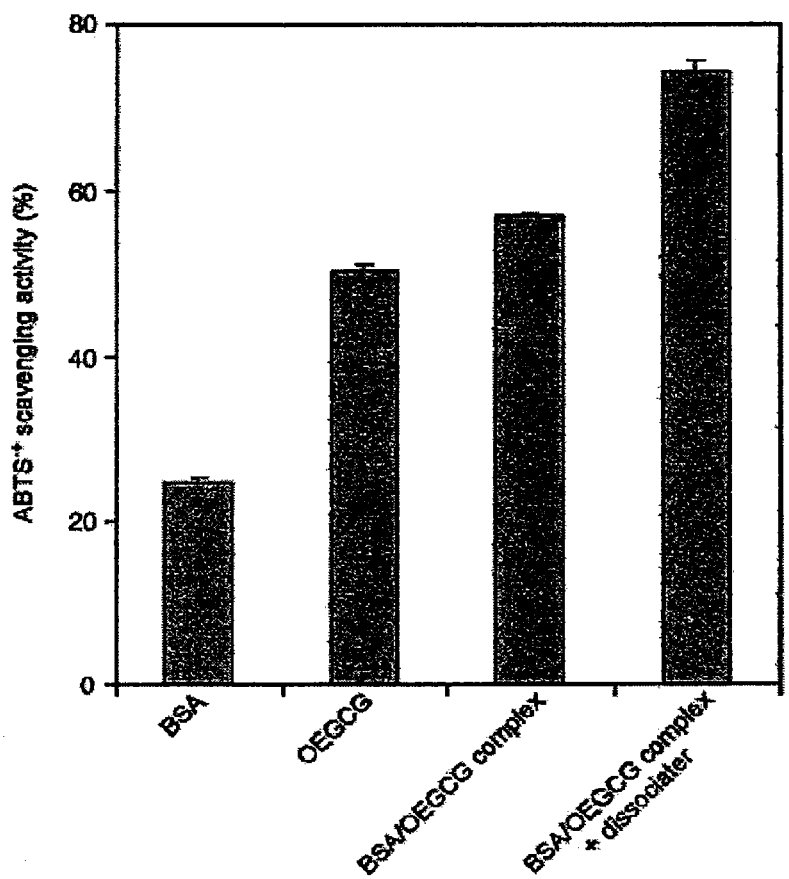
FIG. 27 is a graph showing the ABTS$^+$ scavenging activity of various complexes.

On the other hand, the water soluble radical scavenging activity of OEGCG was investigated as one of representative indexes of its bioactivities (FIG. 27). Similar phenomena were observed, namely, the radical scavenging activity of OEGCG suppressed by complexation with proteins was restored upon dissociation. This implies that complexation is able to preserve the activities of both protein and OEGCG in a dormant state. This property is particularly useful and advantageous in light of the fact that the micelles need to travel through many degrading barriers from point of administration to the intended target (e.g., tumor) sites. As well, the activities of protein and OEGCG are considerably restored upon the dissociation of the micellar complexes.

Example 7

Inhibition and Restoration of Protein Activity with oligo-epigallocatechin-3-gallate (OEGCG)

Materials and Methods

Enzyme Activity Assays: Xanthine Oxidase from buttermilk, Wako Chemical. XO activity was measured by determining uric acid production in a UV-vis spectrophotometer at 295 nm. The increase in absorbance due to the conversion of xanthine to uric acid was followed for 3 minutes. The solution contained 50 μg/mL of protein and DMSO with or without OEGCG samples in a 0.1 M phosphate buffer. To determine the dose dependent response of protein to the test compound, protein to OEGCG ratios were varied from 0.05-5. 164 μM xanthine was added and mixed for 1 minute to start the reaction.

α-Amylase from *Apergillus oryzae*, Fluka. Amylase activity was assayed with an activity kit from Molecular Probes (E-11954) using a fluorescence spectrophotometer with excitation wavelength at 505 nm and emission wavelength at 512 nm. The solution contained 2.5 μg/mL of protein as well as DMSO with and without OEGCG samples in a 0.1 M phosphate buffer. The OEGCG concentrations were varied from μM. To start the reaction, 2.5 μg/mL of fluorescent starch from the Molecular Probes kit was added to the solution and mixed for 30 s. Fluorescence was monitored over a period of 3 minutes.

Catalase from bovine liver, Sigma Chemical. Catalase activity was measured by the disappearance of $H_2O_2$, followed at 240 nm in a UV-Vis spectrophotometer over a period of 200 s. The solution mixture contained 2.5 μg/mL of protein in the presence and absence of OEGCG in DMSO. The reaction was started by adding 0.507M $H_2O_2$ and mixing for 25 s.

Lysozyme from egg white, Sigma Chemical. Activity of lysozyme was determined spectrophotometically at 450 nm by the decrease in turbidity over time due to the cleavage of glucosidic linkages of *Micrococcus lysodeikticus*. The solution mixture contained 2.5 μg/mL of protein with and without OEGCG. To start the reaction, 0.25 mg/mL of *Micrococcus lysodeikticus* was added to the solution.

Activity Recovery with Triton X-100: Recovery of protein activity was measured by adding TX-100 to the reaction mixture of the respective enzymes after protein complexation with OEGCG. Activity was measured according to the specified method for each protein.

Activity for all proteins is calculated with the following equation:

$$\% \text{ Protein Activity} = \frac{\Delta Abs_{sample}}{\Delta Abs_{control}}$$

where $\Delta Abs_{sample}$ is the change in absorbance over time with the test compound and $\Delta Abs_{control}$ is the change in absorbance over time without the test compound.

Figure 28:
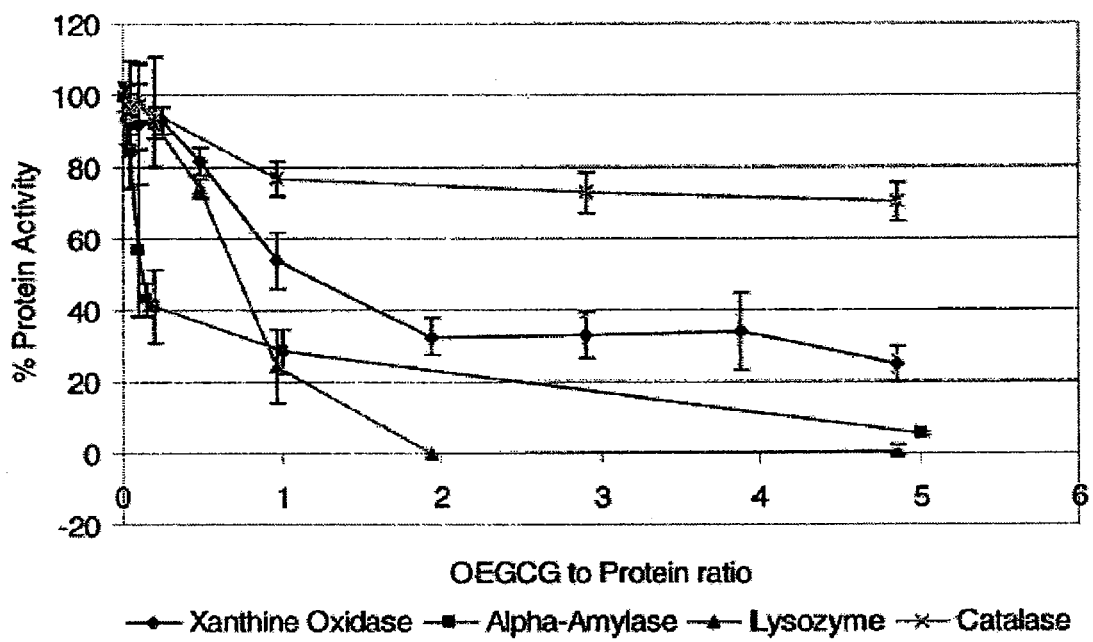
FIG. 28 is a graph showing the dose response curves for the inhibition of various enzymes with increasing weight ratio of OEGCG to protein.

Protein inhibition: The ability of OEGCG to inhibit protein activity is shown in FIG. 28. All proteins show a dose dependent decrease in activity with increasing levels of OEGCG. The error bars obtained in the figure are the result of at least a triplicate measure of separate experiments.

OEGCG had the least inhibitory effect on catalase, which was inhibited only 30% at the highest OEGCG to protein ratio. Moreover, the increase in inhibitory activity did not increase extensively beyond the 1 OEGCG to protein ratio concentration; the five fold increase in OEGCG concentration only resulted in a decrease of protein activity of about 6%.

OEGCG suppressed total XO activity by 75% at the highest concentration. The dose dependent response shows that above a ratio of 2, additional OEGCG did not substantially inhibit protein activity; inhibition only increased about 8%.

Similarly, α-amylase showed a decrease in activity of only 20% as a result of a five fold increase in OEGCG concentration from a ratio of 1 to 5, while the initial 70% activity inhibition occurs with small amounts of additional OEGCG below a ratio of one. The maximum inhibition of α-amylase is about 94%.

Lysozyme showed the most inhibition by OEGCG. All activity was suppressed above an OEGCG ratio of 2 and remains suppressed for higher concentrations. Similar to the other three proteins, the bulk of the inhibition occurs with the initial amounts of OEGCG.

Figure 29:
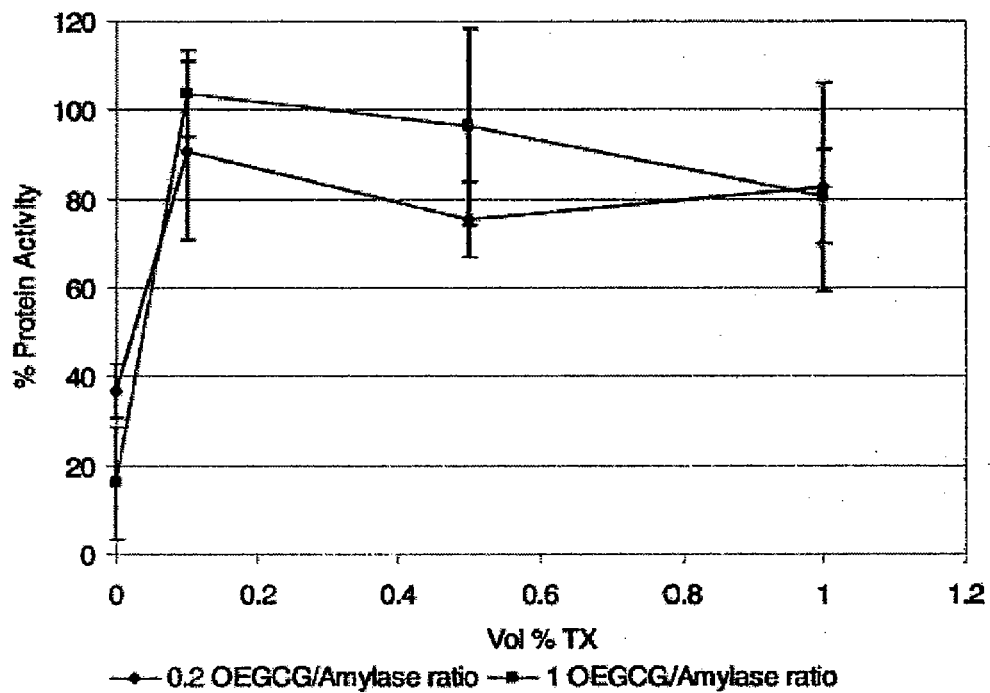
FIG. 29 illustrates the activity recovery of α-amylase with Triton X-100.
Figure 30:
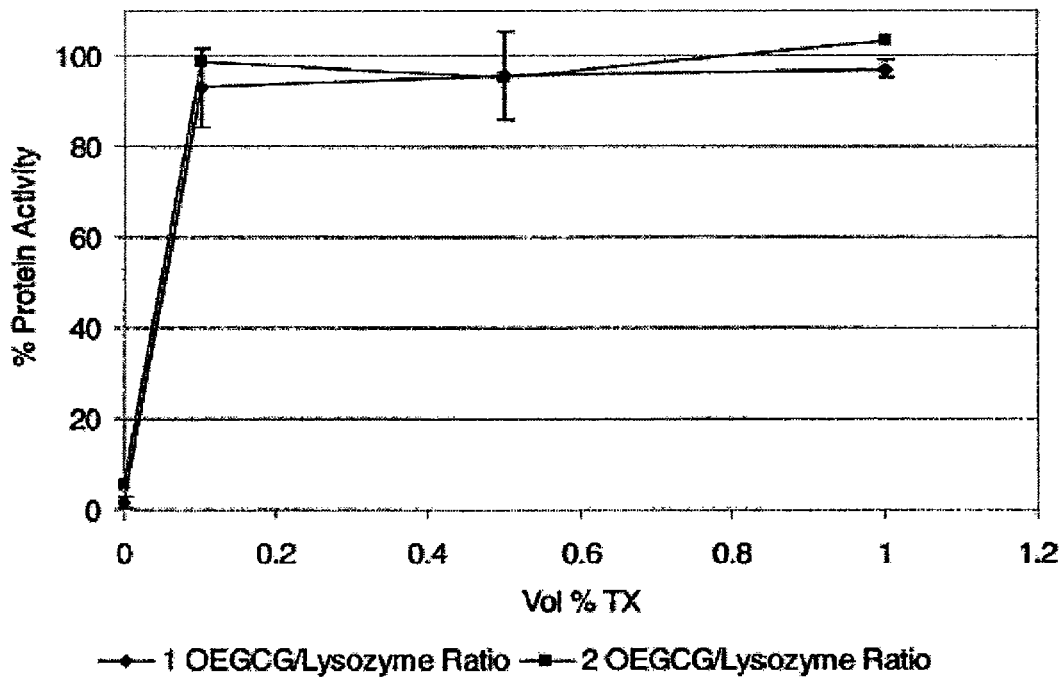
FIG. 30 illustrates the activity recovery of lysozyme with Triton X-100.

Recovery of protein activity: The nature of the interaction between OEGCG and the various proteins was tested by determining the effect of TX-100. As FIG. 2-4 indicate, the addition of TX-100 restored protein activity after complexation with OEGCG for both α-amylase and lysozyme to approximately 100% of the initial protein activity. FIG. 29 shows that for α-amylase, protein activity is initially dose dependently inhibited by OEGCG, as indicated by the fact that the higher OEGCG concentration results in lower protein activity without TX-100. As TX-100 is added to the α-amylase-OEGCG complex, activity very rapidly increased to nearly its original value for a range of TX-100 concentrations. FIG. 30 shows similar results for lysozyme. Complete inhibition of lysozyme is achieved with OEGCG and recover of protein activity is also nearly 100%.

Figure 31:
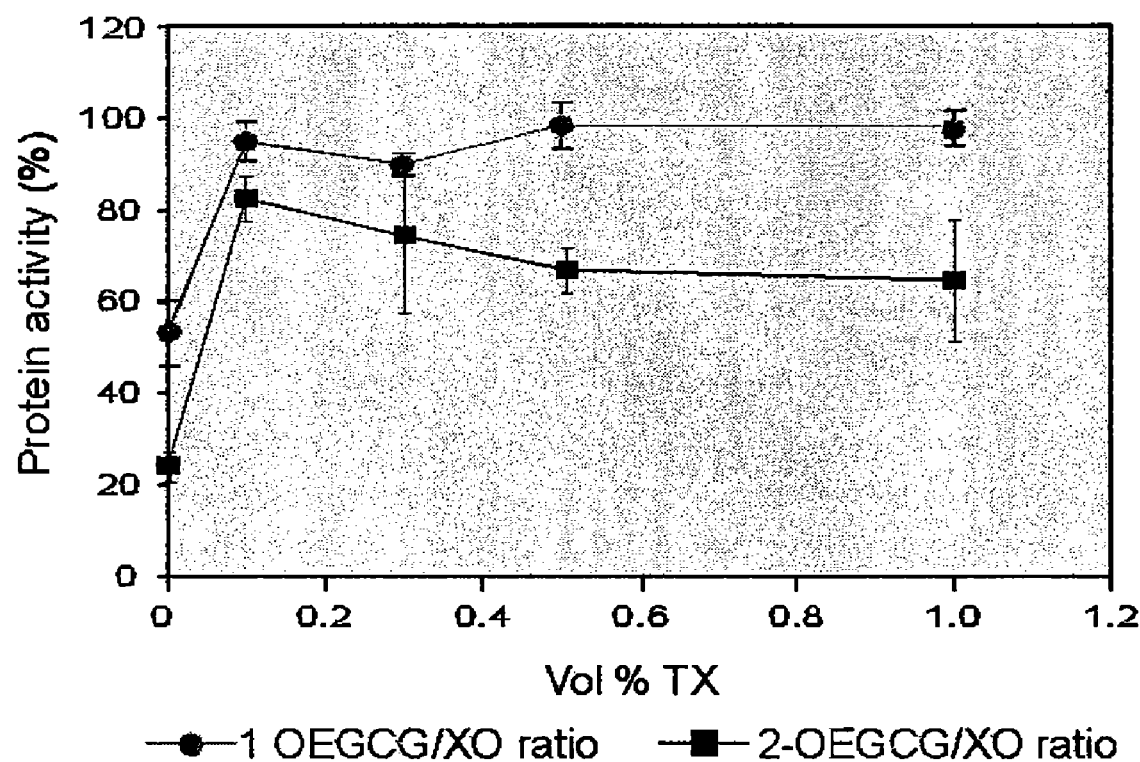
FIG. 31 illustrates the activity recovery of xanthine oxidase with Trition X-100.

The activity of xanthine oxidase also fully recovered when the weight ratio of OEGCG to protein was 1 (see Example 6), but the recovery was less beyond the ratio of 2 (FIG. 31). Catalase did not show obvious recovery as well as inhibition (data not shown).

Discussion: Protein inhibition by OEGCG is a non-specific interaction as evidenced by the activity suppression of all four proteins. Inhibition occurred despite dissimilarities in molecular weight, protein function, and protein charge and the concentration ratio of OEGCG to protein. In addition, the inhibition appears to occur in two different regimes. In the first regime, activity substantially decreases with additional OEGCG. At a critical concentration, additional OEGCG does not increase inhibition; the inhibition effect becomes almost saturated. It would be consistent with the fact that once all active sites capable of being inhibited by OEGCG are blocked, increasing the concentration has little effect on the overall enzyme inhibition.

Although the general trend is observed for all proteins, the maximum level of inhibition that can be achieved and the rate of the dose dependent response to OEGCG is protein specific. Catalase, a large protein with four subunits, shows much less inhibition compared to the much smaller lysozyme. However, size is only one factor and does not entirely explain the different dose dependent responses to OEGCG. Other factors may include the extent of the hydrophobic nature of the enzyme as well as the protein conformation and location of the active site.

Activity recovery with TX-100 establishes the type of interaction between OEGCG and the protein. As a hydrophobic competitor to the protein-OEGCG complex, dissociation to achieve activity recovery indicates that inhibition occurs through hydrophobic interactions. Activity recovery also establishes the fact that the nature of the OEGCG-protein interaction allows the function of the protein to be regained after dissociation.

As can be understood by one skilled in the art, many modifications to the exemplary embodiments described herein are possible. The invention is intended to encompass all such modification within its scope, as defined by the claims.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

TABLE 1

Synthesis of oligomeric EGCG

| sample | EGCG (g) | Acetaldehyde (g) | Molar ratio (EGCG:acetaldehyde) | Solvent (ml) | Time (d) | atmosphere | Yield (%) | $Mw^c$ | $Mn^c$ | $Mw/Mn^c$ |
|---|---|---|---|---|---|---|---|---|---|---|
| OE-1 | 0.2 | 1.0 | 1:52 | $12.5^a$ (0.04:0.17:0.79) | 1 | Air | 23 | 3600 | 3300 | 1.1 |
| OE-2 | 1.0 | 5.2 | 1:52 | $62.4^a$ (0.04:0.17:0.79) | 14 | Air | 25 | 3100 | 2800 | 1.1 |
| OE-3 | 1.0 | 5.2 | 1:52 | $62.4^a$ (0.04:0.17:0.79) | 2 | $N_2$ | 78 | 4000 | 3100 | 1.2 |
| OE-4 | 0.4 | 1.8 | 1:52 | $23.2^a$ (0.03:0.02:0.95) | 2 | $N_2$ | 28 | 2400 | 2100 | 1.1 |
| OE-5 | 0.5 | 2.5 | 1:52 | $36.2^b$ (0.18:0.15:0.67) | 2 | $N_2$ | 98 | 5200 | 4600 | 1.1 |

$^a$a mixture of acetic acid, ethanol and $H_2O$, volume ratio in parenthesis,
$^b$a mixture of acetic acid, DMSO and $H_2O$, volume ratio in parenthesis,
$^c$molecular weight was measured by SEC after acetylation.

TABLE 2

Synthesis of PEG conjugates with EGCG

| sample | PEG-CHO (g) | EGCG (g) | Molar ratio (PEG-CHO:EGCG) | Solvent (ml) | Time (d) | atmosphere | $Mw^d$ | $Mn^d$ | $Mw/Mn^d$ |
|---|---|---|---|---|---|---|---|---|---|
| | PEG-CHO(I) | | | | | | 7400 | 6300 | 1.2 |
| PE-1 | 0.65 | 0.18 | 1:3 | $12.1^a$ (0.02:0.5:0.48) | 14 | Air | 7600 | 6700 | 1.1 |
| PE-2 | 0.65 | 0.18 | 1:3 | $10.2^a$ (0.03:0.4:0.57) | 2 | $N_2$ | 7800 | 6500 | 1.2 |
| PE-3 | 0.27 | 0.5 | 1:20 | $9.5^a$ (0.03:0.4:0.57) | 2 | $N_2$ | 7900 | 6800 | 1.2 |
| PE-4 | 0.35 | 0.65 | 1:20 | $12.3^b$ (0.17:0.22:0.61) | 2 | $N_2$ | 7800 | 6600 | 1.2 |
| | PEG-CHO(II) | | | | | | 12200 | 10200 | 1.2 |
| PE-5 | 0.55 | 0.5 | 1:20 | $12.3^c$ (0.03:0.13:0.24:0.6) | 2 | $N_2$ | 12500 | 10600 | 1.2 |

$^a$a mixture of acetic acid, ethanol and $H_2O$, volume ratio in parenthesis,
$^b$a mixture of acetic acid, DMSO and $H_2O$, volume ratio in parenthesis,
$^c$a mixture of acetic acid, ethanol, DMSO and $H_2O$, volume ratio in parenthesis,
$^d$molecular weight was measured by SEC after acetylation.

TABLE 3

Synthesis of PEG conjugates with oligomeric EGCG

| sample | PEG-CHO (g) | OEGCG (g) | Molar ratio (PEG-CHO:OEGCG) | Solvent (ml) | Time (d) | Temp. (° C.) | atmosphere | Yield (%) | $Mw^d$ | $Mn^d$ | $Mw/Mn^d$ |
|---|---|---|---|---|---|---|---|---|---|---|---|
| | PEG-CHO(I) | | | | | | | | | | |
| PO-1 | 0.19 | 0.01 (OE-1) | 10:1 | $2.5^a$ (0.03:0.4:0.57) | 6 | 20 | Air | 7 | 10300 18000 | 9000 17100 | 1.1 1.1 |

TABLE 3-continued

Synthesis of PEG conjugates with oligomeric EGCG

| sample | PEG-CHO (g) | OEGCG (g) | Molar ratio (PEG-CHO:OEGCG) | Solvent (ml) | Time (d) | Temp. (°C.) | atmosphere | Yield (%) | Mw[d] | Mn[d] | Mw/Mn[d] |
|---|---|---|---|---|---|---|---|---|---|---|---|
| PO-2 | 0.28 | 0.1 (OE-1) | 1:1 | 3.9[a] (0.02:0.62:0.36) | 14 | 20 | Air | 42 | 10100 | 8800 | 1.1 |
| PO-3 | 0.61 | 0.3 (OE-2) | 1:1 | 16.3[b] (0.18:0.15:0.67) | 2 | 20 | $N_2$ | 75 | 10000 | 9000 | 1.1 |
| PO-4 | PEG-CHO(II) 1.0 | 0.21 (OE-3) | 1:1 | 20.8[c] (0.02:0.09:0.48:0.41) | 1 | 50 | $N_2$ | 64 | 15900 | 13200 | 1.2 |

[a] a mixture of acetic acid, ethanol and $H_2O$, volume ratio in parenthesis,
[b] a mixture of acetic acid, DMSO and $H_2O$, volume ratio in parenthesis,
[c] a mixture of acetic acid, ethanol, DMSO and $H_2O$, volume ratio in parenthesis,
[d] molecular weight was measured by SEC after acetylation.

TABLE 4

Free radical scavenging activity

| Sample | DPPH scavenging activity $IC_{50}$ (μM) | Superoxide radical scavenging activity $IC_{50}$ (μM) |
|---|---|---|
| EGCG | 7.3 ± 0.6[a] | 2.9 ± 0.3[a] |
| OEGCG | 4.9 ± 0.5[a] | 1.1 ± 0.2[a] |
| PEG-EGCG | 6.2 ± 0.3[a] | 0.9 ± 0.1[a] |
| PEG-OEGCG | 3.8 ± 0.8[a] | 0.4 ± 0.1[a] |
| Vitamin C | 44.7 ± 0.4 | 30.3 ± 0.3 |
| BHT | >>250.0 | >>250.0 |

[a] EGCG moiety concentration of samples, n = 3.

What is claimed is:

1. A method of conjugating a polymer having a free aldehyde group in the presence of acid to a flavonoid, comprising reacting the polymer with the flavonoid in the presence of an acid catalyst, the polymer being conjugated at the C6 and/or the C8 position of the A ring of the flavonoid.

2. The method of claim 1 wherein said free aldehyde group is generated by conversion of an acetal group on the polymer.

3. The method of claim 1 wherein said flavonoid is a catechin-based flavonoid.

4. The method of claim 2 wherein the catechin-based flavonoid is (−)-epicatechin, (−)-epigallocatechin, (+)-catechin, (−)-epicatechin gallate or (−)-epigallocatechin gallate.

5. The method of claim 3 wherein the catechin-based flavonoid is monomeric or is oligomeric.

6. The method of claim 1 wherein the flavonoid is oligomerized through: (i) enzyme-catalyzed oxidative coupling; (ii) aldehyde-mediated oligomerization; or (iii) a carbon-carbon linkage between the C6 or C8 position on the A ring of a first monomeric unit to the C6 or C8 position on the A ring of a second monomeric unit.

7. The method of claim 6 wherein the flavonoid is oligomerized via a carbon-carbon linkage between the C6 position on the A ring of the first monomeric unit to the C8 position on the A ring of the second monomeric unit or wherein the flavonoid is oligomeric (−)-epigallocatechin gallate (OEGCG) oligomerized through carbon-carbon C6-C6, C6-C8, C8-C6 or C8-C8 linkages of (−)-epigallocatechin gallate monomers.

8. The method of claim 1 wherein the polymer is aldehyde-terminated poly (ethylene glycol), aldehyde-derivatized hyaluronic acid, hyaluronic acid aminoacetylaldehyde diethylacetal conjugate, derivatized hyaluronic acid-tyramine, hyaluronic acid aminoacetylaldehyde diethylacetal conjugate-tyramine, cyclotriphosphazene core phenoxymethyl(methylhydrazono) dendrimer or thiophosphoryl core phenoxymethyl(methylhydrazono) dendrimer.

9. The method of claim 1 wherein the polymer is a protein, a peptide, a polysaccharide or a nucleic acid.

10. The method of claim 1 wherein the flavonoid has augmented biological flavonoid properties.

* * * * *